US012760002B2

(12) United States Patent
Kim et al.

(10) Patent No.: US 12,760,002 B2
(45) Date of Patent: Oct. 13, 2026

(54) INDAZOLE DERIVATIVE AND USE THEREOF

(71) Applicant: KOREA RESEARCH INSTITUTE OF CHEMICAL TECHNOLOGY, Daejeon (KR)

(72) Inventors: Pil Ho Kim, Daejeon (KR); Seong Hwan Kim, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 912 days.

(21) Appl. No.: 17/785,743

(22) PCT Filed: Dec. 16, 2020

(86) PCT No.: PCT/KR2020/018477
§ 371 (c)(1),
(2) Date: Jun. 15, 2022

(87) PCT Pub. No.: WO2021/125802
PCT Pub. Date: Jun. 24, 2021

(65) Prior Publication Data

US 2023/0116733 A1 Apr. 13, 2023
US 2025/0243181 A2 Jul. 31, 2025

(30) Foreign Application Priority Data

Dec. 16, 2019 (KR) ........................ 10-2019-0168364

(51) Int. Cl.
*C07D 401/14* (2006.01)
*C07D 401/04* (2006.01)
(Continued)

(52) U.S. Cl.
CPC ......... *C07D 401/14* (2013.01); *C07D 401/04* (2013.01); *C07D 401/12* (2013.01);
(Continued)

(58) Field of Classification Search
None
See application file for complete search history.

(56) References Cited

U.S. PATENT DOCUMENTS 10,343,992 B2 7/2019 Jones et al.
10,669,240 B2 6/2020 Hood et al.
(Continued)

FOREIGN PATENT DOCUMENTS

FR 2867778 A1 9/2005
JP 2018537553 A 12/2018
(Continued)

OTHER PUBLICATIONS

Extended European Search Report issued for European Patent Application No. 20 902 519.6 on Sep. 20, 2023, 15 pages.
(Continued)

*Primary Examiner* — Adam C Milligan
*Assistant Examiner* — Jason M. Nolan
(74) *Attorney, Agent, or Firm* — ROTHWELL, FIGG, ERNST & MANBECK, P.C.

(57) ABSTRACT

Indazole derivatives, and use thereof, wherein the indazole derivatives have TRIB2 or YAP inhibitory activity, and can be effectively used as a pharmaceutical composition for treating cancer, narcolepsy, and fasciitis.

12 Claims, 1 Drawing Sheet

(51) Int. Cl.
*C07D 401/12* (2006.01)
*C07D 405/14* (2006.01)
*C07D 409/14* (2006.01)
*C07D 471/04* (2006.01)

(52) U.S. Cl.
CPC ......... *C07D 405/14* (2013.01); *C07D 409/14* (2013.01); *C07D 471/04* (2013.01)

(56) References Cited

U.S. PATENT DOCUMENTS

| | | | |
|---|---|---|---|
| 11,008,514 | B2 | 5/2021 | Wittek et al. |
| 11,066,388 | B2 | 7/2021 | Hood et al. |
| 2006/0004000 | A1 | 1/2006 | D'Orchymont et al. |
| 2007/0185187 | A1 | 8/2007 | D'Orchymont et al. |
| 2011/0021467 | A1 | 1/2011 | D'Orchymont et al. |
| 2021/0121448 | A1 | 4/2021 | Deshmukh et al. |

FOREIGN PATENT DOCUMENTS

| | | | |
|---|---|---|---|
| KR | 10-2014-0074943 | A | 6/2014 |
| KR | 10-2016-0135283 | A | 11/2016 |
| KR | 10-1796781 | B1 | 11/2017 |
| KR | 10-1936851 | B1 | 1/2019 |
| KR | 2019-0056758 | A | 5/2019 |
| KR | 10-2019-0071782 | A | 6/2019 |
| WO | 2005/092890 | A2 | 10/2005 |
| WO | 2006/001894 | A1 | 1/2006 |
| WO | 2016/156816 | A1 | 10/2016 |
| WO | 2019/165192 | A1 | 8/2019 |
| WO | 2019/215075 | A1 | 11/2019 |

OTHER PUBLICATIONS

International Search Report issued for International Application No. PCT/KR2020/018477 on Mar. 29, 2021, 8 pages.

Eyers, P. A. et al. "Tribbles in the 21st Century: The Evolving Roles of Tribbles Pseudokinases in Biology and Disease", Trends Cell Biol., 2017; 27(4): 284-298.

Zhang, H. H. et al. "miR-511 induces the apoptosis of radioresistant lung adenocarcinoma cells by triggering BAX", Oncol Rep., 2014; 31(3): 1473-1479.

Wang, P. Y. et al. "Let-7c inhibits A549 cell proliferation through oncogenic TRIB2 related factors", FEBS Letters, 2013; 587(16): 2675-2681.

Bisoffi, M. et al. "Expression Profiles Of Androgen Independent Bone Metastatic Prostate Cancer Cells Indicate Up-regulation of the Putative Serine-threonine Kinase GS3955", J Urol., 2004; 172(3): 1145-1150.

Wang, J. et al. "TRIB2 Acts Downstream of Wnt/TCF in Liver Cancer Cells to Regulate YAP and C/EBPa Function", Mol Cell., 2013; 51(2): 211-225.

Keeshan, K. et al. "Tribbles homolog 2 inactivates C/EBPα and causes acute myelogenous leukemia", Cancer Cell., 2006; 10(5): 401-411.

Keeshan, K. et al. "Tribbles homolog 2 (Trib2) and HoxA9 cooperate to accelerate acute myelogenous leukemia", Blood Cells Mol Dis., 2008; 40(1): 119-121.

Hill, R. et al. "TRIB2 as a biomarker for diagnosis and progression of melanoma", Carcinogenesis, 2015; 36(4): 469-477.

Jung, H. W. et al. "Inhibitory effect of Cinnamomi Cortex extract on motility of prostate cancer cells through reducing YAP activity", Kor. J. Herbol., 2019; 34(3): 55-61.

Sudol, M., "Yes-associated protein (YAP65) is a proline-rich phosphoprotein that binds to the SH3 domain of the Yes protooncogene product", Oncogene, 1994; 9(8): 2145-2152.

Pan, D., "The hippo signaling pathway in development and cancer", Dev Cell., 2010; 19(4): 491-505.

Zhao, B. et al. "Both TEAD-binding and WW domains are required for the growth stimulation and oncogenic transformation activity of yes-associated protein", Cancer Res., 2009; 69(3): 1089-1098.

Wang, J. et al. "Mutual interaction between YAP and CREB promotes tumorigenesis in liver cancer", Hepatology, 2013; 58(3): 1011-1020.

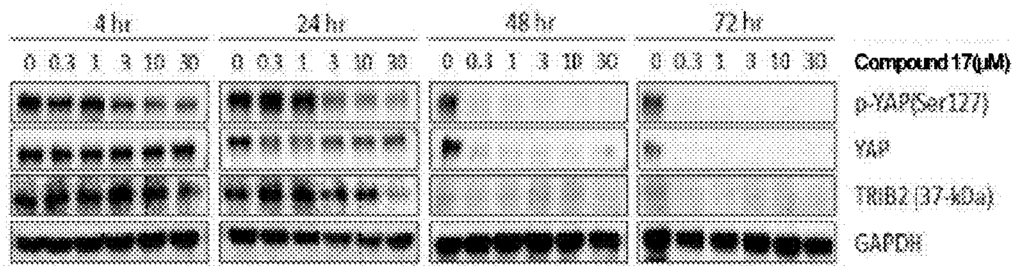
4 hr
24 hr
48 hr
72 hr
0 0.3 1 3 10 30
0 0.3 1 3 10 30
0 0.3 1 3 10 30
0 0.3 1 3 10 30
Compound 17(μM)
p-YAP(Ser127)
YAP
TRIB2 (37-kDa)
GAPDH
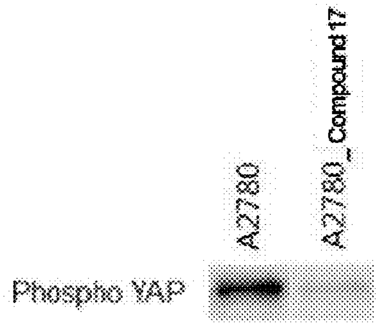
A2780
A2780_Compound 17
Phospho YAP

INDAZOLE DERIVATIVE AND USE THEREOF

CROSS REFERENCE TO RELATED APPLICATION(S)

This application is a 35 U.S.C. 371 National Phase Entry Application from PCT/KR2020/018477 filed on Dec. 16, 2020, which claims priority to and the benefits of Korean Patent Application No. 10-2019-0168364, filed on Dec. 16, 2019, the entire contents of which are incorporated herein by reference.

TECHNICAL FIELD

The present invention relates to a novel indazole derivative and a use thereof and, more specifically, to a novel indazole derivative having inhibitory activity against TRIB2 or YAP, and a pharmaceutical composition comprising same for prevention or treatment of cancer, narcolepsy, and fasciitis.

BACKGROUND ART

Tribbles pseudokinases 2 (TRIB2) functions as a molecular adaptor involved in various signaling pathways. Specifically, it has been known according to various in vitro and in vivo experiments and histological research on cancer patients that TRIB2 plays a critical role in tumorigenesis for various cancers and is implicated in the growth/survival of androgen-independent prostate cancer, liver cancer, acute myeloid leukemia (AML), lung cancer, melanoma, anticancer therapy-resistant cancers (Evers, P. A. et al., Trends Cell Biol., 27(4), 284-298, 2017; Zhang, H. H. et al., Oncol Rep., 31(3), 1473-1479, 2014; Wang, P. Y. et al., FEBS Lett., 587(16), 2675-2681, 2013; Bisoffi, M. et al., J Urol., 172(3), 1145-1150, 2004; Wang, J. et al., Mol Cell., 51(2), 211-225, 2013; Keeshan, K. at al., Cancer Cell., 10(5), 401-411, 2006; Keeshan, K. et al., Blood Cells Mol Dis., 40(1), 119-121, 2008; and Hill, R. et al., Carcinogenesis, 36(4), 469-477, 2015).

Yes-associated protein 1 (YAP) is an important factor functioning to mediate the Hippo signaling pathway, which is involved in cell growth and tissue homeostasis and regulates the growth and death of cells by inhibiting intercellular contact. This regulatory mechanism is considered to be important for cancer therapy because an aberrational change, if occurring therein, might provoke cancer (Hyo Won, JUNG, et al., Inhibitory effect of Cinnamomi Cortex extract on motility of prostate cancer cells through reducing YAP activity, Kor. J. Herbol., 34(3), 55-61, 2019; Sudol, M., Yes-associated protein (YAP65) is a prolinerich phosphoprotein that binds to the SH3 domain of the Yes proto-oncogene product, Oncogene, 9(8), 2145-2152, 1994; Pan, D., The Hippo signaling pathway in development and cancer, Dev Cell., 19(4), 491-505, 2010; and Zhao, B. et al., Both TEAD-binding and WW domains are required for the growth stimulation and oncogenic transformation activity of yes-associated protein, Cancer Res., 69(3), 1089-1098, 2009).

Among others, YAP, the downstream effector of the Hippo signaling pathway, is known, together with cAMP response element-binding protein (CREB), to be linked to hepatocarcinogenesis (Wang, J. et al., Mutual interaction between YAP and CREB promotes tumorigenesis in liver cancer, Hepatology, 58(3), 1011-1020, 2013).

With respect to pharmaceutical compositions containing indazole derivatives as active ingredients for preventing or treating cancer, narcolepsy, and fasciitis, reference may be made to Korean Patent Number 10-1796781, which discloses novel indazole derivatives, preparation method therefor, and pharmaceutical composition containing same for preventing or treating cancer and to Korean Patent Number 10-1936851, which discloses pyrazolopyridine or indazole derivatives as protein kinase inhibitors.

However, the indazole derivatives of Chemical Formulas 1 and 2 of the present disclosure that have inhibitory activity against TRIB2 or YAP and can be used for therapy for cancer, narcolepsy and fasciitis have not been disclosed anywhere in previous reports.

Leading to the present disclosure, the research has been conducted into indazole derivatives and resulted in the finding that the indazole derivatives have excellent inhibitory activity against TRIB2 or YAP.

DISCLOSURE OF INVENTION

Technical Problem

The present disclosure aims to provide novel indazole derivatives and a use thereof and, more specifically, to novel indazole derivatives having inhibitory activity against TRIB2 and YAP and a pharmaceutical composition comprising same for prevention and treatment of cancer, narcolepsy, and fasciitis.

Solution to Problem

The present disclosure relates to a compound represented by the following Chemical Formula 1, an optical isomer thereof, or a pharmaceutically acceptable salt thereof:

[Chemical Formula 1]

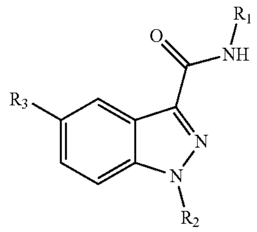

wherein, $R_1$ is at least one substituent selected from the group consisting of a substituted or unsubstituted $C_4$-$C_{12}$ heterocycloalkyl, a radical forming a substituted or unsubstituted $C_4$-$C_{12}$ heterocycloalkyl with the N linked thereto, a substituted or unsubstituted $C_4$-$C_{12}$ cycloalkyl, a substituted or unsubstituted $C_4$-$C_{12}$ heteroaryl, a substituted or unsubstituted $C_1$-$C_4$ alkyl $C_4$-$C_{12}$ heterocycloalkyl, and a substituted or unsubstituted $C_1$-$C_4$ alkyl $C_4$-$C_{12}$ heteroaryl;

wherein the substituted heterocycloalkyl, cycloalkyl, heteroaryl, $C_1$-$C_4$ alkyl $C_4$-$C_{12}$ heterocycloalkyl, or $C_1$-$C_4$ alkyl $C_4$-$C_{12}$ heteroaryl has as a substituent at least one selected from the group consisting of a hydrogen atom, a $C_1$-$C_4$ alkyl, halogen, —$NH_2$, —OH, Boc(tert-butoxycarbonyl), C(=O)$NH_2$, C(=O)$CF_3$,

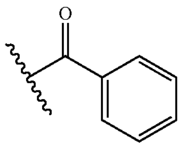 and 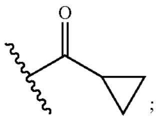 ;

$R_2$ is a substituent selected from the group consisting of a hydrogen atom, a $C_1$-$C_6$ alkyl, acetyl, trifluoroacetyl, Boc(tert-butoxycarbonyl),

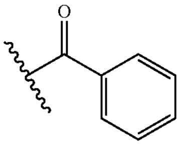, 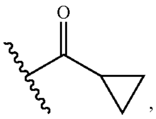, and 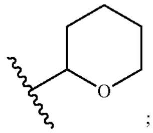 ;

$R_3$ may form a substituted or unsubstituted $C_4$-$C_{12}$ aryl, a substituted or unsubstituted $C_4$-$C_{12}$ heteroaryl, a substituted or unsubstituted $C_4$-$C_{12}$ heterocycloalkyl, or a substituted or unsubstituted pyridine, wherein the substituted $C_4$-$C_{12}$ aryl, $C_4$-$C_{12}$ heteroaryl, $C_4$-$C_{12}$ heterocycloalkyl, or pyridine has as a substituent at least one selected from the group consisting of a hydrogen atom, halogen, a $C_1$-$C_6$ alkyl, a $C_4$-$C_6$ heterocycloalkyl, a $C_1$-$C_4$ alkyl $C_4$-$C_6$ heterocycloalkyl, a $C_1$-$C_4$ alkyl $C_4$-$C_6$ aryl, and

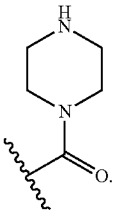 [SMILES: *C(=O)N1CCNCC1]

In the compound represented by Chemical Formula 1 according to the present disclosure, $R_1$ is a substituent selected from the group consisting of a substituted or unsubstituted piperidine, a substituted or unsubstituted pyridine, a substituted or unsubstituted tetrahydroisoquinoline, a substituted or unsubstituted

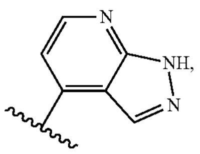 [SMILES: *c1ccnc2[nH]ncc12]

and a radical forming a substituted or unsubstituted

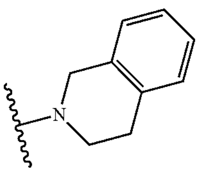 [SMILES: *N1CCc2ccccc2C1]

with the N linked thereto;

wherein the substituted piperidine, pyridine, or tetrahydroisoquinoline has as a substituent at least one selected from the group consisting of a hydrogen atom, a $C_1$-$C_4$ alkyl, halogen, —$NH_2$, —OH, Boc(tert-butoxycarbonyl),

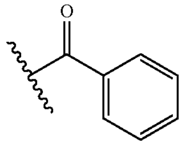 and 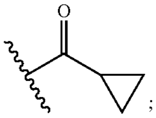 ;

$R_2$ is a substituent selected from the group consisting of a hydrogen atom, a $C_1$-$C_6$ alkyl, acetyl, trifluoroacetyl, Boc(tert-butoxycarbonyl),

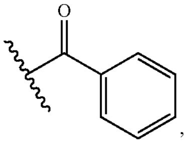, 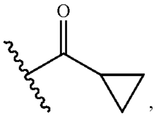, and 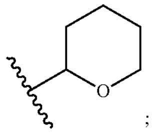 [SMILES: *C1CCCCO1] ;

$R_3$ may form a substituted or unsubstituted $C_4$-$C_{12}$ aryl, a substituted or unsubstituted $C_4$-$C_{12}$ heteroaryl, a substituted or unsubstituted $C_4$-$C_{12}$ heterocycloalkyl, or a substituted or unsubstituted pyridine, wherein the substituted $C_4$-$C_{12}$ aryl, $C_4$-$C_{12}$ heteroaryl, $C_4$-$C_{12}$ heterocycloalkyl, or pyridine has as a substituent at least one selected from the group consisting of a hydrogen atom, halogen, a $C_1$-$C_6$ alkyl, a $C_4$-$C_6$ heterocycloalkyl, a $C_1$-$C_4$ alkyl $C_4$-$C_6$ heterocycloalkyl, a $C_1$-$C_4$ alkyl $C_4$-$C_6$ aryl, and

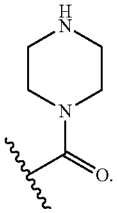 [SMILES: *C(=O)N1CCNCC1]

In addition, the present disclosure pertains to a compound represented by the following Chemical Formula 2, an optical isomer thereof, or a pharmaceutically acceptable salt thereof.

A compound represented by the following Chemical Formula 2, an optical isomer thereof, and a pharmaceutically acceptable salt thereof;

[Chemical Formula 2]

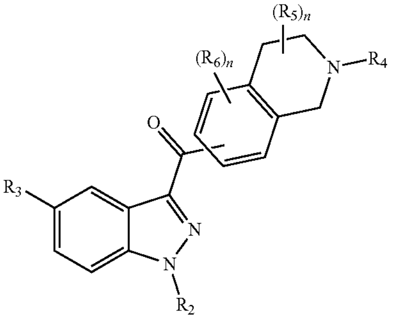

wherein, $R_2$ is a substituent selected from the group consisting of a hydrogen atom, a $C_1$-$C_6$ alkyl, acetyl, trifluoroacetyl, Boc(tert-butoxycarbonyl), and

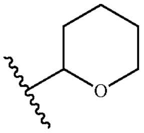

;

$R_3$ may form a substituted or unsubstituted $C_4$-$C_{12}$ aryl, a substituted or unsubstituted $C_4$-$C_{12}$ heteroaryl, a substituted or unsubstituted $C_4$-$C_{12}$ heterocycloalkyl, or a substituted or unsubstituted pyridine, wherein the substituted $C_4$-$C_{12}$ aryl, $C_4$-$C_2$ heteroaryl, $C_4$-$C_{12}$ heterocycloalkyl, or pyridine has as a substituent at least one selected from the group consisting of a hydrogen atom, halogen, a $C_1$-$C_6$ alkyl, a $C_4$-$C_6$ heterocycloalkyl, a $C_1$-$C_4$ alkyl $C_4$-$C_6$ heterocycloalkyl, a $C_1$-$C_4$ alkyl $C_4$-$C_6$ aryl, or

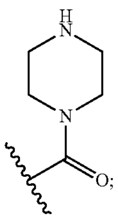

;

$R_4$ is a substituent selected from the group consisting of a hydrogen atom, a $C_1$-$C_6$ alkyl, acetyl, and trihaloacetyl;

$R_5$ are each independently a substituent selected from the group consisting of a hydrogen atom, hydroxy, halogen, and a $C_1$-$C_6$ alkyl;

$R_6$ are each independently a substituent selected from the group consisting of a hydrogen atom, hydroxy, nitro, amino, halogen, a $C_1$-$C_4$ alkyl, and a $C_1$-$C_4$ alkoxy; and n is an integer of 0, 1, or 2.

Concrete examples of the compound of Chemical Formula 1 or 2 according to the present disclosure include:

tert-butyl-4-(5-(2-fluoropyridin-3-yl)-1H-indazole-3-carboxamido)piperidine-1-carboxylate (Compound 1);

5-(2-fluoropyridin-3-yl)-N-(piperidin-4-yl)-1H-indazole-3-carboxamide (Compound 2);

tert-butyl 4-(5-(pyridin-3-yl)-1H-indazole-3-carboxamido) piperidine-1-carboxylate (Compound 3);

N-(piperidin-4-yl)-5-(pyridin-3-yl)-1H-indazole-3-carboxamide (Compound 4);

tert-butyl 4-(5-(2-fluorophenyl)-1H-indazole-3-carboxamido)piperidine-1-carboxylate (Compound 5);

5-(2-fluorophenyl)-N-(piperidin-4-yl)-1H-indazole-3-carboxamide (Compound 6);

5-(2-fluoropyridin-3-yl)-N-(piperidin-4-yl)-1H-pyrrolo[2,3-b]pyridine-3-carboxamide (Compound 7);

5-(2-fluoropyridin-3-yl)-N-(piperidin-4-yl)-1H-indole-3-carboxamide (Compound 8);

5-(2-fluoropyridin-3-yl)-1-methyl-N-(piperidin-4-yl)-1H-indazole-3-carboxamide (Compound 9);

1-benzoyl-N-(1-benzoylpiperidin-4-yl)-5-(2-fluoropyridin-3-yl)-1H-indazole-3-carboxamide (Compound 10);

1-(cyclopropanecarbonyl)-N-(1-(cyclopropanecarbonyl)piperidin-4-yl)-5-(2-fluoropyridin-3-yl)-1H-indazole-3-carboxamide (Compound 11);

N-(1-benzoylpiperidin-4-yl)-5-(2-fluoropyridin-3-yl)-1H-indazole-3-carboxamide (Compound 12);

5-(2-fluoropyridin-4-yl)-N-(piperidin-4-yl)-1H-indazole-3-carboxamide (Compound 13);

N-cyclohexyl-5-(2-fluoropyridin-3-yl)-1H-indazole-3-carboxamide (Compound 14);

1-(5-(2-fluoropyridin-3-yl)-1H-indazole-3-carbonyl)piperidine-4-carboxamide (Compound 15);

5-(2-fluoropyridin-3-yl)-N-((1r,4r)-4-hydroxycyclohexyl)-1H-indazole-3-carboxamide (Compound 16);

5-(2-fluoropyridin-3-yl)-N-(pyridin-4-yl)-1H-indazole-3-carboxamide (Compound 17);

N-((1s,4s)-4-aminocyclohexyl)-5-(2-fluoropyridin-3-yl)-1H-indazole-3-carboxamide (Compound 18);

N-((1r,4r)-4-aminocyclohexyl)-5-(2-fluoropyridin-3-yl)-1H-indazole-3-carboxamide (Compound 19);

5-(2-fluoropyridin-3-yl)-N-(pyrrodin-3-yl)-1H-indazole-3-carboxamide (Compound 20);

(3,4-dihydroisoquinolin-2-(1H)-yl)(5-(2-fluoropyridin-3-yl)-1H-indazol-3-yl)methanone (Compound 21);

5-(2-fluoropyridin-3-yl)-N-(2-morpholinoethyl)-1H-indazole-3-carboxamide (Compound 22);

(5-(2-fluoropyridin-3-yl)-1H-indazol-3-yl)(4-methylpiperazin-1-yl)methanone (Compound 23);

5-(2-fluoropyridin-3-yl)-N-(2-(2,2,2-trifluoroacetyl)-1,2,3,4-tetrahydroisoquinolin-7-yl)-1H-indazole-3-carboxamide (Compound 24);

5-(3,4-difluorophenyl)-N-(pyridin-4-yl)-1H-indazole-3-carboxamide (Compound 25);

5-(1H-pyrazol-4-yl)-N-(pyridin-4-yl)-1H-indazole-3-carboxamide (Compound 26);

N-(pyridin-4-yl)-5-(1,3,5-trimethyl-1H-pyrazol-4-yl)-1H-indazole-3-carboxamide (Compound 27);

5-(1-isopropyl-1H-pyrazol-4-yl)-N-(pyridin-4-yl)-1H-indazole-3-carboxamide (Compound 28);

5-(1-methyl-1H-pyrazol-4-yl)-N-(pyridin-4-yl)-1H-indazole-3-carboxamide (Compound 29);

tert-butyl 5-(1-(1-(tert-butoxycarbonyl)piperidin-4-yl)-1H-pyrazol-4-yl)-3-(pyridin-4-ylcarbamoyl)-1H-indazole-1-carboxylate (Compound 30);

tert-butyl 5-(4-(4-(tert-butoxycarbonyl)piperazine-1-carbonyl)phenyl)-3-(pyridin-4-ylcarbamoyl)-1H-indazole-1-carboxylate (Compound 31);

tert-butyl 5-(4-((4-(tert-butoxycarbonyl)piperazin-1-yl)methyl)phenyl)-3-(pyridin-4-ylcarbamoyl)-1H-indazole-1-carboxylate (Compound 32);

5-(1-benzyl-1H-pyrazol-4-yl)-N-(pyridin-4-yl)-1H-indazole-3-carboxamide (Compound 33);

5-(furan-3-yl)-N-(pyridin-4-yl)-1H-indazole-3-carboxamide (Compound 34);

tert-butyl 5-(1-(tert-butoxycarbonyl)-1,2,3,6-tetrahydropyridin-4-yl)-3-(pyridin-4-ylcarbamoyl)-1H-indazole-1-carboxylate (Compound 35);

5-(1-propyl-1H-pyrazol-4-yl)-N-(pyridin-4-yl)-1H-indazole-3-carboxamide (Compound 36);

5-(2,3-dihydrobenzo[b][1,4]dioxin-6-yl)-N-(pyridin-4-yl)-1-(tetrahydro-2H-pyran-2-yl)-1H-indazole-3-carboxamide (Compound 37);

tert-butyl 4-(4-(3-(pyridin-4-ylcarbamoyl)-1-(tetrahydro-2H-pyran-2-yl)-1H-indazol-5-yl)benzyl)piperazine-1-carboxylate (Compound 38);

tert-butyl 4-(3-(pyridin-4-ylcarbamoyl)-1-(tetrahydro-2H-pyran-2-yl)-1H-indazol-5-yl)-3,6-dihydropyridine-1(2H)-carboxylate (Compound 39);

tert-butyl 4-(4-(3-(pyridin-4-ylcarbamoyl)-1-(tetrahydro-2H-pyran-2-yl)-1H-indazol-5-yl)phenyl)piperazine-1-carboxylate (Compound 40);

5-(5-formylfuran-2-yl)-N-(pyridin-4-yl)-1-(tetrahydro-2H-pyran-2-yl)-1H-indazole-3-carboxamide (Compound 41);

N-(pyridin-4-yl)-5-(1,2,3,6-tetrahydropyridin-4-yl)-1H-indazole-3-carboxamide (Compound 42);

5-(benzo[b]thiophen-2-yl)-N-(pyridin-4-yl)-1-(tetrahydro-2H-pyran-2-yl)-1H-indazole-3-carboxamide (Compound 43);

5-(2-(dimethylamino)pyrimidin-5-yl)-N-(pyridin-4-yl)-1-(tetrahydro-2H-pyran-2-yl)-1H-indazole-3-carboxamide (Compound 44);

5-(6-formylbenzo[d][1,3]dioxol-5-yl)-N-(pyridin-4-yl)-1-(tetrahydro-2H-pyran-2-yl)-1H-indazole-3-carboxamide (Compound 45);

5-(4-(piperazin-1-yl)phenyl)-N-(pyridin-4-yl)-1H-indazole-3-carboxamide hydrochloride (Compound 46);

5-(5-formylfuran-2-yl)-N-(pyridin-4-yl)-1H-indazole-3-carboxamide (Compound 47);

5-(benzo[b]thiophen-2-yl)-N-(pyridin-4-yl)-1H-indazole-3-carboxamide (Compound 48);

5-(2-fluoropyridin-3-yl)-N-(pyridin-4-ylmethyl)-1-(tetrahydro-2H-pyran-2-yl)-1H-indazole-3-carboxamide (Compound 49);

5-(2-(dimethylamino)pyrimidin-5-yl)-N-(pyridin-4-yl)-1H-indazole-3-carboxamide (Compound 50);

5-(2-fluoropyridin-3-yl)-N-(pyridin-4-ylmethyl)-1H-indazole-3-carboxamide (Compound 51);

5-(6-formylbenzo[d][1,3]dioxol-5-yl)-N-(pyridin-4-yl)-1H-indazole-3-carboxamide (Compound 52);

5-(2-fluoropyridin-3-yl)-1-(tetrahydro-2H-pyran-2-yl)-N-(2-(2,2,2-trifluoroacetyl)-1,2,3,4-tetrahydroisoquinolin-7-yl)-1H-indazole-3-carboxamide (Compound 53);

5-(2-fluoropyridin-3-yl)-1-(tetrahydro-2H-pyran-2-yl)-N-(1,2,3,4-tetrahydroisoquinolin-7-yl)-1H-indazole-3-carboxamide (Compound 54);

5-(2-fluoropyridin-3-yl)-N-(1,2,3,4-tetrahydroisoquinolin-7-yl)-1H-indazole-3-carboxamide hydrochloride (Compound 55);

5-(6-(piperidin-1-ylmethyl)benzo[d][1,3]dioxol-5-yl)-N-(pyridin-4-yl)-1H-indazole-3-carboxamide (Compound 56);

tert-butyl 4-((5-(3-(pyridin-4-ylcarbamoyl)-1-(tetrahydro-2H-pyran-2-yl)-1H-indazol-5-yl)furan-2-yl)methyl)piperazine-1-carboxylate (Compound 57);

N-(1,1-dimethyl-2-(2,2,2-trifluoroacetyl)-1,2,3,4-tetrahydroisoquinolin-7-yl)-5-(2-fluoropyridin-3-yl)-1H-indazole-3-carboxamide (Compound 58);

N-(1,1-dimethyl-1,2,3,4-tetrahydroisoquinolin-7-yl)-5-(2-fluoropyridin-3-yl)-1H-indazole-3-carboxamide (Compound 59);

5-(2-fluoropyridin-3-yl)-N-(1-methyl-1H-pyrazolo[3,4-b]pyridin-4-yl)-1-(tetrahydro-2H-pyran-2-yl)-1H-indazole-3-carboxamide (Compound 60);

tert-butyl 4-(4-(3-(pyridin-4-ylcarbamoyl)-1-(tetrahydro-2H-pyran-2-yl)-1H-indazol-5-yl)benzoyl)piperazine-1-carboxylate (Compound 61);

tert-butyl 4-(4-(3-(pyridin-4-ylcarbamoyl)-1-(tetrahydro-2H-pyran-2-yl)-1H-indazol-5-yl)benzyl)piperazine-1-carboxylate (Compound 62);

5-(2-fluoropyridin-3-yl)-N-(1-methyl-1,2,3,4-tetrahydroisoquinolin-7-yl)-1H-indazole-3-carboxamide (Compound 63);

5-(2-fluoropyridin-3-yl)-N-(1,2,3,4-tetrahydroisoquinolin-6-yl)-1H-indazole-3-carboxamide (Compound 64);

5-(2-fluoropyridin-3-yl)-N-(1-methyl-1H-pyrazolo[3,4-b]pyridin-4-yl)-1H-indazole-3-carboxamide (Compound 65);

5-(2-fluoropyridin-3-yl)-N-(pyridin-4-yl)-1-(tetrahydro-2H-pyran-2-yl)-1H-indazole-3-carboxamide (Compound 66);

5-(4-(piperazine-1-carbonyl)phenyl)-N-(pyridin-4-yl)-1H-indazole-3-carboxamide (Compound 67);

5-(4-(piperazin-1-ylmethyl)phenyl)-N-(pyridin-4-yl)-1H-indazole-3-carboxamide (Compound 68);

5-(5-(piperazin-1-ylmethyl)furan-2-yl)-N-(pyridin-4-yl)-1H-indazole-3-carboxamide (Compound 69);

5-(5-(piperidin-1-ylmethyl)furan-2-yl)-N-(pyridin-4-yl)-1-(tetrahydro-2H-pyran-2-yl)-1H-indazole-3-carboxamide (Compound 70);

N-(3,3-dimethyl-1,2,3,4-tetrahydroisoquinolin-7-yl)-5-(2-fluoropyridin-3-yl)-1H-indazole-3-carboxamide (Compound 71);

5-(5-(piperidin-1-ylmethyl)furan-2-yl)-N-(pyridin-4-yl)-1H-indazole-3-carboxamide hydrochloride (Compound 72); and 5-(1-(piperidin-4-yl)-1H-pyrazol-4-yl)-N-(pyridin-4-yl)-1H-indazole-3-carboxamide hydrochloride (Compound 73).

Unless otherwise indicated, the terms used herein have the meanings set forth therefore in the following. Any terms that are not defined herein should be understood to have the meaning commonly accepted in the art.

The term "halogen" refers to fluorine (F), chlorine (Cl), bromine (Br), or iodine (I).

The term "alkyl" refers to a monovalent linear or branched hydrocarbon radical. Examples include methyl, ethyl, propyl, n-butyl, iso-butyl, tert-butyl, and 1-methylpropyl.

The term "cycloalkyl" refers to a monovalent saturated hydrocarbon radical in a cyclic form. Examples include cyclopropyl, cyclobutyl, cyclopentyl, cyclohexyl, cycloheptyl, cyclooctyl, etc.

The term "heterocycloalkyl" refers to a monovalent saturated ring-shaped hydrocarbon radical bearing at least one heteroatom, such as N, O, or S, as a ring member. According to numbers and kinds of the heteroatoms and numbers of carbon atoms within the ring, there are various heterocycloalkyl radicals including aziridinyl, pyrrolidinyl, piperidinyl, piperazinyl, morpholinyl, tetrahydrofuranyl, tetrahydropyranyl, tetrahydroisoquinoline, etc.

The term "aryl" refers to an aromatic substituent having at least one ring with a pi-system of electrons delocalized therein, as exemplified by phenyl, benzyl, etc.

The term "heteroaryl" refers to an aromatic ring compound bearing at least one heteroatom, such as N, O, or S, as a ring member. According to numbers and kinds of the heteroatoms and numbers of carbon atoms within the ring, there are various heteroaryl radicals including pyrrolyl, furanyl, pyrimidinyl, pyranyl, etc.

Moreover, each of the compounds of the present disclosure may have at least one chiral carbon atom and may be in a racemic mixture or an optically active form. All of the compounds and diastereomers fall within the scope of the present disclosure.

As used herein, the term "pharmaceutically acceptable salt" refers to a salt or complex of Chemical Formula 1 or 2, which retains a desired biological activity. Examples of the salt include, but art not limited to, acid addition salts formed with inorganic acids (e.g., hydrochloride, hydrobromide, sulfuric acid, phosphoric acid, nitric acid, etc.), and salts formed with organic acids such as acetic acid, oxalic acid, tartartic acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. The compound may be administered in a form of a pharmaceutically acceptable quaternary salt known to those skilled in the art, as exemplified by, in particular, chloride, bromide, iodide, —O-alkyl, toluenesulfonate, methylsulfonate, sulfonate, phosphate, or carboxylates (e.g., benzoates, succinates, acetates, glycorates, maleates, malates, fumarates, citrates, tartrates, ascorbates, cinnamoates, mandeloate and diphenylacetate). The compound of Chemical. Formula 1 or 2 according to the present disclosure may be provided in any form, including all salts, hydrates, solvates, and prodrugs that can be prepared by methods known in the art, as well as in the form of pharmaceutically acceptable salts thereof.

The acid addition salt according to the present disclosure may be prepared in a typical manner. By way of example, the derivatives of Chemical Formula 1 or 2 are dissolved in an organic solvent such as methanol, ethanol, acetone, dichloromethane, acetonitrile, etc., to which organic acid or inorganic acid is added to induce precipitation. Then, the precipitate is filtered and dried to give the salt. Alternatively, the solvent and the excessive acid are distillated under a reduced pressure and dried, followed by crystallizing the precipitate in an organic solvent to give the salt.

In addition, a pharmaceutically acceptable metal salt can be prepared by using a base. Alkali metal or alkaline earth metal salt is obtained by, for example, dissolving the compound in excessive alkali metal hydroxide or alkaline earth metal hydroxide solution, filtering non-soluble compound salt, evaporating the filtrate, and drying same. In this regard, the metal salt is preferably prepared in the pharmaceutically suitable form of sodium, potassium, or calcium salt. In addition, the corresponding silver salt is prepared by reacting an alkali metal or alkaline earth metal salt with proper silver salt (ex; silver nitrate).

In another aspect, the present disclosure pertains to a composition comprising a compound represented by Chemical Formula 1 or 2 as an active ingredient for prevention or treatment of cancers, narcolepsy, and fasciitis, wherein the compound represented by Chemical Formula 1 or 2 has inhibitory activity against TRIB2 or YAP.

The cancer may be selected from the group consisting of lung cancer, liver cancer, stomach cancer, colorectal cancer, bladder cancer, prostate cancer, breast cancer, ovarian cancer, cervical cancer, thyroid cancer, melanoma, blood cancer, colon cancer, non-small cell lung cancer, pancreatic cancer, skin cancer, head and neck cancer, small bowel cancer, rectal cancer, endometrial cancer, vaginal cancer, testis cancer, esophageal cancer, bile duct cancer, lymph gland cancer, gall bladder cancer, endocrine gland cancer, adrenal cancer, lymphoma, multiple myeloma, thymoma, mesothelioma, kidney cancer, brain cancer, tumors of central nervous system, brainstem glioma, and pituitary adenoma, but with no particular limitations thereto.

Together with a pharmaceutically acceptable carrier typically used, the pharmaceutical composition according to the present disclosure may be formulated into proper dosage forms. As used herein, the term "pharmaceutically acceptable" means physiologically acceptable and, when administered to human beings or animals, generally does not cause allergic responses, such as gastrointestinal disorder and dizziness, or similar reactions thereto. In addition, the composition may be formulated into oral dosage forms, topical agents, suppositories, and sterile injections, such as powders, granules, tablets, capsules, suspensions, emulsions, syrups, aerosols, etc.

Examples of a carrier, an excipient, or a diluent available in the composition include lactose, dextrose, sucrose, sorbitol, mannitol, xylitol, erythritol, maltitol, starch, Arabic gum, alginate, gelatin, calcium phosphate, calcium silicate, cellulose, methyl cellulose, microcrystalline cellulose, polyvinyl pyrrolidone, water, paraoxybenzoate methyl, paraoxybenzoate propyl, talc, magnesium stearate, and mineral oil, but are not limited thereto. For a formulation, a diluent or excipient such as a filler, a stabilizer, a binder, a disintegrant, a surfactant, etc. is typically used. Solid formulations for oral administration include tablets, pills, pulvis, granules, capsules, and so on. Such solid formulations are prepared by mixing the compound of the present disclosure with one or more excipients, for example, starch, microcrystalline cellulose, sucrose or lactose, low-substituted hydroxypropyl cellulose, hypromellose, etc. In addition to the simple excipients, lubricants, such as magnesium stearate, talc, etc., can be used. Liquid formulations for oral administration are suspensions, solutions, emulsions, and syrups, and may contain various excipients, for example, wetting agents, sweeteners, aromatics, and preservatives in addition to generally used simple diluents such as water and liquid paraffin. Formulations for parenteral administration are sterilized aqueous solutions, non-aqueous solvents, suspensions, emulsions, lyophilized preparations and suppositories. As non-aqueous solvents or solvents for suspensions, propylene glycol, polyethylene glycol, vegetable oil like olive oil, injectable ester like ethylolate, etc. may be employed. As a suppository base, witepsol, macrogol, tween 61, cacao butter, lauric butter, glycerol, gelatin, or the like may be used. For a formulation for parenteral administration, each of the indazole derivation compounds of Chemical Formulas 1 and 2 or a pharmaceutically acceptable salt thereof may be sterilized and mixed in water, together with an adjuvant such as a preservative, a stabilizer, a hydrating agent or an emulsifying accelerator, a salt for controlling osmotic pressure, a buffer and the like, and other therapeutically useful substances, to give a solution or suspension, which is then prepared into the unit dosage form such as an ampoule or a vial.

A pharmaceutical composition comprising the compound of each of Chemical Formulas 1 and 2 disclosed herein as an active ingredient may be administered into mammals such as mice, livestock, humans, etc. via various routes. All modes of administration may be considered, and for example, it can be administered by oral, rectal or intravenous, intramuscular, subcutaneous, endometrial or cerebrovascular injection. The dose may vary depending on the age, sex, weight of the subject to be treated, the specific disease or pathological condition to be treated, the severity of the disease or pathological condition, the duration of administration, the route of administration, the absorption, distribution and excretion rate of drug, the types of other drugs used, the judgment of prescriber, and the like. Dose determination based bn such factors is within the standards of those skilled in the art, and the doses generally range from 0.01 mg/kg/day to approximately 2000 mg/kg/day. A more preferred dose is 1 mg/kg/day to 500 mg/kg/day. The composition may be administered once a day or in several divided doses. The dosage does not limit the scope of the present invention in any way.

In addition, the pharmaceutical composition of the present disclosure may be used alone or in combination with surgical operation, hormone therapy, chemotherapy, and a biological response regulator, to prevent or treat cancer, narcolepsy, and fasciitis.

Advantageous Effects of Invention

The present disclosure pertains to a novel indazole derivative and a use thereof. With excellent inhibitory activity against TRIB2 or YAP, the indazole derivative can find advantageous applications in a composition for prevention or treatment of cancer, narcolepsy, and fasciitis.

BRIEF DESCRIPTION OF DRAWINGS

FIG. 1 shows that Compound 17 of the present disclosure decreases the phosphorylation of TRIB2 and YAP proteins in a liver cancer stain (HepG2) in a dose-dependent manner and has an inhibitory activity against YAP even in the ovarian cancer cell line A2780 as assayed for p-YAP.

BEST MODE FOR CARRYING OUT THE INVENTION

Below, a better understanding of the present disclosure may be obtained through the following examples which are set forth to illustrate, but are not to be construed as limiting the present disclosure.

Example 1. Synthesis and Physicochemical Characterization of Indazole Derivative Synthesis procedures and physicochemical properties of compounds 1 to 73 according to the present disclosure are as follows.

Compound 1. tert-butyl-4-(5-(2-fluoropyridin-3-yl)-1H-indazole-3-carboxamido)piperidine-1-carboxylate

[Reaction Scheme 1]

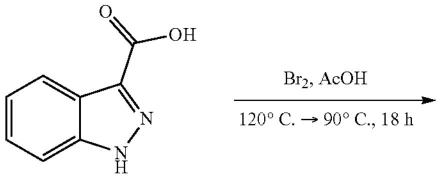

Indazole-3-carboxylic acid

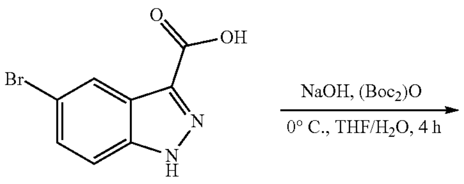

15-246

-continued

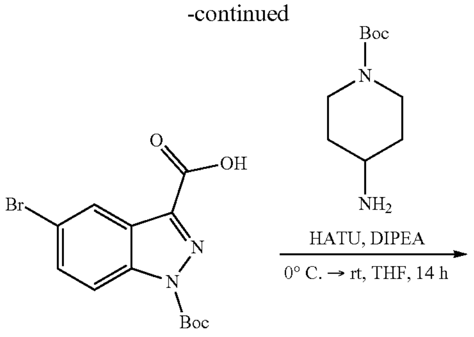

15-276

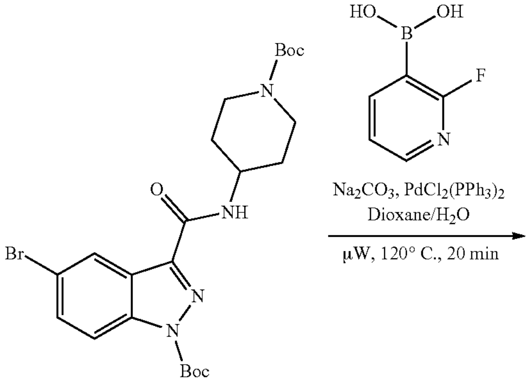

18-083

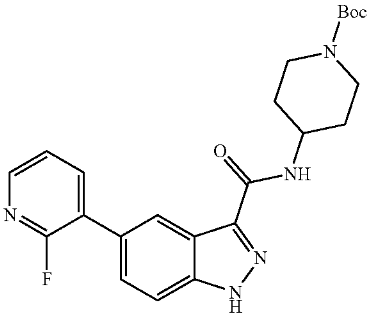

compound 1

1) Synthesis of 5-bromo-1H-indazole-3-carboxylic acid

A suspension of indazole-3-carboxylic acid (500 mg, 3.08 mmol) in AcOH (25 ml) was heated to 120° C. to dissolve the starting material. This material was cooled to 90° C. and mixed with bromine (0.32 ml, 6.16 mmol) before stirring at 90° C. for 18 hours. The reaction mixture was diluted with water (20 ml) and stirred for 1 hour. The solid thus formed in the reaction mixture was filtered and dried by suction to afford 15-246 as a white solid (550 mg, 2.28 mmol, 74%).

1H NMR (300 MHz, DMSO-d6) δ 8.22 (s, 1H), 7.65 (d, J=8.7 Hz, 1H), 7.56 (dd, J=1.8 Hz, 8.8 Hz, 1H); LC/MS 243.2 [M+H+].

2) Synthesis of 1-(tert-butoxycarbonyl)-5-bromo-1H-indazole-3-carboxylic acid To a solution of 15-246 (400 mg, 1.66 mmol) in THF (25 ml) were added NaOH (1.0 M) (3 ml) and then DiBoc at 0° C., and the reaction mixture was stirred at room temperature for 4 hours before being quenched with a 1.5 N HCl aqueous solution. After extraction with EtOAc (150 ml×2), the organic layer was washed with saturated brine. The organic layers thus obtained were pooled and concentrated at a reduced pressure to give a crude mixture. Purification by column chromatography using MeOH/DCM (1:4) as an eluent afforded 15-276 as a white solid (480 mg, 1.41 mmol, 85%).

1H NMR (300 MHz, DMSO-d6) δ 8.29 (d, J=1.5 Hz, 1H), 8.10 (d, J=8.9 Hz, 1H), 7.82 (d, J=1.9 Hz, 8.9 Hz, 1H), 1.67 (s, 9H); LC/MS 338.9 [M−H+].

3) Synthesis of tert-butyl 5-bromo-3-((1-(tert-butoxycarbonyl)piperidin-4-yl)carbamoyl)-1H-indazole-1-carboxylate To a suspension of 15-276 (470 mg, 1.38 mmol) in THE (20 ml) were added DIPEA (0.48 ml, 2.75 mmol) and then HATU (628 mg, 1.65 mmol) at 0° C. The reaction mixture was stirred for 15 minutes, added with tert-butyl 4-aminopiperidine-1-carboxylate (304 mg, 1.52 mmol), and then again stirred for 14 hours at room temperature. When the starting material was completely consumed as monitored by TLC, the reaction mixture was quenched with water. After extraction with EtOAc (2×35 ml), the organic layer was washed with saturated brine. The organic layers thus obtained were pooled and concentrated at a reduced pressure to give a crude mixture. Purification by column chromatography using EtOAc/Hex (2:3) as an eluent afforded 18-083 as a white solid (500 mg, 0.95 mmol, 69%).

1H NMR (300 MHz, CDCl3) δ 8.63 (s, 1H), 7.98 (d, J=8.7 Hz, 1H), 7.66 (d, J=8.7 Hz, 1H), 7.07 (d, J=7.9 Hz, 1H), 4.22-4.08 (m, 3H), 2.93 (t, J=13.0 Hz, 2H), 2.07-2.03 (m, 2H), 1.76 (s, 9H), 1.58-1.54 (m, 2H), 1.49 (s, 9H); LC/MS 521.1 [M−H+].

4) Synthesis of tert-butyl-4-(5-(2-fluoropyridin-3-yl)-1H-indazole-3-carboxamido)piperidine-1-carboxylate To a solution of 0.18-083 in dioxane (2 ml) and $H_2O$ (0.5 ml) were added (2-fluoropyridin-3-yl)boronic acid (32.2 mg, 0.229 mmol) and sodium carbonate (51.8 mg, 0.477 mmol) at room temperature, and the reaction mixture was purged with nitrogen for 10 minutes. The solution was stirred, added with $PdCl_2(PPh_3)_2$ (13.4 mg, 0.019 mmol), and then exposed to microwaves at 120° C. for 20 minutes. After completion of the reaction, the solvent was removed using a rotary evaporator. The resulting crude mixture was diluted in 10 ml of water before extraction with ethyl acetate (2×15 ml). The organic layers thus obtained were pooled, dried over $Na_2SO_4$, and concentrated in a vacuum to give a crude mixture. Purification by column chromatography using EtOAc/hexane as an eluent afforded Compound 1 as a white solid (60 mg, 0.136 mmol, 71%).

1H NMR (300 MHz, CDCl3) δ 11.08 (s, br, 1H), 8.56 (s, 1H), 8.21 (d, J=4.6 Hz, 1H), 7.94 (t, J=7.4 Hz, 1H), 7.68 (d, J=8.7 Hz, 1H), 7.61 (d, J=8.7 Hz, 1H), 7.28 (t, J=6.9 Hz, 1H), 7.00 (d, J=8.1 Hz, 1H), 4.23-4.09 (m, 3H), 2.97 (t, J=11.7 Hz, 2H), 2.09-2.05 (m, 2H), 1.60-1.53 (m, 2H), 1.48 (s, 9H); LC/MS 438.1 [M−H+].

Compound 2. 5-(2-Fluoropyridin-3-yl)-N-(piperidin-4-yl)-1H-indazole-3-carboxamide

[Reaction Scheme 2]

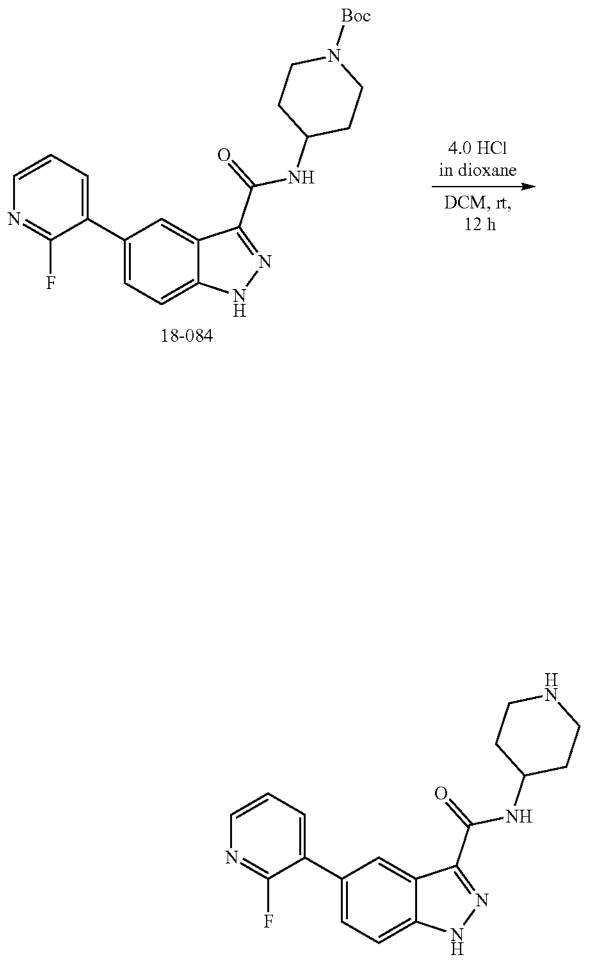

18-084 compound 2

To a solution of 18-084 (40 mg, 0.091 mmol) DCM (15 ml) was added 4.0 M HCl in dioxane (2.0 ml) at 0° C., and the reaction mixture was stirred at room temperature for 12 hours. When the starting material was completely consumed as monitored by TLC, the reaction mixture was quenched with a sodium bicarbonate solution (aq). After extraction with DCM (25 ml×2), the organic layer was washed with saturated brine. The organic layers thus obtained were pooled and concentrated at a reduced pressure to give a crude mixture. Purification by column chromatography using MeOH/DCM as an eluent afforded Compound 2 as a white solid (25 mg, 0.073 mmol, 81%).

1H NMR (300 MHz, CD3OD) δ 8.47 (s, 1H), 8.22 (d, J=5.1 Hz, 1H), 8.20-8.11 (m, 1H), 7.77-7.66 (m, 2H), 7.50-7.44 (m, 1H), 4.33-4.21 (m, 1H), 3.57-3.46 (m, 2H), 3.27-3.14 (m, 2H), 2.27 (dd, J=14.5, 3.8 Hz, 2H), 2.05-1.88 (m, 2H); LC/MS 340.1 [M+H+].

Compound 3. tert-butyl 4-(5-(pyridin-3-yl)-1H-indazole-3-carboxamido)piperidine-1-carboxylate

[Reaction Scheme 3]

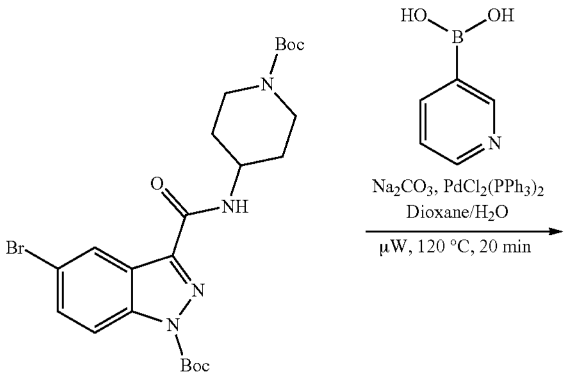

18-083

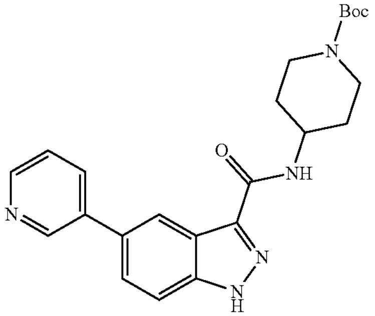

compound 3

To a solution of 18-083 (100 mg, 0.191 mmol) in dioxane (2 ml) and $H_2O$ (0.5 ml) were added (pyridin-3-yl)boronic acid (28.1 mg, 0.229 mmol) and sodium carbonate (51.8 mg, 0.477 mmol) at room temperature, and the reaction mixture was purged with nitrogen for 10 minutes. The solution was stirred and added with $PdCl_2(PPh_3)_2$ (13.4 mg, 0.019 mmol), and the resulting reaction mixture was exposed to microwaves at 120° C. for 20 minutes. After completion of the reaction, the solvent was removed using a rotary evaporator. The resulting crude mixture was diluted in 10 ml of water before extraction with ethyl acetate (2×15 ml). The organic layers thus obtained were pooled, dried over $Na_2SO_4$, and concentrated in a vacuum to give a crude mixture. Purification by column chromatography using EtOAc/hexane as an eluent afforded Compound 3 as a white solid (60 mg, 0.142 mmol, 74%).

1H NMR (300 MHz, CDCl3) δ 11.06 (s, 1H), 8.97 (dd, J=2.4, 0.9 Hz, 1H), 8.68-8.61 (m, 2H), 8.00 (dt, J=8.0, 2.0 Hz, 1H), 7.74-7.61 (m, 2H), 7.41 (ddd, J=8.0, 4.8, 0.9 Hz, 1H), 7.04 (d, J=8.1 Hz, 1H), 4.34-4.02 (m, 3H), 2.99 (t, J=12.5 Hz, 2H), 2.10 (d, J=13.9 Hz, 2H), 1.59 (dd, J=12.0, 4.1 Hz, 2H), 1.51 (s, 9H); LC/MS 420.1 [M−H+].

Compound 4. N-(Piperidin-4-yl)-5-(pyridin-3-yl)-1H-indazole-3-carboxamide

[Reaction Scheme 4]

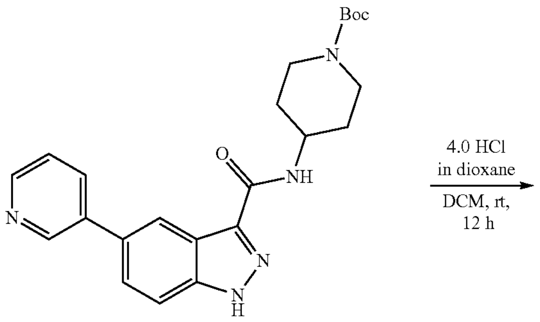

18-085

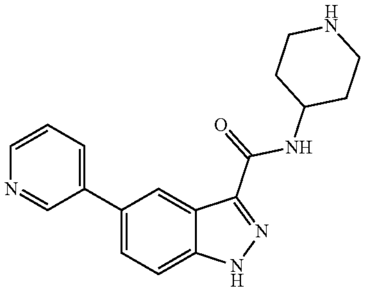

compound 4

To a solution of 18-085 (40 mg, 0.095 mmol) in DCM (15 ml) was added 4.0 M HCl in dioxane (2.0 ml) at 0° C., and the reaction mixture was stirred at room temperature for 12 hours. When the starting material was completely consumed as monitored by TLC, the reaction mixture was quenched with an aqueous sodium bicarbonate solution. After extraction with DCM (25 ml×2), the organic layer was washed with saturated brine. The organic layers thus obtained were pooled and concentrated at a reduced pressure to give a crude mixture. Purification by column chromatography using MeOH/DCM as an eluent afforded Compound 4 as a white solid (25 mg, 0.077 mmol, 82%).

1H NMR (300 MHz, CD3OD) S 9.27 (s, 1H), 9.03 (d, J=8.1 Hz, 1H), 8.87 (d, J=5.8 Hz, 1H), 8.70 (s, 1H), 8.23 (dd, J=8.3, 5.7 Hz, 1H), 7.95-7.82 (m, 2H), 4.35-4.27 (m, 1H), 3.57-3.49 (m, 2H), 3.28-3.17 (m, 2H), 2.31-2.22 (m, 2H), 2.07-1.92 (m, 2H); LC/MS 322.1 [M+H+].

Compound 5. tert-butyl 4-(5-(2-fluorophenyl)-1H-indazole-3-carboxamido) piperidine-1-carboxylate

[Reaction Scheme 5]

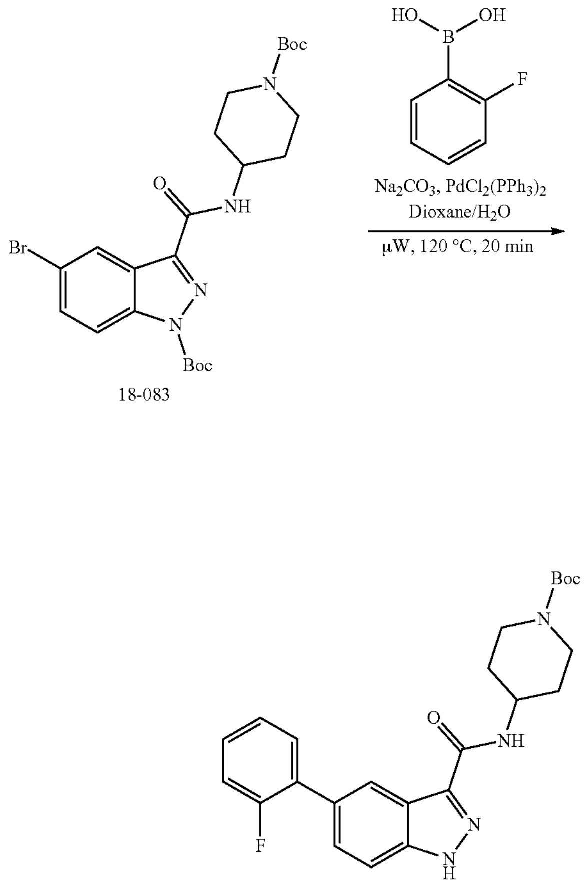

18-083 compound 5

To a solution of 18-083 (100 mg, 0.191 mmol) in dioxane (2 ml) and $H_2O$ (0.5 ml) were added (2-fluorophenyl) boronic acid (32.0 mg, 0.229 mmol) and sodium carbonate (51.8 mg, 0.477 mmol) at room temperature, and the reaction mixture was purged with nitrogen for 10 minutes. The solution was stirred and added with $PdCl_2(PPh_3)_2$ (13.4 mg, 0.019 mmol), and the resulting reaction mixture was exposed to microwaves at 120° C. for 20 minutes. After completion of the reaction, the solvent was removed using a rotary evaporator. The resulting crude mixture was diluted in 10 ml of water before extraction with ethyl acetate (2×15 ml). The organic layers thus obtained were pooled, dried over $Na_2SO_4$, and concentrated in a vacuum to give a crude mixture. Purification by column chromatography using EtOAc/hexane as an eluent afforded Compound 5 as a white solid (70 mg, 0.159 mmol, 83%).

1H NMR (300 MHz, CDCl3) δ 10.65 (s, 1H), 8.58 (s, 1H), 7.69 (dt, J=8.8, 1.9 Hz, 1H), 7.59 (dd, J=8.8, 0.9 Hz, 1H), 7.56-7.50 (m, 1H), 7.37-7.31 (m, 1H), 7.25 (dd, J=7.5, 1.3 Hz, 1H), 7.21-7.14 (m, 1H), 7.00 (d, J=8.1 Hz, 1H), 4.31-4.05 (m, 3H), 2.98 (t, J=12.6 Hz, 2H), 2.09 (d, J=11.2 Hz, 2H), 1.58 (d, J=11.8 Hz, 2H), 1.50 (s, 9H); LC/MS 437.1 [M−H+].

Compound 6. 5-(2-Fluorophenyl)-N-(piperidin-4-yl)-1H-indazole-3-carboxamide

[Reaction Scheme 6]

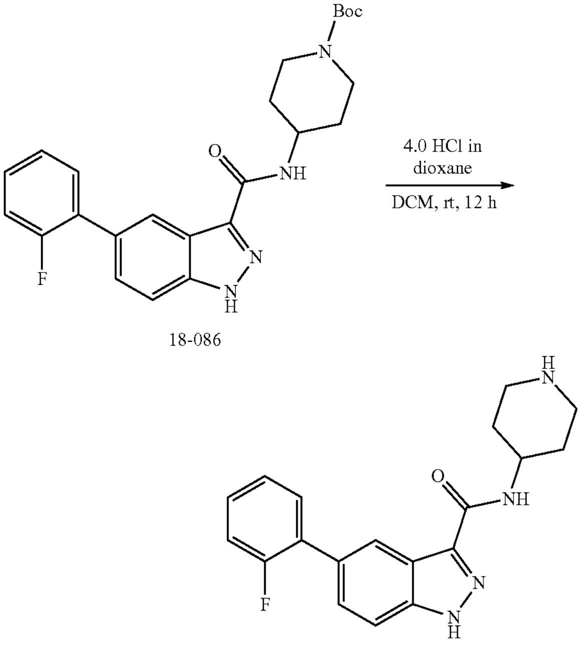

18-086 compound 6

To a solution of 18-086 (40 mg, 0.091 mmol) in DCM (15 ml) was added 4.0 M HCl in dioxane (2.0 ml) at 0° C., and the reaction mixture was stirred at room temperature for 12 hours. When the starting, material was completely consumed as monitored by TLC, the reaction mixture was quenched with an aqueous sodium bicarbonate solution. After extraction with DCM (25 ml×2), the organic layer was washed with saturated brine. The organic layers thus obtained were pooled and concentrated at a reduced pressure to give a crude mixture. Purification by column chromatography using MeOH/DCM as an eluent afforded Compound 6 as a white solid (26 mg, 0.077 mmol, 84%).

1H NMR (300 MHz, CD3OD) δ 8.40 (s, 1H), 7.72-7.65 (m, 2H), 7.61-7.53 (m, 1H), 7.43-7.36 (m, 1H), 7.32-7.29 (m, 1H), 7.27-7.19 (m, 1H), 4.33-4.21 (m, 1H), 3.51 (d, J=13.2 Hz, 2H), 3.26-3.16 (m, 2H), 2.30-2.24 (m, 2H), 2.03-1.88 (m, 2H); LC/MS 339.1 [M+H+].

Compound 7. 5-(2-Fluoropyridin-3-yl)-N-(piperidin-4-yl)-1H-pyrrolo[2,3-b]pyridine-3-carboxamide

[Reaction Scheme 7]

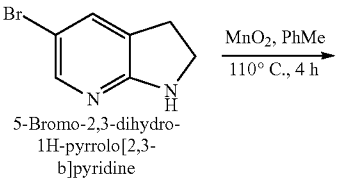

5-Bromo-2,3-dihydro-1H-pyrrolo[2,3-b]pyridine

-continued

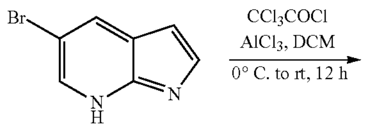

18-097

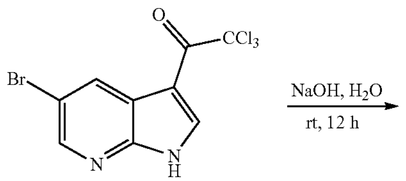

18-098

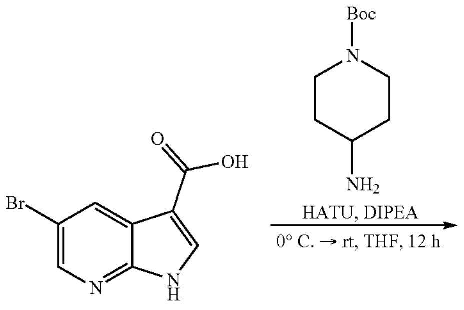

18-101

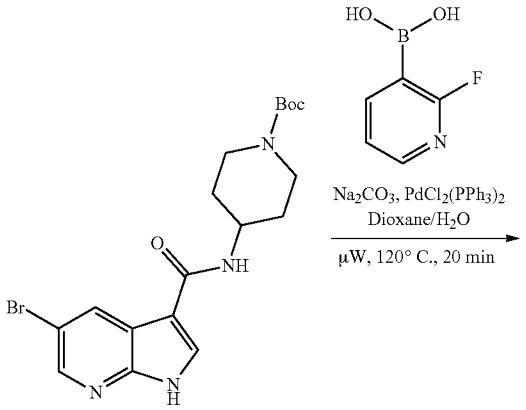

18-103

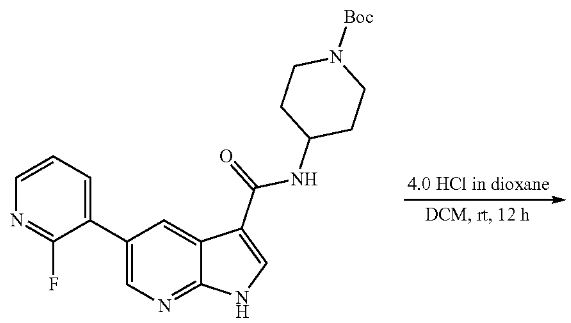

18-104

-continued

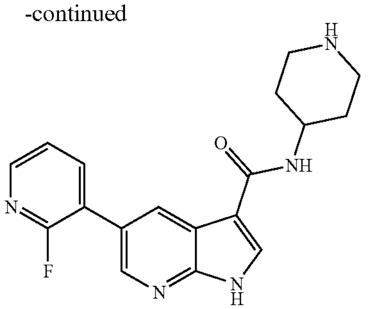

compound 7

1) Synthesis of 5-bromo-7H-pyrrolo[2,3-b]pyridine

A solution of manganese dioxide (873 mg, 10.0 mmol) in 5-bromo-2,3-dihydro-1H-pyrrolo[2,3-b]pyridine (500 mg, 2.51 mmol) and toluene (10 ml) was stirred at 110° C. for 4 hours. The reaction mixture was cooled to room temperature and filtered. The solid thus obtained was washed with DCM. The filtrate and the washing solution were combined and concentrated at a reduced pressure. The residue was subjected to purification by silica gel column chromatography to afford the title compound 18-097 as a brown solid (350 mg, 1.77 mmol, 70%).

1H NMR (300 MHz, DMSO-d6) δ 11.89 (s, 1H), 8.26 (d, J=2.2 Hz, 1H), 8.20 (d, J=2.2 Hz, 1H), 7.55 (d, J=3.4 Hz, 1H), 6.45 (d, J=3.4 Hz, 1H); LC/MS 198.2 [M+H+].

2) Synthesis of 1-(5-bromo-1H-pyrrolo[2,3-b]pyridin-3-yl)-2,2,2-trichloroethan-1-one To a solution of 18-097 (350 mg, 1.77 mmol) in dry DCM (10 ml) was added $AlCl_3$ (590 mg, 4.42 mmol) at 0° C. in a nitrogen atmosphere. After 10 minutes, trichloroacetyl chloride (387 mg, 2.13 mmol) was dropwise added, and the resulting mixture was stirred at room temperature for 12 hours. When the reaction was completed as monitored by TLC, the reaction quenched with cold water (20 ml), followed by extraction with DCM (3×10 ml). The organic layer thus formed was dried ($MgSO_4$) and concentrated in a vacuum to afford 18-098 as a white solid (400 mg, 1.16 mmol, 66%).

1H NMR (300 MHz, CDCl3) δ 11.46 (s, 1H), 8.94 (d, J=2.1 Hz, 1H), 8.55 (d, J=2.1 Hz, 1H), 8.53 (s, 1H); LC/MS 341.1 [M+H+].

3) Synthesis of 5-bromo-1H-pyrrolo[2,3-b]pyridine-3-carboxylic acid

At room temperature, 18-098 (400 mg, 1.16 mmol) was treated with an aqueous NaOH solution (15 ml) for 12 hours while stirring. The resulting mixture was adjusted to have a pH of 4-6 by adding drops of conc. HCl at 0° C. The precipitate thus formed was filtered, washed with water and hexane, and dried in a vacuum. Purification through column chromatography afforded 18-101 as a white solid (250 mg, 1.03 mmol, 89%).

1H NMR (300 MHz, DMSO-d6) δ 12.67 (s, 1H), 12.42 (s, 1H), 8.42 (d, J=2.3 Hz, 1H), 8.40 (d, J=2.3 Hz, 1H), 8.22 (s, 1H); LC/MS 241.2 [M+H+].

4) Synthesis of tert-butyl 4-(5-bromo-1H-pyrrolo[2,3-b]pyridine-3-carboxamido)piperidine-1-carboxylate To a suspension of 18-101 (100 mg, 0.414 mmol) in THE (20 ml) were added DIPEA (107 mg, 0.828 mmol) and then HATU (188 mg, 0.496 mmol) at 0° C., and the reaction mixture was stirred for 15 minutes. After addition of tert-butyl 4-aminopiperidine-1-carboxylate (91 mg, 0.456 mmol), the reaction mixture was stirred at room temperature for 14 hours. When the starting material was completely consumed as monitored by TLC, the reaction mixture was quenched with water. After extraction with EtOAc (2×35 ml), the organic layer was washed with saturated brine. The organic layers thus obtained were pooled and concentrated at a reduced pressure to give a crude mixture. Purification by column chromatography using EtOAc/Hex (2:3) as an eluent afforded 18-103 as a white solid (120 mg, 0.283 mmol, 68%).

1H NMR (300 MHz, DMSO-d6) δ 12.34 (s, 1H), 8.57 (d, J=2.3 Hz, 1H), 8.35 (d, J=2.3 Hz, 1H), 8.23 (s, 1H), 7.90 (d, J=7.8 Hz, 1H), 3.97-3.92 (m, 3H), 2.87 (s, 2H), 1.82 (d, J=9.7 Hz, 2H), 1.42 (s, 11H); LC/MS 423.2 [M+H+].

5) Synthesis of tert-butyl-4-(5-(2-fluoropyridin-3-yl)-1H-pyrrolo[2,3-b]pyridine-3-carboxamido)-piperidine-1-carboxylate To a solution of 18-103 (100 mg, 0.236 mmol) in dioxane (2 ml) and $H_2O$ (0.5 ml) were added (2-fluoropyridin-3-yl) boronic acid (40 mg, 0.283 mmol) and sodium carbonate (64 mg, 0.590 mmol) at room temperature, and the reaction mixture was purged with nitrogen for 10 minutes. The solution was stirred and added with $PdCl_2(PPh_3)_2$ (16 mg, 0.023 mmol), and the resulting reaction mixture was exposed to microwaves at 120° C. for 20 minutes. After completion of the reaction, the solvent was removed using a rotary evaporator. The resulting crude mixture was diluted in 10 ml of water before extraction with ethyl acetate (2×15 ml). The organic layers thus obtained were pooled, dried over $Na_2SO_4$, and concentrated in a vacuum to give a crude mixture. Purification by HPLC afforded 18-104 as a white solid (30 mg, 0.068 mmol, 29%).

1H NMR (300 MHz, CDCl3) δ 10.99 (s, 1H), 8.66 (s, 1H), 8.61 (t, J=2.0 Hz, 1H), 8.27 (d, J=4.7 Hz, 1H), 8.07-7.94 (m, 1H), 7.89 (d, J=2.2 Hz, 1H), 7.40-7.32 (m, 1H), 592 (d, J=7.9 Hz, 1H), 4.30-4.02 (m, 3H), 2.95 (t, J=12.3 Hz, 2H), 2.09 (d, J=12.5 Hz, 2H), 1.49 (s, 9H), 1.48-1.46 (m, 2H); LC/MS 440.2 [M+H+].

6) Synthesis of 5-(2-fluoropyridin-3-yl)-N-(piperidin-4-yl)-1H-pyrrolo[2,3-b]pyridine-3-carboxamide To a, solution of 18-104 (30 mg, 0.068 mmol) in DCM (15 ml) was added 4.0 M HCl in dioxane (2.0 ml) at 0° C., and the reaction mixture was stirred at room temperature for 12 hours. When the starting material was completely consumed as monitored by TLC, the reaction mixture was quenched with an aqueous sodium bicarbonate solution. After extraction with DCM (25 ml×2), the organic layer was washed with saturated brine. The organic layers thus obtained were pooled and concentrated at a reduced pressure to give a crude mixture. Purification by column chromatography using MeOH/DCM afforded Compound 7 as a white solid (20 mg, 0.058 mmol, 86%).

1H NMR (300 MHz, CD3OD) S 9.32 (s, 1H), 8.82 (s, 1H), 8.52 (s, 1H), 8.36 (d, J=4.9 Hz, 1H), 8.29 (ddd, J=9.6, 7.5, 1.8 Hz, 1H), 7.56 (ddd, J=6.8, 4.9, 1.7 Hz, 1H), 4.31-4.18 (m, 1H), 3.53 (d, J=13.0 Hz, 2H), 3.26-3.12 (m, 2H), 2.26 (d, J=11.8 Hz, 2H), 2.06-1.86 (m, 2H); LC/MS 340.1 [M+H+].

Compound 8. 5-(2-Fluoropyridin-3-yl)-N-(piperidin-4-yl)-1H-indole-3-carboxamide

[Reaction Scheme 8]

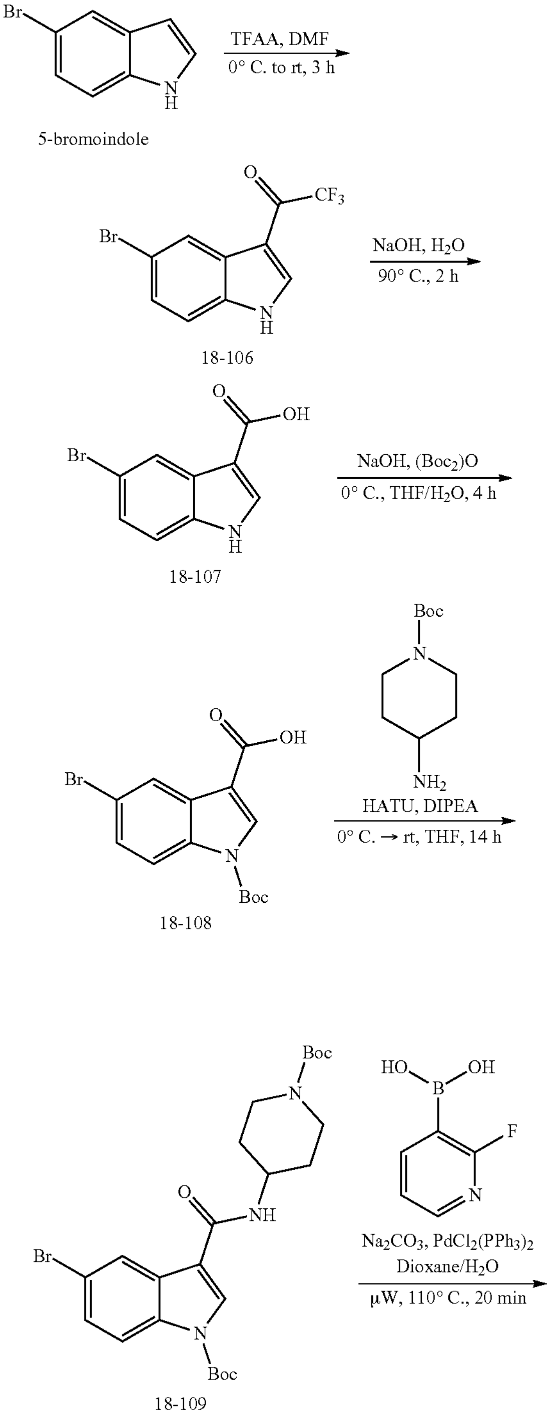

5-bromoindole 18-106

18-107

18-108

18-109

-continued

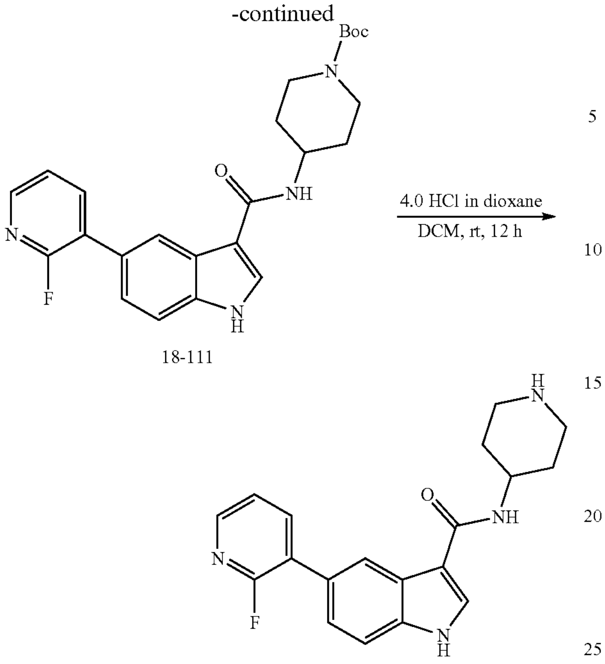

18-111

Compound 8

1) Synthesis of 1-(5-bromo-1H-indol-3-yl)-2,2,2-trifluoroethan-1-one

In a dry flask, 5-bromoindole (500 mg, 2.55 mmol) was dissolved in dry DMF (5.0 ml) under an argon atmosphere. This solution was cooled to 0° C. and added with drops of trifluoroacetic anhydride (0.5 ml, 3.82 mmol). The mixture was stirred at 0° C. for 3 hours and then quenched with water. From the crude mixture, a solid was obtained by filtration. The solid was washed twice with water and dissolved in ethyl acetate. The organic layer was washed with an aqueous $NaHCO_3$ solution and brine and dried over anhydrous $MgSO_4$, followed by evaporation in a vacuum to afford 18-106 as a white solid (600 mg, 2.05 mmol, 80%).

1H NMR (300 MHz, CDCl3) δ 8.98 (s, 1H), 8.61 (s, 1H), 8.09 (d, J=1.7 Hz, 1H), 7.51 (dd, J=8.7, 1.9 Hz, 1H), 7.38 (d, J=8.8 Hz, 1H); LC/MS 293.2 [M+H+].

2) Synthesis of 5-bromo-1H-indole-3-carboxylic acid

A solution of 18-106 (600 mg, 2.05 mmol) in 20% NaOH solution (15 ml) was heated at 90° C. for 2 hours. The resulting mixture was adjusted to have a pH of 4-6 by adding drops of conc. HCl at 0° C. The precipitate thus formed was filtered, washed with water and hexane, and dried in a vacuum. Purification through column chromatography afforded 18-107 as a pale yellowish solid (420 mg, 1.75 mmol, 85%).

1H NMR (300 MHz, DMSO-d6) δ 12.14 (s, 1H), 12.01 (s, 1H), 8.13 (d, J=1.8 Hz, 1H), 8.05 (s, 1H), 7.45 (d, J=8.6 Hz, 1H), 7.32 (dd, J=8.6, 2.0 Hz, 1H); LC/MS 240.2 [M+H+].

3) Synthesis of 1-(tert-butoxycarbonyl)-5-bromo-1H-indazole-3-carboxylic acid To a solution of 18-107 (400 mg, 1.66 mmol) in THF (25 ml) were added NaOH (1.0 M) (5 ml) and then $(Boc)_2O$ (400 mg, 1.83 mmol) at 0° C. The reaction mixture was stirred at room temperature for 4 hours and then quenched with 1.5 N HCl (aq). After extraction with EtOAc (150 ml×2), the organic layer was washed with saturated brine. The organic layers thus obtained were pooled and concentrated at a reduced pressure to give a crude mixture. Purification by column chromatography using MeOH/DCM (1:4) as an eluent afforded 18-108 as a white solid (500 mg, 1.46 mmol, 88%).

1H NMR (300 MHz, DMSO-d6) δ 12.97 (s, 1H), 8.20 (d, J=1.9 Hz, 2H), 8.05 (d, J=8.9 Hz, 1H), 7.56 (dd, J=8.9, 2.0 Hz, 1H), 1.65 (s, 9H); LC/MS 338.9 [M−H+].

4) Synthesis of tert-butyl 5-bromo-3-((1-(tert-butoxycarbonyl)piperidin-4-yl)carbamoyl)-1H-indole-1-carboxylate To a suspension of 18-108 (200 mg, 0.587 mmol) THF (20 ml) were added DIPEA (151 mg, 1.17 mmol) and then HATU (267 mg, 0.704 mmol) at 0° C., and the reaction mixture was stirred for 15 minutes. After addition of tert-butyl 4-aminopiperidine-1-carboxylate (129 mg, 0.646 mmol), the reaction mixture was stirred at room temperature for 14 hours. When the starting material was completely consumed as monitored by TLC, the reaction mixture was quenched with water. After extraction with EtOAc (2×35 ml), the organic layer was washed with saturated brine. The organic layers thus obtained were pooled and concentrated at a reduced pressure to give a crude mixture. Purification by column chromatography using EtOAc/Hex (2:3) as an eluent afforded 18-109 as a white solid (266 mg, 0.509 mmol, 87%).

1H NMR (300 MHz, CDCl3) δ 8.23 (d, J=1.8 Hz, 1H), 8.04 (d, J=8.9 Hz, 1H), 8.00 (s, 1H), 7.48 (dd, J=8.9, 1.9 Hz, 1H), 5.82 (d, J=6.2 Hz, 1H), 4.33-4.03 (m, 3H), 2.94 (t, J=12.5 Hz, 2H), 2.08 (d, J=9.4 Hz, 2H), 1.70 (s, 9H), 1.49 (s, 9H), 1.45-1.41 (m, 2H); LC/MS 520.2 [M−H+].

5) Synthesis of tert-butyl-4-(5-(2-fluoropyridin-3-yl)-1H-indole-3-carboxamido)piperidine-1-carboxylate To a solution of 18-109 (100 mg, 0.191 mmol) in dioxane (2 ml) and $H_2O$ (0.5 ml) were added (2-fluoropyridin-3-yl) boronic acid (32 mg, 0.229 mmol) and sodium carbonate (52 mg, 0.477 mmol) at room temperature, and the reaction mixture was purged with nitrogen for 10 minutes. The solution was stirred and added with $PdCl_2(PPh_3)_2$ (13 mg, 0.019 mmol) before exposure to microwaves at 110° C. for 20 minutes. After completion of the reaction, the solvent was removed using a rotary evaporator. The resulting crude mixture was diluted in 10 ml of water before extraction with ethyl acetate (2×15 ml). The organic layers thus obtained were pooled, dried over $Na_2SO_4$, and concentrated in a vacuum to give a crude mixture. Purification through HPLC afforded 18-111 as a white solid (60 mg, 0.136 mmol, 71%).

1H NMR (300 MHz, CDCl3) δ 9.51 (s, 1H), 8.23 (s, 1H), 8.19 (d, J=4.5 Hz, 1H), 7.94 (t, J=8.7 Hz, 1H), 7.76 (d, J=2.7 Hz, 1H), 7.54-7.48 (m, 2H), 7.27 (s, 1H), 5.97 (d, J=7.6 Hz, 1H), 4.33-4.04 (m, 3H), 2.94 (t, J=12.0 Hz, 2H), 2.07 (s, 2H), 1.49 (s, 11H); LC/MS 439.2 [M+H+].

6) Synthesis of 5-(2-fluoropyridin-3-yl)-N-(piperidin-4-yl)-1H-indole-3-carboxamide To a solution of 18-111 (60 mg, 0.136 mmol) in DCM (15 ml) was added 4.0 M HCl in dioxane (2.0 ml) at 0° C., and the reaction mixture was stirred at room temperature for 12 hours. When the starting material was completely consumed as monitored by TLC, the reaction mixture was quenched with a sodium bicarbonate solution (aq). After extraction with DCM (25 ml×2), the organic layer was washed with saturated brine. The organic layers thus obtained were pooled and concentrated at a reduced pressure to give a crude mixture. Purification by column chromatography using MeOH/DCM as an eluent afforded Compound 8 as a white solid (40 mg, 0.118 mmol, 86%).

1H NMR (300 MHz, CD3OD) δ 8.26 (s, 1H), 8.03 (dd, J=5.6, 4.0 Hz, 1H), 7.99 (s, 1H), 7.53 (dd, J=12.2, 7.2 Hz, 1H), 7.45 (d, J=8.5 Hz, 1H), 7.37-7.25 (m, 2H), 4.16-4.03 (m, 1H), 3.39 (d, J=13.0 Hz, 2H), 3.12-2.97 (m, 2H), 2.12 (d, J=11.6 Hz, 2H), 1.93-1.73 (m, 2H); LC/MS 339.1 [M+H+].

Compound 9. 5-(2-Fluoropyridin-3-yl)-1-methyl-N-(piperidin-4-yl)-1H-indazole-3-carboxamide

[Reaction Scheme 9]

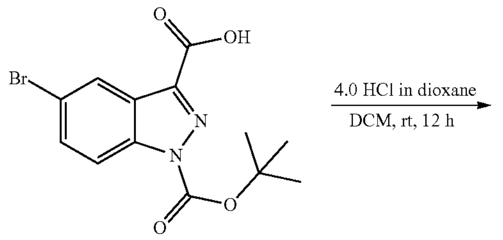

15-330

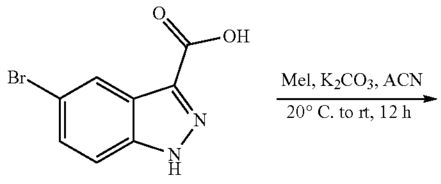

18-102

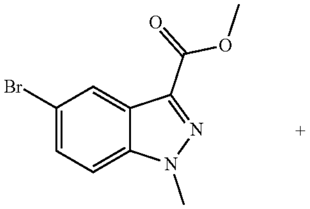

18-105-1

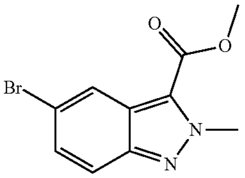

18-105-2

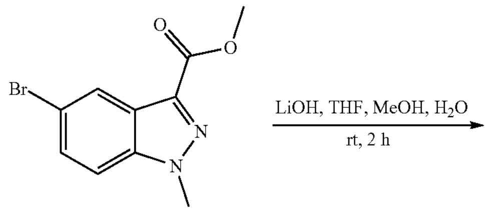

18-105-1

-continued

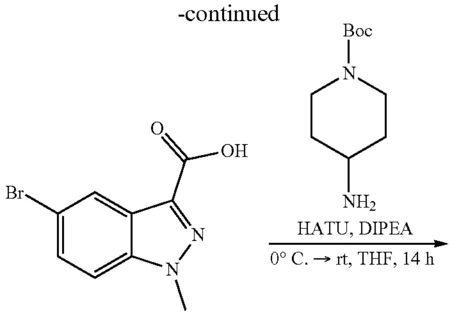

18-113

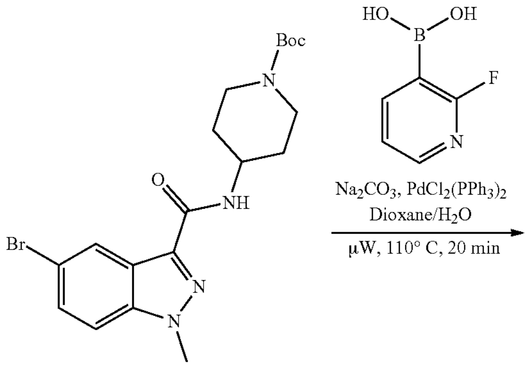

18-115

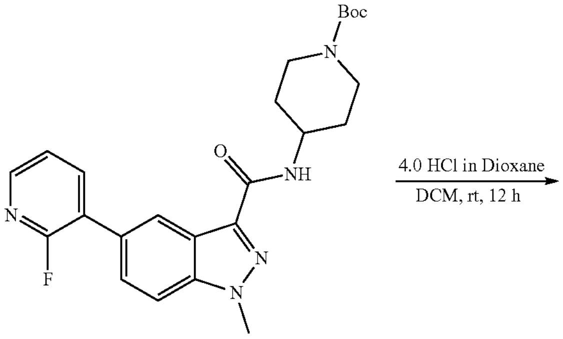

18-119

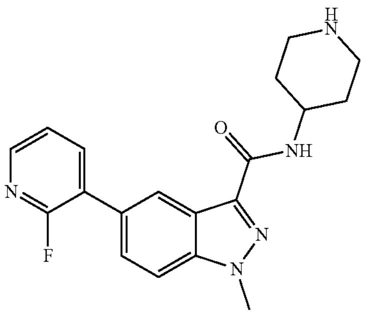

Compound 9

1) Synthesis of 5-bromo-1H-indazole-3-carboxylic acid

To a solution of 15-330 (250 mg, 0.732 mmol) in DCM (15 ml) was added 4.0 M HCl in dioxane (2.0 ml) at 0° C., and the reaction mixture was stirred at room temperature for 12 hours. When the starting material was completely consumed as monitored by TLC, the reaction mixture was concentrated at a reduced pressure to afford 18-102 as a white solid (160 mg, 0.66 mmol, 90%).

1H NMR (300 MHz, DMSO-d6) δ 14.01 (s, 1H), 13.14 (s, 1H), 8.22 (s, 1H), 7.66 (d, J=8.9 Hz, 1H), 7.57 (dd, J=8.8, 1.8 Hz, 1H); LC/MS 240.2 [M+H+].

2) Synthesis of Methyl 5-bromo-1-methyl-1H-indazole-3-carboxylate

To a solution of 18-102 (160 mg, 0.663 mmol) in acetonitrile (20 ml) were added potassium carbonate (458 mg, 3.31 mmol) and methyl iodide (0.2 ml, 3.31 mmol) at 20° C. The mixture was stirred at −20° C. for 10 hours in a nitrogen atmosphere. The mixture was concentrated in a vacuum. The crude residue was subjected to purification by silica gel column chromatography (Hex/EtOAc=10/1 to 5/1) to afford 18-105-1 as a white solid (100 mg, 0.371 mmol, 56%) and 18-105-2 as a white solid (100 mg).

18-105-1: 1H NMR (300 MHz, CDCl3) δ 8.39 (d, J=1.6 Hz, 0.2H), 8.20 (d, J=1.2 Hz, 1H), 7.75 (d, J=1.6 Hz, 0.2H), 7.67 (d, J=9.1 Hz, 1H), 7.44 (dd, J=9.1, 1.8 Hz, 1H), 4.55-4.50 (m, 4H), 4.07 (s, 3H); LC/MS 270.9 [M+H+].

18-105-2: 1H NMR (300 MHz, CDCl3) δ 8.41 (d, J=1.2 Hz, 1H), 7.56 (dd, J=8.9, 1.8 Hz, 1H), 7.37 (d, J=8.9 Hz, 1H), 4.18 (s, 3H), 4.06 (s, 3H); LC/MS 270.9 [M+H+].

3) Synthesis of 5-bromo-1-methyl-1H-indazole-3-carboxylic acid

To a solution of 18-105-1 (100 mg, 0.371 mmol) in THE (4 ml), MeOH (2 ml), and $H_2O$ (1 ml) was added lithium hydroxide monohydrate (31 mg, 0.743 mmol) at room temperature, and the reaction mixture was stirred at room temperature for 2 hours. When the starting material was completely consumed as monitored by TLC, the reaction mixture was concentrated by removing the solvents THF, methanol, and water to afford 18-113 as a white solid (80 mg, 0.313 mmol, 84%).

1H NMR (300 MHz, DMSO-d6) δ 8.38 (d, J=1.9 Hz, 1H), 7.49 (d, J=9.0 Hz, 1H), 7.25 (dd, J=9.0, 2.0 Hz, 1H), 4.41 (s, 3H); LC/MS 255.2 [M+H+].

4) Synthesis of tert-butyl 4-(5-bromo-1-methyl-1H-indazole-3-carboxamido)piperidine-1-carboxylate To a suspension of 18-113 (80 mg, 0.313 mmol) in DMF (10 ml) were added DIPEA (0.11 ml, 0.626 mmol) and then HATU (142 mg, 0.375 mmol) at 0° C., and the reaction mixture was stirred for 15 minutes. After addition of tert-butyl 4-aminopiperidine-1-carboxylate (69 mg, 0.345 mmol), the reaction mixture was stirred at room temperature for 14 hours. When the starting material was completely consumed as monitored by TLC, the reaction mixture was quenched with water. After extraction with EtOAc (2×35 ml), the organic layer was washed with saturated brine. The organic layers thus obtained were pooled and concentrated at a reduced pressure to give a crude mixture. Purification by column chromatography using EtOAc/Hex (2:3) as an eluent afforded 18-115 as a white solid (90 mg, 0.205 mmol, 65%).

1H NMR (300 MHz, CDCl3) δ 7.76 (d, J=1.3 Hz, 1H), 7.65 (d, J=9.1 Hz, 1H), 7.40 (dd, J=9.1, 1.5 Hz, 1H), 6.12 (d, J=7.7 Hz, 1H), 4.44 (s, 3H), 4.27-4.13 (m, 3H), 3.01-2.91 (m, 2H), 2.17-2.08 (m, 2H), 1.57 (td, J=12.1, 4.3 Hz, 2H), 1.49 (s, 9H); LC/MS 435.2 [M−H+].

5) Synthesis of tert-butyl 4-(5-(2-fluoropyridin-3-yl)-1-methyl-1H-indazole-3-carboxamido)piperidine-1-carboxylate To a solution of 18-115 (80 mg, 0.182 mmol) in dioxane (2 ml) and $H_2O$ (0.5 ml) were added (2-fluoropyridin-3-yl) boronic acid (31 mg, 0.219 mmol) and sodium carbonate (49 mg, 0.455 mmol) at room temperature, and the reaction mixture was purged with nitrogen for 10 minutes. The solution was stirred and added with $PdCl_2(PPh_3)_2$ (12 mg, 0.018 mmol) before exposure to microwaves at 110° C. for 20 minutes. After completion of the reaction, the solvent was removed using a rotary evaporator. The resulting crude mixture was diluted in 10 ml of water before extraction with ethyl acetate (2×15 ml). The organic layers thus obtained were pooled, dried over $Na_2SO_4$, and concentrated in a vacuum to give a crude mixture. Purification by column chromatography using EtOAc/Hex (2:3) as an eluent afforded 18-119 (40 mg, 0.088 mmol, 48%).

1H NMR (300 MHz, CDCl3) δ 8.25 (d, J=4.8 Hz, 1H), 8.01-7.91 (m, 1H), 7.87 (s, 1H), 7.73-7.66 (m, 1H), 7.57-7.49 (m, 2H), 7.41-7.32 (m, 1H), 6.12 (d, J=7.9 Hz, 1H), 4.51 (s, 3H), 4.30-4.11 (m, 3H), 2.98 (t, J=12.1 Hz, 2H), 2.14 (d, J=9.7 Hz, 2H), 1.61-1.52 (m, 2H), 1.49 (s, 9H); LC/MS 454.2 [M+H+].

6) Synthesis of 5-(2-fluoropyridin-3-yl)-1-methyl-N-(piperidin-4-yl)-1H-indazole-3-carboxamide To a solution of 18-119 (40 mg, 0.088 mmol) in DCM (15 ml) was added 4.0 M HCl in dioxane (2.0 ml) at 0° C., and the reaction mixture was stirred at room temperature for 12 hours. When the starting material was completely consumed as monitored by TLC, the reaction mixture was quenched with a sodium bicarbonate solution (aq). After extraction with DCM (25 ml×2), the organic layer was washed with saturated brine. The organic layers thus obtained were pooled and concentrated at a reduced pressure to give a crude mixture. Purification by column chromatography using MeOH/DCM (2:3) as an eluent afforded Compound 9 as a white solid (28 mg, 0.079 mmol, 90%).

1H NMR (300 MHz, CD3OD) δ 8.25-8.14 (m, 2H), 8.02 (s, 1H), 7.81 (d, J=9.0 Hz, 1H), 7.65-7.59 (m, 1H), 7.52-7.43 (m, 1H), 4.40 (s, 3H), 4.33-4.25 (m, 1H), 3.52 (d, J=13.0 Hz, 2H), 3.28-3.15 (m, 2H), 2.34 (d, J=11.4 Hz, 2H), 2.06-1.87 (m, 2H); LC/MS 354.2 [M+H+].

Compound 10. 1-Benzoyl-N-(1-benzoylpiperidin-4-yl)-5-(2-fluoropyridin-3-yl)-1H-indazole-3-carboxamide

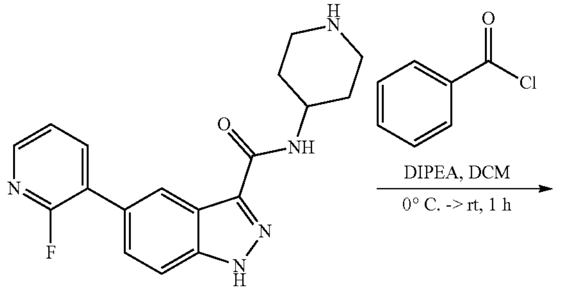

18-138

-continued

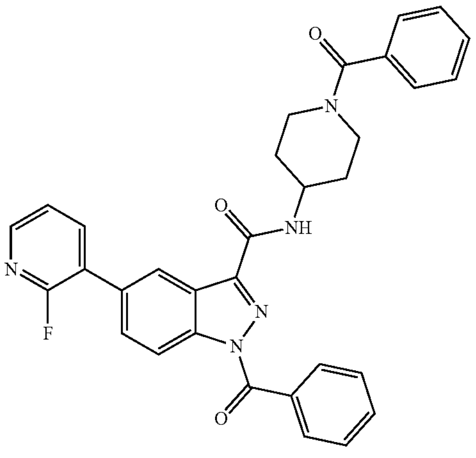

Compound 10

To a suspension of 18-138 (10 mg, 0.029 mmol) in DCM (2.0 ml) were added DIPEA (7.5 mg, 0.058 mmol) and then benzoyl chloride (4.5 mg, 0.032 mmol) at 0° C., and the reaction mixture was stirred for 1 hour. When the starting material was completely consumed as monitored by TLC, the reaction mixture was quenched with water. After extraction with EtOAc (2×35 ml), the organic layer was washed with saturated brine. The organic layers thus obtained were pooled and concentrated at a reduced pressure to give a crude mixture. Purification by column chromatography using EtOAc/Hex (2:3) as an eluent afforded Compound 10 as a white solid (8.0 mg, 0.014 mmol, 50%).

1H NMR (300 MHz, CDCl3) δ 8.66 (s, 1H), 8.62 (d, J=8.8 Hz, 1H), 8.28 (d, J=4.9 Hz, 1H), 8.11-7.98 (m, 3H), 7.91 (dd, J=8.8, 1.8 Hz, 1H), 7.72 (t, J=7.4 Hz, 1H), 7.61 (t, J=7.5 Hz, 2H), 7.43 (s, 5H), 7.35 (ddd, J=6.8, 4.8, 1.6 Hz, 1H), 6.87 (d, J=8.0 Hz, 1H), 4.81-4.64 (m, 1H), 4.37-4.25 (m, 1H), 3.94-3.75 (m, 1H), 3.30-3.01 (m, 2H), 2.26-2.07 (m, 2H), 1.59-1.40 (m, 2H); LC/MS 548.2 [M+H+].

Compound 11. 1-(Cyclopropanecarbonyl)-N-(1-(cyclopropanecarbonyl)piperidin-4-yl)-5-(2-fluoro-pyridin-3-yl)-1H-indazole-3-carboxamide

[Reaction Scheme 11]

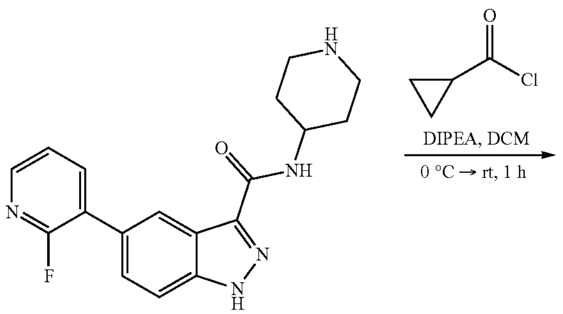

18-138

-continued

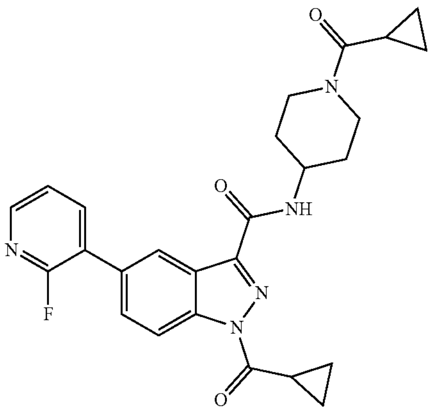

Compound 11

To a suspension of 18-138 (10 mg, 0.029 mmol) in DCM (2.0 ml) were added DIPEA (7.5 mg, 0.058 mmol) and then cyclopropyl carbonyl chloride (3.3 mg, 0.032 mmol) at 0° C., and the reaction mixture was stirred for 1 hour. When the starting material was completely consumed as monitored by TLC, the reaction mixture was quenched with water. After extraction with EtOAc (2×35 ml), the organic layer was washed with saturated brine. The organic layers thus obtained were pooled and concentrated at a reduced pressure to give a crude mixture. Purification by column chromatography using EtOAc/Hex (2:3) as an eluent afforded Compound 11 as a white solid (8.0 mg, 0.013 mmol, 43%).

1H NMR (300 MHz, CDCl3) δ 8.63 (s, 1H), 8.53 (d, J=8.8 Hz, 1H), 8.26 (d, J=4.8 Hz, 1H), 8.00 (ddd, J=9.6, 7.5, 1.9 Hz, 1H), 7.84 (dt, J=8.8, 1.8 Hz, 1H), 7.34 (ddd, J=6.8, 4.9, 1.7 Hz, 1H), 7.02 (d, J=8.1 Hz, 1H), 4.72-4.57 (m, 1H), 4.42-4.24 (m, 2H), 3.41-3.28 (m, 1H), 3.27-3.18 (m, 1H), 2.96-2.79 (m, 1H), 2.25-2.08 (m, 2H), 1.85-1.72 (m, 1H), 1.61-1.54 (m, 2H) 1.46-1.39 (m, 2H), 1.29-1.22 (m, 2H), 1.05-0.98 (m, 2H), 0.83-0.78 (m, 2H); LC/MS 476.2 [M+H+].

Compound 12. N-(1-Benzoylpiperidin-4-yl)-5-(2-fluoropyridin-3-yl)-1H-indazole-3-carboxamide

[Reaction Scheme 12]

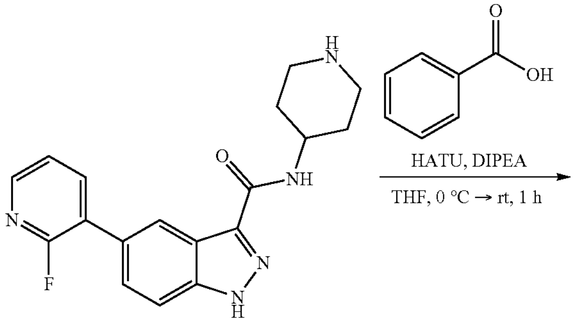

18-138

-continued

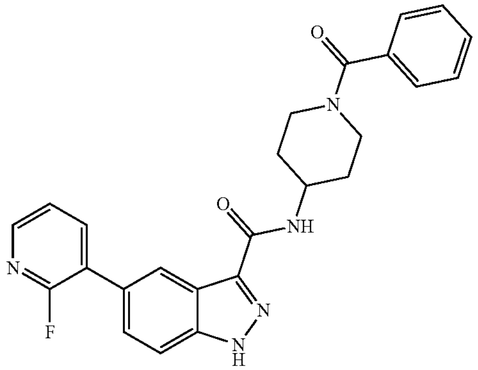

Compound 12

To a suspension of 18-138 (20 mg, 0.058 mmol) in THE (2.0 ml) were added DIPEA (15 mg, 0.116 mmol) and then HATU (24 mg, 0.064 mmol) at 0° C., and the reaction mixture was stirred for 15 minutes. After addition of benzoic acid (7.9 mg, 0.064 mmol), the reaction mixture was stirred at room temperature 14 hours. When the starting material was completely consumed as monitored by TLC, the reaction mixture was quenched with water. After extraction with EtOAc (2×35 ml), the organic layer was washed with saturated brine. The organic layers thus obtained were pooled and concentrated at a reduced pressure to give a crude mixture. Purification by column chromatography using EtOAc/Hex (2:3) as an eluent afforded Compound 12 as a white solid (12 mg, 0.027 mmol, 46%).

1H NMR (300 MHz, CDCl3) δ 11.25 (s, 1H), 8.57 (s, 1H), 8.23 (d, J=4.8 Hz, 1H), 7.98 (ddd, J=9.5, 7.5, 1.9 Hz, 1H), 7.69 (dt, J=8.8, 1.9 Hz, 1H), 7.57 (d, J=8.8 Hz, 1H), 7.45 (s, 5H), 7.36-7.30 (m, 1H), 7.07 (d, J=8.2 Hz, 1H), 4.88-4.68 (m, 1H), 4.45-4.27 (m, 1H), 4.01-3.79 (m, 1H), 3.29-3.06 (m, 2H), 2.30-2.10 (m, 2H), 1.83-1.69 (m, 1H), 1.64-1.49 (m, 1H); LC/MS 444.2 [M+H+].

Compound 13. 5-(2-Fluoropyridin-4-yl)-N-(piperidin-4-yl)-1H-indazole-3-carboxamide

[Reaction Scheme 13]

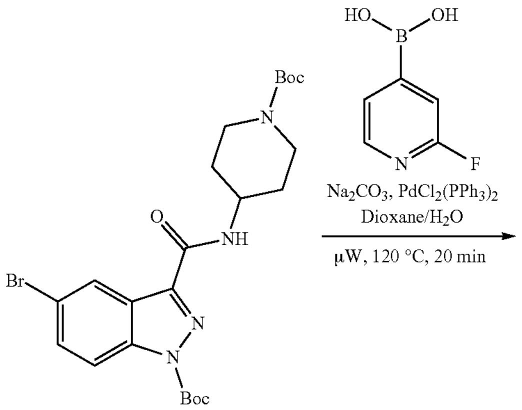

18-120

-continued

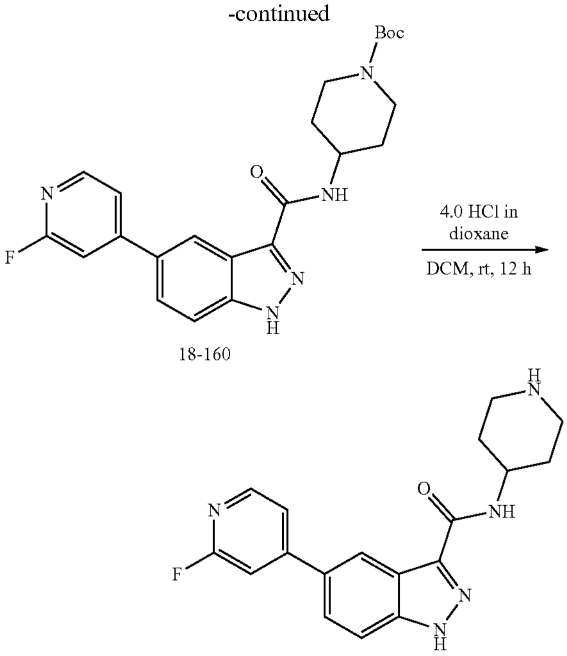

18-160

Compound 13

1) Synthesis of tert-butyl-4-(5-(2-fluoropyridin-4-yl)-1H-indazole-3-carboxamido)piperidine-1-carboxylate To a solution of 18-120 (100 mg, 0.191 mmol) in dioxane (2 ml) and $H_2O$ (0.5 ml) were added (2-fluoropyridin-4-yl) boronic acid (32.2 mg, 0.229 mmol) and sodium carbonate (51.8 mg, 0.477 mmol) at room temperature, and the reaction mixture was purged with nitrogen for 10 minutes. The solution was stirred and added with $PdCl_2(PPh_3)_2$ (13.4 mg, 0.019 mmol), and the resulting reaction mixture was exposed to microwaves at 120° C. for 20 minutes. After completion of the reaction, the solvent was removed using a rotary evaporator. The resulting crude mixture was diluted in 10 ml of water before extraction with ethyl acetate (2×15 ml). The organic layers thus obtained were pooled, dried over $Na_2SO_4$, and concentrated in a vacuum to give a crude mixture. Purification by column chromatography using EtOAc/Hex as an eluent afforded 18-160 as a white solid (60 mg, 0.136 mmol, 71%).

1H NMR (300 MHz, CDCl3) δ 10.57 (s, 1H), 8.75 (s, 1H), 8.30 (d, J=4.8 Hz, 1H), 7.75 (d, J=8.9 Hz, 1H), 7.66 (d, J=8.7 Hz, 1H), 7.53 (s, 1H), 7.25 (s, 1H), 7.00 (d, J=8.2 Hz, 1H), 4.16 (s, 3H), 3.07-2.91 (m, 2H), 2.10 (d, J=14.7 Hz, 2H), 1.58-1.52 (m, 2H), 1.51 (s, 9H); LC/MS 438.1 [M−H+].

2) Synthesis of 5-(2-fluoropyridin-4-yl)-N-(piperidin-4-yl)-1H-indazole-3-carboxamide To a solution of 18-160 (60 mg, 0.136 mmol) in DCM (15 ml) were added 4.0 M HCl in dioxane (2.0 ml) at 0° C., and the reaction mixture was stirred at room temperature for 12 hours. When the starting material was completely consumed as monitored by TLC, the reaction mixture was quenched with a sodium bicarbonate solution (aq). After extraction with DCM (25 ml×2), the organic layer was washed with saturated brine. The organic layers thus obtained were pooled and concentrated at a reduced pressure to give a crude mixture. Purification by column chromatography using MeOH/DCM afforded Compound 13 as a white solid (39 mg, 0.115 mmol, 85%).

1H NMR (300 MHz, CD3OD) S 8.66 (s, 1H), 8.29 (d, J=5.5 Hz, 1H), 7.88 (d, J=8.9 Hz, 1H), 7.77 (d, J=8.8 Hz, 1H), 7.71 (d, J=4.6 Hz, 1H), 7.46 (s, 1H), 4.35-4.22 (m, 1H), 3.52 (d, J=13.0 Hz, 2H), 3.22 (t, J=12.3 Hz, 2H), 2.28 (d, J=13.7 Hz, 2H), 2.05-1.88 (m, 2H); LC/MS 340.1 [M+H+].

Compound 14. N-Cyclohexyl-5-(2-fluoropyridin-3-yl)-1H-indazole-3-carboxamide

Reaction Scheme 14

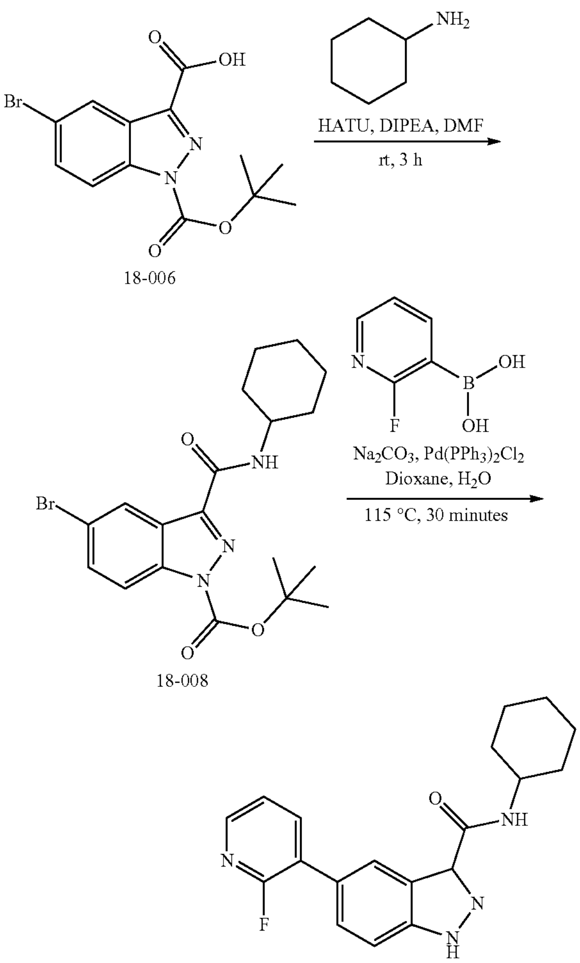

18-006

18-008

Compound 14

1) Synthesis of tert-butyl 5-bromo-3-(cyclohexylcarbamoyl)-1H-indazole-1-carboxylate To a solution of 18-006 (50 mg, 0.147 mmol) in DMF (2 ml) were added DIPEA (0.05 ml, 0.294 mmol) and then HATU (67 mg, 0.176 mmol). After addition of cyclohexylamine (0.018 ml, 0.162 mmol), the reaction mixture was stirred at room temperature for 3 hours. When the starting materials were completely consumed as monitored by TLC, the reaction mixture was quenched with water. After extraction with EtOAc (2×35 ml), the organic layer was washed with saturated brine and concentrated by evaporation in a vacuum to give a crude product. Purification by silica gel chromatography using EtOAc/Hx 3:7 as an eluent afforded 18-008 as a white solid (44 mg, 0.104 mmol, 71%).

1H NMR (300 MHz, CDCl3) δ 8.66 (s, 1H), 7.97 (d, J=8.9 Hz, 1H), 7.65 (d, J=9.0 Hz, 1H), 7.09 (d, J=7.9 Hz, 1H), 4.03-4.00 (m, 1H), 2.09-2.05 (m, 2H), 1.88-1.79 (m, 2H), 1.77 (s, 9H), 1.55-1.19 (m, 6H).

2) Synthesis of N-cyclohexyl-5-(2-fluoropyridin-3-yl)-1H-indazole-3-carboxamide

A solution of $Na_2CO_3$ (26 mg, 0.237 mmol) in water (0.5 ml) was introduced into a suspension of 18-008 (50 mg, 0.095 mmol) and (2-fluoropyridin-3-yl)boronic acid (16 mg, 0.114 mmol) in dioxane (2 ml), followed by purging with nitrogen for 0.5 minutes. After addition of $Pd(PPh_3)_2Cl_2$ (7 mg, 0.009 mmol) thereto, the reaction mixture was exposed to microwaves at 115° C. for 30 minutes. TLC and LC/MS indicated the presence of the starting materials in the reaction mixture. The reaction mixture was added with water before extraction with ethyl acetate (2×15 ml). The organic layer was dried over sodium sulfate and concentrated by evaporation in a vacuum to give a crude mixture. Purification by silica gel chromatography using EtOAc/Hx 3:7 as an eluent afforded Compound 14 as a white solid (5 mg, 0.015 mmol, 16%).

1H NMR (400 MHz, CDCl3) δ 8.60 (s, 1H), 8.21 (d, J=4.6 Hz, 1H), 8.01-7.94 (m, 1H), 7.70 (d, J=8.8 Hz, 1H), 7.59 (d, J=8.7 Hz, 1H), 7.30 (d, J=5.3 Hz, 1H), 6.96 (d, J=8.1 Hz, 1H), 4.10-3.99 (m, 1H), 2.07 (d, J=8.9 Hz, 2H), 1.83-1.75 (m, 2H), 1.48-1.28 (m, 6H).

Compound 15. 1-(5-(2-Fluoropyridin-3-yl)-1H-indazole-3-carbonyl)piperidine-4-carboxamide Reaction Scheme 15

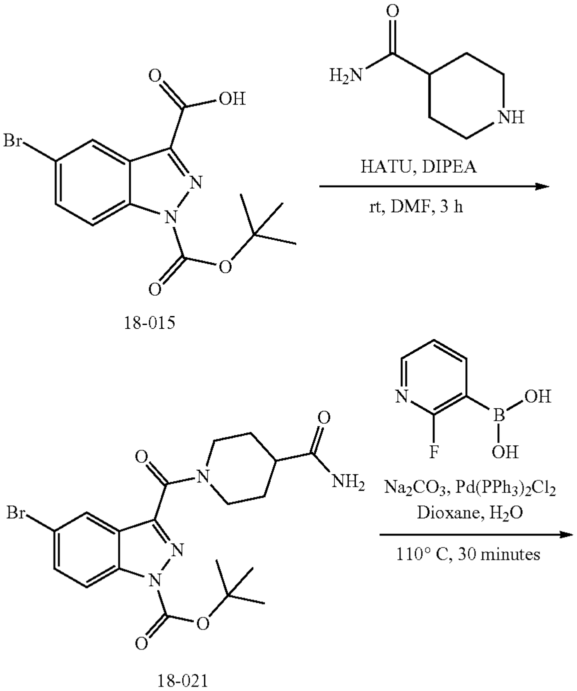

18-015

18-021

-continued

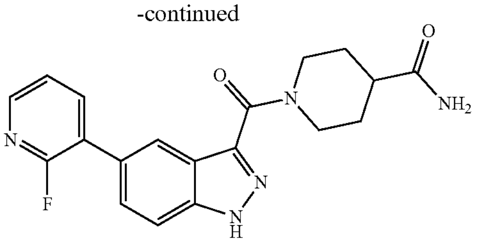

Compound 15

1) Synthesis of tert-butyl 5-bromo-3-(4-carbamoylpiperidine-1-carbonyl)-1H-indazole-1-carboxylate To a solution of 18-015 (150 mg, 0.147 mmol) in DMF (6 ml) were added DIPEA (0.15 ml, 0.879 mmol) and then HATU (201 mg, 0.528 mmol). After addition of piperidine-4-carboxamide (63 mg, 0.484 mmol), the reaction mixture was stirred at room temperature 3 hours. When the starting materials were completely consumed as monitored by TLC, the reaction mixture was quenched with water. After extraction with EtOAc (2×45 ml), the organic layer was washed with saturated brine. The organic layer was concentrated by evaporation in a vacuum to give a crude product. Purification by silica gel chromatography using MeOH/DCM 1:9 as an eluent afforded 18-021 as a white solid (178 mg, 0.394 mmol, 90%).

1H NMR (400 MHz, DMSO-d6) δ 8.11 (d, J=1.4 Hz, 1H), 8.05 (d, J=8.9 Hz, 1H), 7.81 (dd, J=9.0, 1.9 Hz, 1H), 7.31 (s, 1H), 6.82 (s, 1H), 4.51 (d, J=12.6 Hz, 1H), 4.23 (d, J=13.7 Hz, 1H), 3.21 (t, J=11.6 Hz, 1H), 2.95 (t, J=11.3 Hz, 1H), 2.48-2.36 (m, 1H), 1.90-1.80 (m, 1H), 1.73 (d, J=11.1 Hz, 1H), 1.66 (s, 9H), 1.60-1.47 (m, 2H).

LC/MS 453.0 [M+H+].

2) Synthesis of 1-(5-(2-fluoropyridin-3-yl)-1H-indazole-3-carbonyl)piperidine-4-carboxamide A solution of $Na_2CO_3$ (60 mg, 0.555 mmol) in water (0.5 ml) was introduced into a suspension of 18-021 (100 mg, 0.222 mmol) and (2-fluoro pyridin-3-yl)boronic acid (37 mg, 0.266 mmol) in dioxane (2 ml), followed by purging with nitrogen for 5 minutes. The reaction mixture was added with $Pd(PPh_3)_2C_{1-2}$ (16 mg, 0.022 mmol) and then exposed to microwaves at 110° C. for 30 minutes. LC/MS and TLC indicated the complete consumption of the starting material. The reaction mixture was added with water before extraction with ethyl acetate (15 ml). The organic layer was dried over sodium sulfate and concentrated by evaporation in a vacuum to give a crude mixture. Purification by silica gel chromatography using MeOH/DCM 1:9 as an eluent afforded Compound 15 as a white solid (30 mg, 0.082 mmol, 37%).

1H NMR (400 MHz, DMSO-d6) δ 8.25 (d, J=4.7 Hz, 1H), 8.19-8.13 (m, 2H), 7.74 (d, J=8.7 Hz, 1H), 7.65 (d, J=8.7 Hz, 1H), 7.48 (ddd, J=7.0, 4.8, 1.8 Hz, 1H), 7.31 (s, 1H), 6.81 (s, 1H), 4.72 (s, 1H), 4.58 (s, 1H), 3.27-3.19 (m, 1H), 2.94-2.83 (m, 1H), 2.48-2.40 (m, 1H), 1.88-1.73 (m, 2H), 1.61-1.50 (s, 2H).

LC/MS 368.1 [M+H+]

Compound 16. 5-(2-Fluoropyridin-3-yl)-N-((1r,4r)-4-hydroxycyclohexyl)-1H-indazole-3-carboxamide

[Reaction Scheme 16]

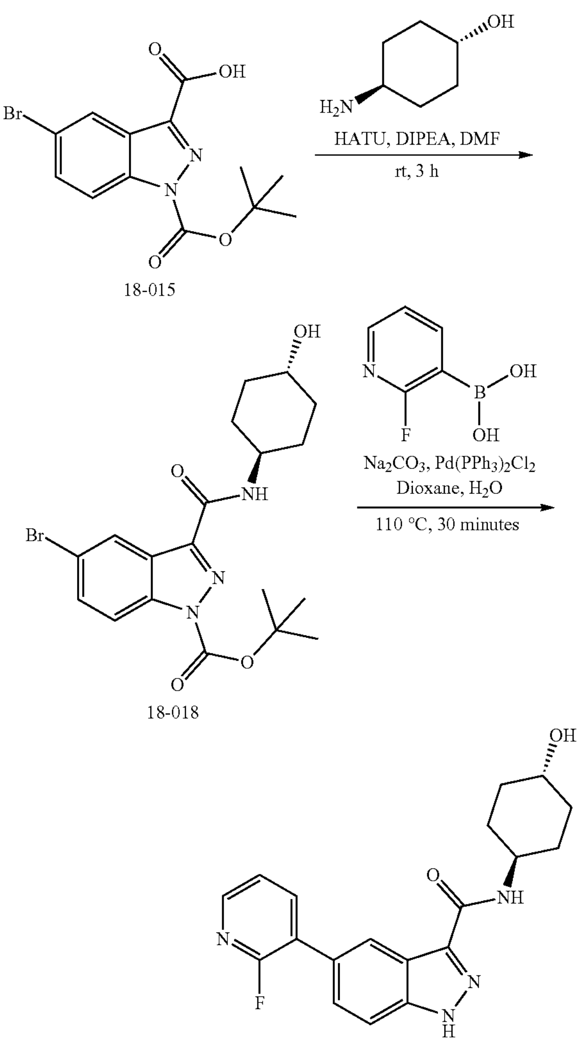

Compound 16

1) Synthesis of tert-butyl-5-bromo-3-(((1r,4r)-4-hydroxycyclohexyl)carbamoyl)-1H-indazole-1-carboxylate To a solution of 18-015 (150 mg, 0.147 mmol) in DMF (6 ml) were added DIPEA (0.15 ml, 0.879 mmol) and then HATU (201 mg, 0.528 mmol). After addition of 4-aminocyclohexan-1-ol (56 mg, 0.484 mmol), the reaction mixture was stirred at room temperature for 3 hours. When the starting materials were completely consumed as monitored by TLC, the reaction mixture was quenched with water. After extraction with EtOAc (2×45 ml), the organic layer was washed with saturated brine. The organic layer was concentrated by evaporation in a vacuum to give a crude product. Purification by silica gel chromatography using EtOAc/Hx 1:1 as an eluent afforded 18-018 as a white solid (115 mg, 0.262 mmol, 60%).

1H NMR (400 MHz, CD3OD) S 8.46 (d, J=1.4 Hz, 1H), 8.06 (d, 1H), 7.74 (dd, J=9.0, 1.9 Hz, 1H), 3.96-3.86 (m, 1H), 3.65-3.54 (m, 1H), 2.10-1.98 (m, 4H), 1.74 (s, 9H), 1.54-1.39 (m, 4H).

LC/MS 338.1 [M-100]+.

2) Synthesis of 5-(2-fluoropyridin-3-yl)-N-((1r,4r)-4-hydroxycyclohexyl)-1H-indazole-3-carboxamide A solution of $Na_2CO_3$ (49 mg, 0.456 mmol) in water (0.5 ml) was introduced into a suspension of 18-018 (100, mg, 0.228 mmol) and (2-fluoropyridin-3-yl)boronic acid (39 mg, 0.274 mmol) in dioxane (2 ml), followed by purging with nitrogen for 5 minutes. The reaction mixture was added with $Pd(PPh_3)_2C_{1-2}$ (16 mg, 0.023 mmol) and then exposed to microwaves at 110° C. for 30 minutes. TLC and LC/MS indicated the complete consumption of the starting material. The reaction mixture was added with water before extraction with ethyl acetate (15 ml). The organic layer was dried over sodium sulfate and concentrated by evaporation in a vacuum to give a crude mixture. Purification by silica gel chromatography using EtOAc/Hx 1:1 as an eluent afforded Compound 16 as a white solid (22 mg, 0.062 mmol, 27%).

1H NMR (400 MHz, DMSO-d6) δ 8.39 (s, 1H), 8.26 (d, J=4.8 Hz, 1H), 8.20-8.10 (m, 2H), 7.74 (d, J=8.7 Hz, 1H), 7.65 (d, J=8.7 Hz, 1H), 7.50 (ddd, J=7.0, 4.8, 1.8 Hz, 1H), 4.56 (s, 1H), 3.87-3.73 (m, 1H), 3.44-3.38 (m, 1H). 1.85 (t, J=12.9 Hz, 4H), 1.57-1.43 (m, 2H), 1.32-1.19 (m, 2H).

LC/MS 353.1 [M−H+]

Compound 17. 5-(2-Fluoropyridin-3-yl)-N-(pyridin-4-yl)-1H-indazole-3-carboxamide

[Reaction Scheme 17]

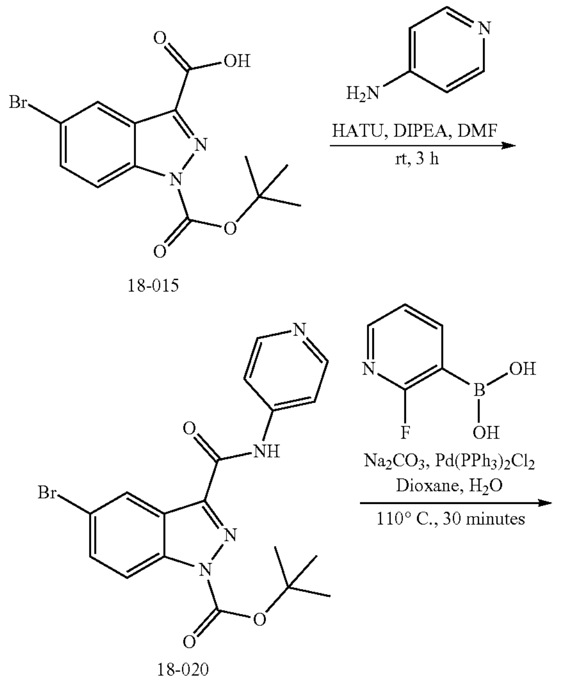

18-015
18-020

-continued

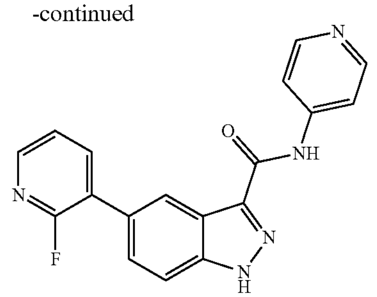

Compound 17

1) Synthesis of tert-butyl 5-bromo-3-(pyridin-4-ylcarbamoyl)-1H-indazole-1-carboxylate To a solution of 18-015 (150 mg, 0.147 mmol) in DMF (6 ml) were added DIPEA (0.15 ml, 0.879 mmol) and then HATU (201 mg, 0.528 mmol). After addition of pyridin-4-amine (46 mg, 0.484 mmol), the reaction mixture was stirred at room temperature for 3 hours. When the starting materials were completely consumed as monitored by TLC, the reaction mixture was quenched with water. After extraction with EtOAc (2×45 ml), the organic layer was washed with saturated brine. The organic layer was concentrated by evaporation in a vacuum to give a crude product. Purification by silica gel chromatography using EtOAc/Hx 3:7 as an eluent afforded 18-020 as a white solid (122 mg, 0.268 mmol, 61%).

1H NMR (400 MHz, CDCl3) δ 9.19 (s, 1H), 8.66 (d, J=1.4 Hz, 1H), 8.59 (dd, J=4.8, 1.5 Hz, 2H), 8.00 (s, 1H), 7.76-7.66 (m, 3H), 1.78 (s, 9H).

LC/MS 416.1 [M−H+.]

2) Synthesis of 5-(2-fluoropyridin-3-yl)-N-(pyridin-4-yl)-1H-indazole-3-carboxamide A solution of $Na_2CO_3$ (52 mg, 0.237 mmol) in water (0.5 ml) was introduced into a suspension of 18-020 (100 mg, 0.240 mmol) and (2-fluoropyridin-3-yl)boronic acid (41 mg, 0.288 mmol) in dioxane (2 ml), followed by purging with nitrogen for 5 minutes. The reaction mixture was added with $Pd(PPh_3)_2C_{1-2}$ (17 mg, 0.024 mmol) and then exposed to microwaves at 110° C. for 30 minutes. TLC and LC/MS indicated the complete consumption of the starting material. The reaction mixture was added with water before extraction with ethyl acetate (15 ml). The organic layer was dried over sodium sulfate and concentrated by evaporation in a vacuum to give a crude mixture. Purification by silica gel chromatography using EtOAc/Hx 1:1 as an eluent afforded Compound 17 as a white solid (14 mg, 0.042 mmol, 18%).

1H NMR (400 MHz, DMSO-d6) δ 10.83 (s, 1H), 8.48 (dd, J=4.9, 1.4 Hz, 1H), 8.44 (s, 1H). 8.28 (d, J=4.8 Hz, 1H), 8.25-8.18 (m, 1H), 7.94 (dd, J=4.9, 1.5 Hz, 2H), 7.83 (d, J=8.7 Hz, 1H), 7.72 (d, J=8.7 Hz, 1H), 7.54-7.49 (m, 1H).

LC/MS 334.1 [M+H+]

Compound 18. N-((1s,4s)-4-Aminocyclohexyl)-5-(2-fluoropyridin-3-yl)-1H-indazole-3-carboxamide

[Reaction Scheme 18]

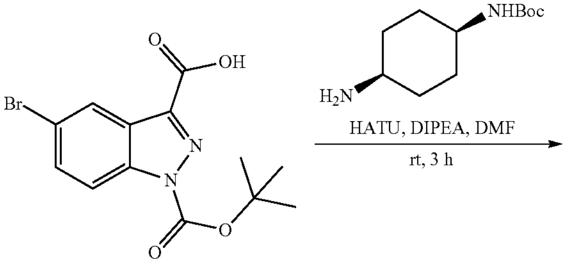

18-015

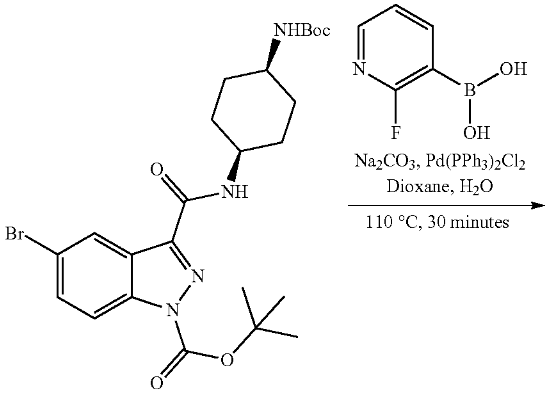

18-016

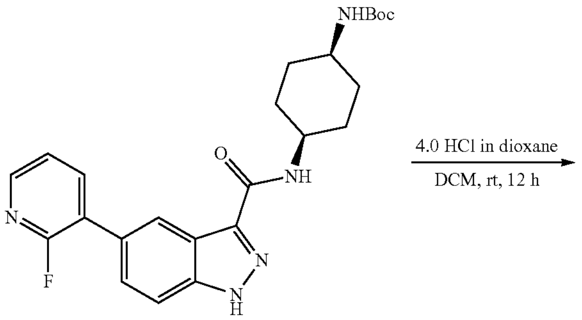

18-022

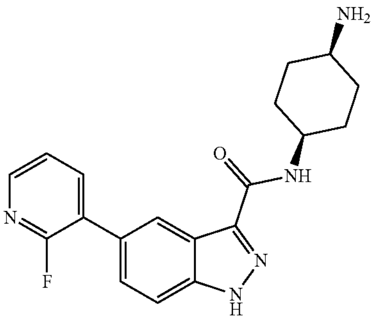

Compound 18

1) Synthesis of tert-butyl 5-bromo-3-(((1s,4s)-4-((tert-butoxycarbonyl) amino)cyclohexyl)carbamoyl)-1H-indazole-1-carboxylate To a solution of 18-015 (150 mg, 0.147 mmol) in DMF (6 ml) were added DIPEA (0.15 ml, 0.879 mmol) and then HATU (201 mg, 0.528 mmol). After addition of tert-butyl ((1s, 4s)-4-aminocyclohexyl)carbamate (104 mg, 0.484 mmol), the reaction mixture was stirred at room temperature for 3 hours. When the starting materials were completely consumed as monitored by TLC, the reaction mixture was quenched with water. After extraction with EtOAc (2×45 ml), the organic layer was washed with saturated brine. The organic layer was concentrated by evaporation in a vacuum to give a crude product. Purification by silica gel chromatography using EtOAc/Hx 3:7 as an eluent afforded 18-016 as a white solid (186 mg, 0.346 mmol, 79%).

1H NMR (400 MHz, CDCl3) δ 8.62 (d, J=1.5 Hz, 1H), 7.96 (d, J=9.0 Hz, 1H), 7.64 (dd, J=9.0, 1.9 Hz, 1H), 7.17 (d, J=7.6 Hz, 1H), 4.61 (s, 1H), 4.18-4.07 (m, 1H), 3.70 (s, 1H), 1.92-1.77 (m, 4H), 1.75 (s, 9H), 1.73-1.66 (m, 4H), 1.46 (s, 9H).

LC/MS 438.0 [M-100]+.

2) Synthesis of tert-butyl-((1s,4s)-4-(5-(2-fluoropyridin-3-yl)-1H-indazole-3-carboxamido)cyclohexyl)carbamate A solution of $Na_2CO_3$ (40 mg, 0.372 mmol) in water (0.5 ml) was introduced into a suspension of 18-016 (100 mg, 0.186 mmol) and (2-fluoro pyridin-3-yl)boronic acid (31 mg, 0.223 mmol) in dioxane (2 ml), followed by purging with nitrogen for 5 minutes. The reaction mixture was added with $Pd(PPh_3)_2C_{1-2}$ (13 mg, 0.019 mmol) and then exposed to microwaves at 110° C. for 30 minutes. TLC and LC/MS indicated the complete consumption of the starting material. The reaction mixture was added with water before extraction with ethyl acetate (15 ml). The organic layer was dried over sodium sulfate and concentrated by evaporation in a vacuum to give a crude mixture. Purification by silica gel chromatography using EtOAc/Hx 1:1 as an eluent afforded 18-022 as a white solid (38 mg, 0.084 mmol, 45%).

1H NMR (400 MHz, CDCl3) δ 8.58 (s, 1H), 8.21 (d, J=4.8 Hz, 1H), 7.97 (ddd, J=9.6, 7.4, 1.8 Hz, 1H), 7.72-7.67 (m, 1H), 7.60 (d, J=8.7 Hz, 1H), 7.31-7.27 (m, 1H), 7.10 (d, J=7.4 Hz, 1H), 4.62 (s, 1H), 4.24-4.14 (m, 1H), 3.68 (s, 1H), 1.93-1.80 (m, 4H), 1.80-1.63 (m, 4H), 1.46 (s, 9H).

LC/MS 452.1 [M–H+]

3) Synthesis of N-((1s,4s)-4-aminocyclohexyl)-5-(2-fluoropyridin-3-yl)-1H-indazole-3-carboxamide To a solution of 18-022 (30 mg, 0.066 mmol) in DCM (15 ml) was added 4.0 M HCl in dioxane (2.0 ml) at 0° C., and the reaction mixture was stirred at room temperature for 12 hours. When the starting material was completely consumed as monitored by TLC, the reaction mixture was concentrated in a vacuum to afford Compound 18 as a white solid (20 mg, 0.056 mmol, 85%).

1H NMR (400 MHz, CD3OD) δ 8.48 (s, 1H), 8.22 (d, J=4.4 Hz, 1H), 8.18-8.11 (m, 1H), 7.76-7.68 (m, 2H), 7.49-7.45 (m, 1H), 4.22 (s, 1H), 3.32 (s, 1H), 2.09-1.95 (m, 4H), 1.94-1.79 (m, 4H).

LC/MS 354.1 [M+H+].

Compound 19. N-((1r,4r)-4-Aminocyclohexyl)-5-(2-fluoropyridin-3-yl)-1H-indazole-3-carboxamide

[Reaction Scheme 19]

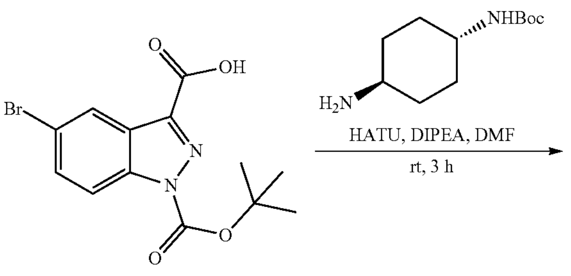

18-015

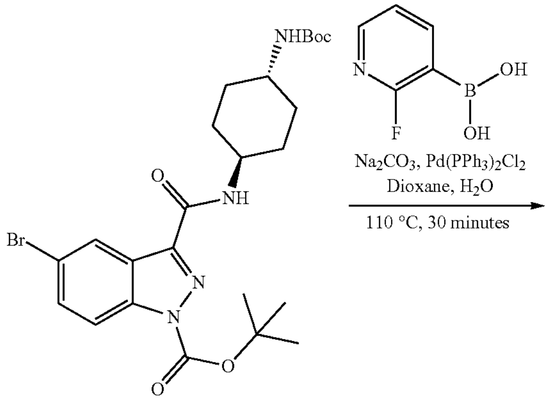

18-017

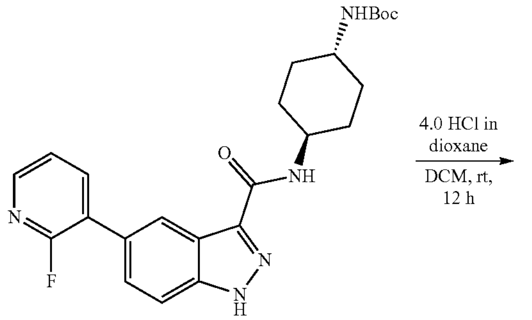

18-023

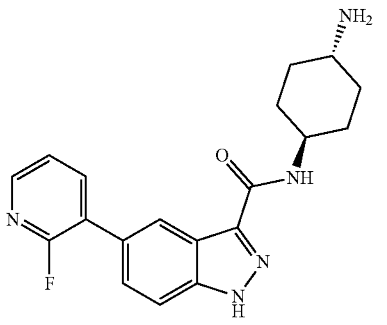

Compound 19

1) Synthesis of tert-butyl 5-bromo-3-(((1r,4r)-4-((tert-butoxycarbonyl) amino)cyclohexyl)carbamoyl)-1H-indazole-1-carboxylate To a solution of 18-015 (150 mg, 0.147 mmol) in DMF (6 ml) were added DIPEA (0.15 ml, 0.879 mmol) and then HATU (201 mg, 0.528 mmol). After addition of tert-butyl ((1r,4r)-4-aminocyclohexyl)carbamate (104 mg, 0.484 mmol), the reaction mixture was stirred at room temperature for 3 hours. When the starting materials were completely consumed as monitored by TLC, the reaction mixture was quenched with water. After extraction with EtOAc (2×45 ml), the organic layer was washed with saturated brine. The organic layer was concentrated by evaporation in a vacuum to give a crude product. Purification by silica gel chromatography using EtOAc/Hx 3:7 as an eluent afforded 18-017 as a yellow solid (172 mg, 0.320 mmol, 73%).

1H NMR (400 MHz, CDCl3) δ 8.61 (d, J=1.4 Hz, 1H), 7.95 (d, J=8.9 Hz, 1H), 7.64 (dd, J=9.0, 1.9 Hz, 1H), 7.04 (d, J=8.2 Hz, 1H), 4.42 (s, 1H), 4.02-3.91 (m, J=8.1 Hz, 1H), 3.47 (s, 1H), 2.11 (t, J=11.2 Hz, 4H), 1.74 (s, 9H), 1.45 (s, 9H), 1.36-1.23 (m, 4H).

LC/MS 438.0 [M-100]+.

2) Synthesis of tert-butyl ((1r,4r)-4-(5-(2-fluoropyridin-3-yl)-1H-indazole-3-carboxamido)cyclohexyl) carbamate A solution of $Na_2CO_3$ (40 mg, 0.372 mmol) in water (0.5 ml) was introduced into a suspension of 18-017 (100 mg, 0.186 mmol) and (2-fluoropyridin-3-yl)boronic acid (31 mg, 0.223 mmol) in dioxane (2 ml), followed by purging with nitrogen for 5 minutes. The reaction mixture was added with $Pd(PPh_3)_2C_{1-2}$ (13 mg, 0.019 mmol) and then exposed to microwaves at 110° C. for 30 minutes. TLC and LC/MS indicated the complete consumption of the starting material. The reaction mixture was added with water before extraction with ethyl acetate (15 ml). The organic layer was dried over sodium sulfate and concentrated by evaporation in a vacuum to give a crude mixture. Purification by silica gel chromatography using EtOAc/Hx 1:1 as an eluent afforded 18-023 as a white solid (28 mg, 0.062 mmol, 33%).

1H NMR (400 MHz, CDCl3) δ 8.55 (s, 1H), 8.20 (d, J=4.7 Hz, 1H), 8.02-7.94 (m, 1H), 7.69-7.63 (m, 1H), 7.59 (d, J=8.7 Hz, 1H), 7.32-7.29 (m, 1H), 6.95 (d, J=8.3 Hz, 1H), 4.50 (s, 1H), 4.05-3.94 (m, 1H), 3.51 (s, 1H), 2.13 (dd, J=28.0, 11.0 Hz, 4H), 1.47 (s, 9H), 1.44-1.29 (m, 4H).

LC/MS 452.1 [M–H+]

3) Synthesis of N'-((1r,4r)-4-aminocyclohexyl)-5-(2-fluoropyridin-3-yl)-1H-indazole-3-carboxamide To a solution of 18-023 (20 mg, 0.044 mmol) in DCM (15 ml) was added 4.0 M HCl in dioxane (2.0 ml) at 0° C., and the reaction mixture was stirred at room temperature for 12 hours. When the starting material was completely consumed as monitored by TLC, the reaction mixture was concentrated at a reduced pressure to afford Compound 19 as a white solid (13 mg, 0.037 mmol, 85%).

1H NMR (400 MHz, CD3OD) δ 8.47 (s, 1H), 8.22 (d, J=4.7 Hz, 1H), 8.14 (ddd, J=9.7, 7.5, 1.8 Hz, 1H), 7.71 (q, J=8.4 Hz, 2H), 7.46 (ddd, J=7.1, 4.9, 1.7 Hz, 1H), 4.02-3.95 (m, 1H), 3.23-3.13 (m, 1H), 2.17 (s, 4H), 1.67-1.54 (m, 4H).

LC/MS 352.1 [M–H+]

Compound 20. 5-(2-fluoropyridin-3-yl)-N-(pyrrodin-3-yl)-1H-indazole-3-carboxamide

[Reaction Scheme 20]

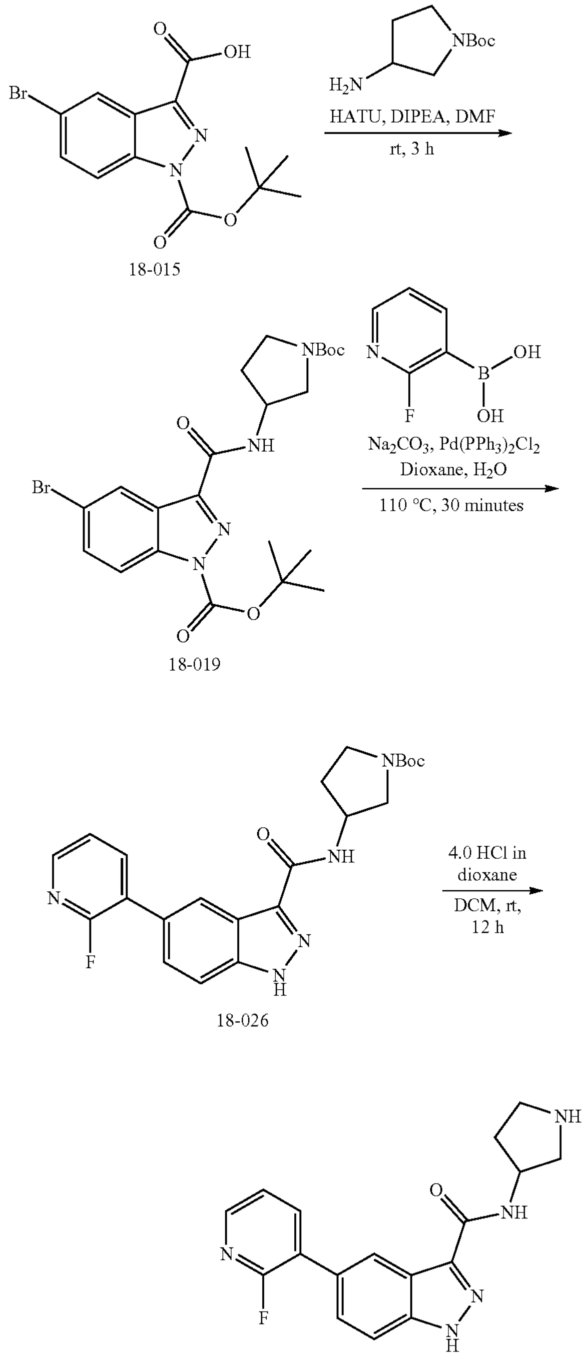

1) Synthesis of tert-butyl-5-bromo-3-((1-(tert-butoxycarbonyl)pyrolidin-3-yl)carbamoyl)-1H-indazole-1-carboxylate To a solution of 18-015 (150 mg, 0.147 mmol) in DMF (6 ml) were added DIPEA (0.15 ml, 0.879 mmol) and then HATU (201 mg, 0.528 mmol). After addition of tert-butyl 3-aminopyrrolidine-1-carboxylate (90 mg, 0.484 mmol), the reaction mixture was stirred at room temperature for 3 hours. When the starting materials were completely consumed as monitored by TLC, the reaction mixture was quenched with water. After extraction with EtOAc (2×45 ml), the organic layer was washed with saturated brine. The organic layer was concentrated by evaporation in a vacuum to give a crude product. Purification by silica gel chromatography using EtOAc/Hx 3:7 as an eluent afforded 18-019 as a white solid (136 mg, 0.267 mmol, 61%).

1H NMR (400 MHz, CDCl3) δ 8.61 (d, J=1.4 Hz, 1H), 7.97 (d, J=8.9 Hz, 1H), 7.65 (dd, J=9.0, 1.9 Hz, 1H), 7.31 (d, J=7.2 Hz, 1H), 4.74-4.65 (m, 1H), 3.75 (dd, J=11.3, 6.6 Hz, 1H), 3.56-3.30 (m, 3H), 2.34-2.20 (m, 1H), 2.09-1.96 (m, 1H), 1.75 (s, 9H), 1.48 (s, 9H).

LC/MS 410.0 [M-100]+.

2) Synthesis of tert-butyl-3-(5-(2-fluoropyridin-3-yl)-1H-indazole-3-carboxamido)pyrrolidine-1-carboxylate A solution of $Na_2CO_3$ (42 mg, 0.392 mmol) in water (0.5 ml) was introduced into a suspension of 18-019 (100 mg, 0.196 mmol) and (2-fluoro pyridin-3-yl)boronic acid (33 mg, 0.236 mmol) in dioxane (2 ml), followed by purging with nitrogen for 5 minutes. The reaction mixture was added with $Pd(PPh_3)_2Cl_2$ (14 mg, 0.020 mmol) and then exposed to microwaves at 110° C. for 30 minutes. TLC and LC/MS indicated the complete consumption of the starting material. The reaction mixture was added with water before extraction with ethyl acetate (15 ml). The organic layer was dried over sodium sulfate and concentrated by evaporation in a vacuum to give a crude mixture. Purification by silica gel chromatography using EtOAc/Hx 1:1 as an eluent afforded 18-026 as a white solid (38 mg, 0.089 mmol, 45%).

1H NMR (400 MHz, CDCl3) δ 8.55 (s, 1H), 8.21 (d, J=4.5 Hz, 1H), 8.00-7.93 (m, 1H), 7.69 (d, J=8.6 Hz, 1H), 7.62 (d, J=8.7 Hz, 1H), 7.30 (d, J=5.2 Hz, 1H), 7.19 (d, J=7.3 Hz, 1H), 4.79-4.68 (m, 1H), 3.84-3.69 (m, 1H), 3.62-3.35 (m, 4H), 2.05-2.97 (m, 1H), 1.49 (s, 9H).

LC/MS 424.1 [M−H+]

3) Synthesis of 5-(2-fluoropyridin-3-yl)-N-(pyrrolidin-3-yl)-1H-indazole-3-carboxamide To a solution of 18-026 (30 mg, 0.071 mmol) in DCM (15 ml) was added 4.0 M HCl in dioxane (2.0 ml) at 0° C., and the reaction mixture was stirred at room temperature for 12 hours. When the starting material was completely consumed as monitored by TLC, the reaction mixture was concentrated at a reduced pressure to afford Compound 20 as a white solid (20 mg, 0.060 mmol, 85%).

1H NMR (400 MHz, CD3OD) δ 8.47 (s, 1H), 8.22 (d, J=4.6 Hz, 1H), 8.18-8.11 (m, 1H), 7.76-7.66 (m, 2H), 7.49-7.44 (m, 1H), 4.77-4.70 (m, 1H), 3.71-3.66 (m, 1H), 3.65-3.59 (m, 2H), 3.52-3.39 (m, 2H), 2.54-2.43 (m, 1H), 2.34-2.22 (m, 1H).

LC/MS 326.0 [M+H+].

Compound 21. (3,4-Dihydroisoquinolin-2-(1H)-yl)(5-(2-fluoropyridin-3-yl)-1H-indazol-3-yl)methanone

[Reaction Scheme 21]

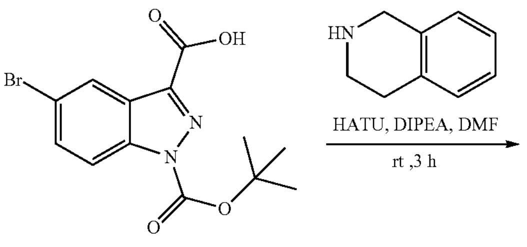

18-015

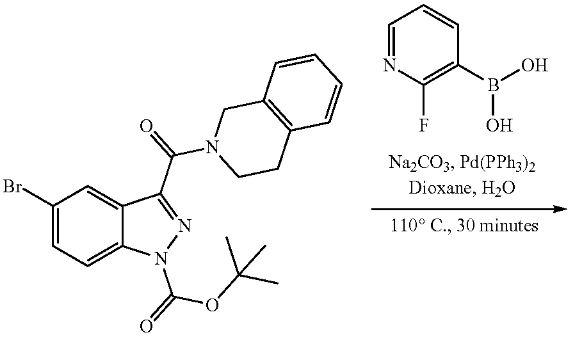

18-031

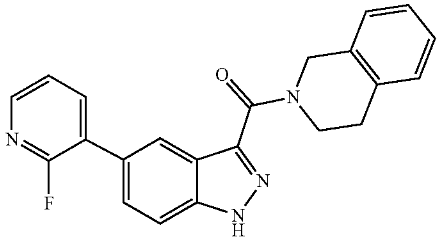

Compound 21

1) Synthesis of tert-butyl-5-bromo-3-(1,2,3,4-tetrahydroisoquinoline-2-carbonyl)-1H-indazole-1-carboxylate To a solution of 18-015 (150 mg, 0.147 mmol) in DMF (6 ml) were added DIPEA (0.15 ml, 0.879 mmol) and then HATU (201 mg, 0.528 mmol). After addition of 1,2,3,4-tetrahydroisoquinoline (64 mg, 0.484 mmol), the reaction mixture was stirred at room temperature for 3 hours. When the starting materials were completely consumed as monitored by TLC, the reaction mixture was quenched with water. After extraction with EtOAc (50 ml), the organic layer was washed with saturated brine. The organic layer was concentrated by evaporation in a vacuum to give a crude product. Purification by silica gel chromatography using EtOAc/Hx 3:7 as an eluent afforded 18-031 as a white solid (126 mg, 0.276 mmol, 63%).

1H NMR (400 MHz, CDCl3) δ 8.31 (s, 1H), 8.04 (d, J=8.9 Hz, 1H), 7.67-7.61 (m, 1H), 7.25-7.14 (m, 4H), 5.22 (s, 1H), 4.97 (s, 1H), 4.21 (t, J=5.9 Hz, 1H), 4.06 (t, J=6.1 Hz, 1H), 3.03 (t, J=5.9 Hz, 2H), 1.74 (d, J=5.5 Hz, 9H).

LC/MS 357.0 [M-100]+.

2) Synthesis of (3,4-dihydroisoquinolin-2(1H)-yl)(5-(2-fluoropyridin-3-yl)-1H-indazol-3-yl)methanone A solution of $Na_2CO_3$ (47 mg, 0.438 mmol) in water (0.5 ml) was introduced into a suspension of 18-031 (100 mg, 0.219 mmol) and (2-fluoropyridin-3-yl)boronic acid (37 mg, 0.263 mmol) in dioxane (2 ml), followed by purging with nitrogen for 5 minutes. The reaction mixture was added with $Pd(PPh_3)_2C_{1-2}$ (15 mg, 0.022 mmol) and then exposed to microwaves at 110° C. for 30 minutes. TLC and LC/MS indicated the complete consumption of the starting material. The reaction mixture was added with water before extraction with ethyl acetate (15 ml). The organic layer was dried over sodium sulfate and concentrated by evaporation in a vacuum to give a crude mixture. Purification by silica gel chromatography using EtOAc/Hx 3:2 as an eluent afforded Compound 21 as a white solid (31 mg, 0.083 mmol, 38%).

1H NMR (400 MHz, CDCl3) δ 10.37 (s, 1H), 8.36 (m, 1H), 8.20 (m, 1H), 7.95 (m, 1H), 7.69 (m, 1H), 7.60 (m, 1H), 7.51-7.42 (m, 4H), 5.30 (s, 1H), 5.01 (s, 1H), 4.28 (m, 1H), 4.10 (m, 1H), 3.04 (m, 2H).

LC/MS 373.1 [M+H+]

Compound 22. 5-(2-Fluoropyridin-3-yl)-N-(2-morpholinoethyl)-1H-indazole-3-carboxamide

[Reaction Scheme 22]

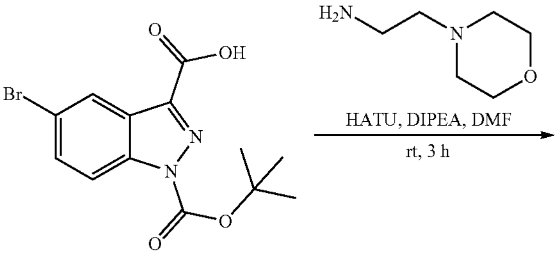

18-015

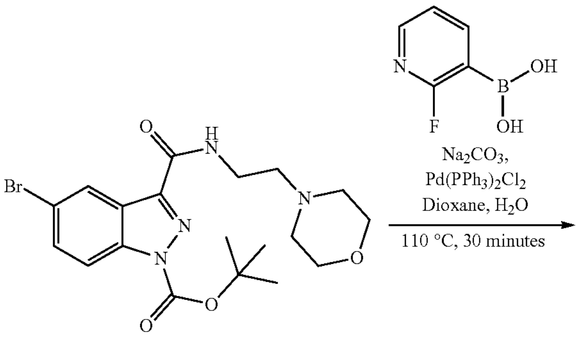

18-032

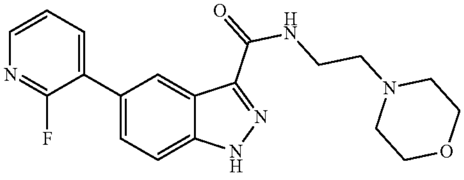

Compound 22

1) Synthesis of tert-butyl 5-bromo-3-((2-morpholinoethyl)carbamoyl)-1H-indazole-1-carboxylate To a solution of 18-015 (150 mg, 0.147 mmol) in DMF (6 ml) were added DIPEA (0.15 ml, 0.879 mmol) and then HATU (201 mg, 0.528 mmol). After addition of 2-morpholinoethan-1-amine (63 mg, 0.484 mmol), the reaction mixture was stirred at room temperature for 3 hours. When the starting materials were completely consumed as monitored by TLC, the reaction mixture was quenched with water. After extraction with EtOAc (2×45 ml), the organic layer was washed with saturated brine. The organic layer was concentrated by evaporation in a vacuum to give a crude product. Purification by silica gel chromatography using EtOAc/Hx 6:4 as an eluent afforded 18-032 as a white solid (129 mg, 0.285 mmol, 65%).

1H NMR (400 MHz, CDCl3) δ 8.59 (d, J=1.4 Hz, 1H), 7.99 (d, J=8.9 Hz, 1H), 7.75-7.68 (m, 1H), 7.64 (dd, J=9.0, 1.9 Hz, 1H), 3.80-3.76 (m, 4H), 3.67-3.62 (m, 2H), 2.72 (t, J=6.2 Hz, 2H), 2.67-2.60 (m, 4H), 1.74 (s, 9H).

LC/MS [M-100]+.

2) Synthesis of 5-(2-fluoropyridin-3-yl)-N-(2-morpholinoethyl)-1H-indazole-3-carboxamide A solution of $Na_2CO_3$ (48 mg, 0.442 mmol) in water (0.5 ml) was introduced into a suspension of 18-032 (100 mg, 0.221 mmol) and (2-fluoropyridin-3-yl)boronic acid (37 mg, 0.265 mmol) in dioxane (2 ml), followed by purging with nitrogen for 5 minutes. The reaction mixture was added with $Pd(PPh_3)_2C_{1-2}$ (15 mg, 0.022 mmol) and then exposed to microwaves at 110° C. for 30 minutes. TLC and LC/MS indicated the complete consumption of the starting material. The reaction mixture was added with water before extraction with ethyl acetate (15 ml). The organic layer was dried over sodium sulfate and concentrated by evaporation in a vacuum to give a crude mixture. Purification by silica gel chromatography using MeOH/DCM 1:9 as an eluent afforded Compound 22 as a white solid (45 mg, 0.122 mmol, 55%).

1H NMR (400 MHz, CDCl3) δ 8.54 (s, 1H), 8.21 (d, J=4.5 Hz, 1H), 7.95 (ddd, J=9.6, 7.4, 1.9 Hz, 1H), 7.69-7.65 (m, 1H), 7.61-7.56 (m, 1H), 7.31-7.28 (m, 1H), 3.81-3.75 (m, 4H), 3.70-3.63 (m, 2H), 2.69 (t, J=6.1 Hz, 1H), 2.63-2.54 (m, 4H).

LC/MS 373.1 [M+H+]

Compound 23. (5-(2-Fluoropyridin-3-yl)-1H-indazol-3-yl)(4-methylpiperazin-1-yl)methanone

[Reaction Scheme 23]

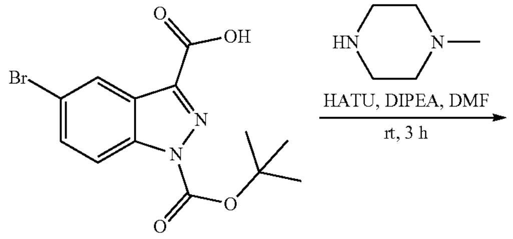

18-015

-continued

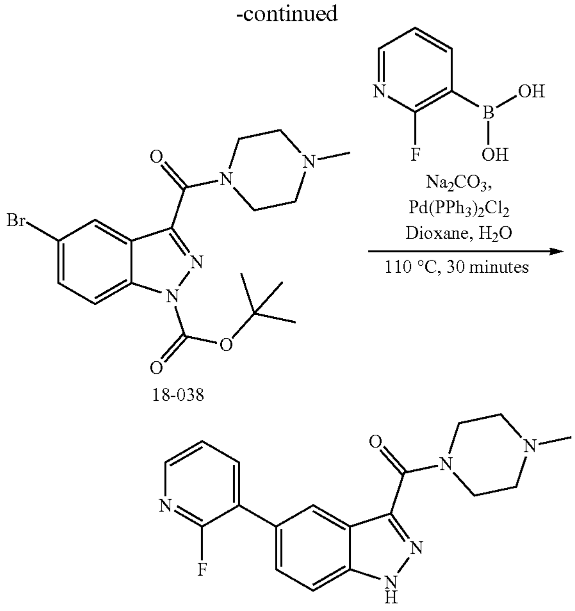

18-038

Compound 23

1) Synthesis of tert-butyl 5-bromo-3-(4-m ethylpiperazine-1-carbonyl)-1H-indazole-1-carboxylate To a solution of 18-015 (150 mg, 0.147 mmol) in DMF (6 ml) were added DIPEA (0.15 ml, 0.879 mmol) and then HATU (201 mg, 0.528 mmol). After addition of 1-m ethylpiperazine (0.053 ml, 0.484 mmol), the reaction mixture was stirred at room temperature for 3 hours. When the starting materials were completely consumed as monitored by TLC, the reaction mixture was quenched with water. After extraction with EtOAc (50 ml), the organic layer was washed with saturated brine. The organic layer was concentrated by evaporation in a vacuum to give a crude product. Purification by silica gel chromatography using MeOH/DCM 1:9 as an eluent afforded 18-038 as a yellow solid (144 mg, 0.340 mmol, 77%).

1H NMR (400 MHz, CDCl3) δ 8.28 (d, J=1.4 Hz, 1H), 8.01 (d, J=8.9 Hz, 1H), 7.64 (dd, J=8.9, 1.9 Hz, 1H), 4.12-4.02 (m, 2H), 3.96-3.87 (m, 2H), 2.57 (dt, J=20.5, 5.0 Hz, 4H), 2.37 (s, 2H), 1.72 (s, 9H).

LC/MS 425.0 [M+H+].

2) Synthesis of (5-(2-fluoropyridin-3-yl)-1H-indazol-3-yl)(4-methylpiperazin-1-yl)methanone A solution of $Na_2CO_3$ (51 mg, 0.472 mmol) in water (0.5 ml) was introduced into a suspension of 18-038 (100 mg, 0.236 mmol) and (2-fluoropyridin-3-yl)boronic acid (40 mg, 0.284 mmol) in dioxane (2 ml), followed by purging with nitrogen for 5 minutes. The reaction mixture was added with $Pd(PPh_3)_2C_{1-2}$ (17 mg, 0.024 mmol) and then exposed to microwaves at 110° C. for 30 minutes. TLC and LC/MS indicated the complete consumption of the starting material. The reaction mixture was added with water before extraction with ethyl acetate (15 ml). The organic layer was dried over sodium sulfate and concentrated by evaporation in a vacuum to give a crude mixture. Purification by silica gel chromatography using MeOH/DCM 1:9 as an eluent afforded Compound 23 as a white solid (35 mg, 0.103 mmol, 44%).

1H NMR (400 MHz, DMSO-d6) δ 8.25 (d, J=4.7 Hz, 1H), 8.20-8.13 (m, 2H), 7.74 (d, J=8.7 Hz, 1H), 7.65 (d, J=8.7 Hz, 1H), 7.51-7.46 (m, 1H), 4.02 (s, 1H), 3.72 (s, 1H), 2.39 (s, 1H), 2.22 (s, 3H).

LC/MS 340.1 [M+H+]

Compound 24. 5-(2-Fluoropyridin-3-yl)-N-(2-(2,2,2-trifluoroacetyl)-1,2,3,4-tetrahydroisoquinolin-7-yl)-1H-indazole-3-carboxamide

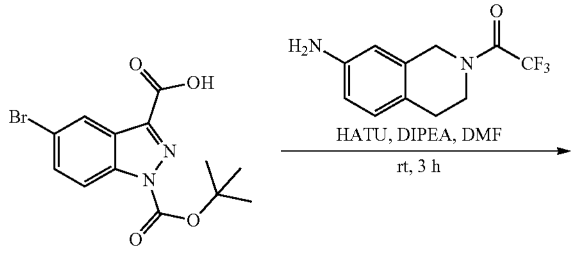

18-015

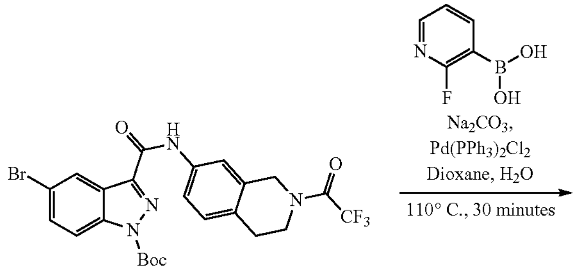

18-039

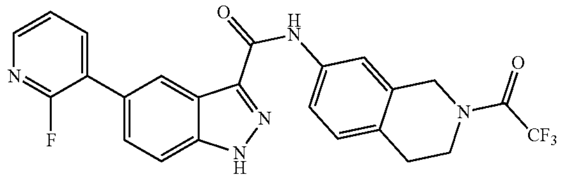

Compound 24

1) Synthesis of tert-butyl-5-bromo-3-((2-(2,2,2-trifluoroacetyl)-1,2,3,4-tetrahydroisoquinolin-7-yl)carbamoyl)-1H-indazole-1-carboxylate To a solution of 18-015 (150 mg, 0.147 mmol) in DMF (6 ml) were added DIPEA (0.15 ml, 0.879 mmol) and then HATU (201 mg, 0.528 mmol). After addition of 1-(7-amino-3,4-dihydroisoquinolin-2-(1H)-yl)-2,2,2-trifluoroethan-1-one (118 mg, 0.484 mmol), the reaction mixture was stirred at room temperature for 3 hours. When the starting materials were completely consumed as monitored by TLC, the reaction mixture was quenched with water. After extraction with EtOAc (50 ml), the organic layer was washed with saturated brine. The organic layer was concentrated by evaporation in a vacuum to give a crude product. Purification by silica gel chromatography using EtOAc/Hx 3:7 as an eluent afforded 18-039 as a yellow solid (149 mg, 0.263 mmol, 60%).

1H NMR (400 MHz, DMSO-d6) δ 10.65 (s, 1H), 8.40 (s, 1H), 8.08 (d, J=8.9 Hz, 1H), 7.86 (dd, J=9.0, 2.0 Hz, 1H), 7.77 (d, J=20.6 Hz, 1H), 7.67 (d, J=8.2 Hz, 1H), 7.26-7.22 (m, 1H), 4.77 (d, J=6.1 Hz, 2H), 3.84 (d, J=5.4 Hz, 2H), 2.94-2.88 (m, 2H), 1.71 (s, 9H).

LC/MS 566.8 [M−H+].

2) Synthesis of 5-(2-fluoropyridin-3-yl)-N-(2-(2,2,2-trifluoroacetyl)-1,2,3,4-tetrahydroisoquinolin-7-yl)-1H-indazole-3-carboxamide A solution of $Na_2CO_3$ (38 mg, 0.352 mmol) in water (0.5 ml) was introduced into a suspension of 18-039 (100 mg, 0.221 mmol) and (2-fluoropyridin-3-yl)boronic acid (30 mg, 0.212 mmol) in dioxane (2 ml), followed by purging with nitrogen for 5 minutes. The reaction mixture was added with $Pd(PPh_3)_2C_{1-2}$ (12 mg, 0.018 mmol) and then exposed to microwaves at 110° C. for 30 minutes. TLC and LC/MS indicated the complete consumption of the starting material. The reaction mixture was added with water before extraction with ethyl acetate (15 ml). The organic layer was dried over sodium sulfate and concentrated by evaporation in a vacuum to give a crude mixture. Purification by silica gel chromatography using EtOAc/Hx 1:1 as an eluent afforded Compound 24 as a white solid (26 mg, 0.054 mmol, 31%).

1H NMR (400 MHz, DMSO-d6) δ 10.39 (s, 1H), 8.45 (s, 1H), 8.27 (d, J=4.7 Hz, 1H), 8.23-8.17 (m, 1H), 7.84-7.78 (m, 2H), 7.74-7.66 (m, 2H), 7.52 (dt, J=4.4, 2.0 Hz, 1H), 7.20 (dd, J=8.3, 4.2 Hz, 1H), 4.76 (d, J=6.5 Hz, 2H), 3.88-3.79 (m, 2H), 2.96-2.86 (m, 2H).

LC/MS 484.0 [M+H+]

Compound 25. 5-(3,4-Difluorophenyl)-N-(pyridin-4-yl)-1H-indazole-3-carboxamide

[Reaction Scheme 25]

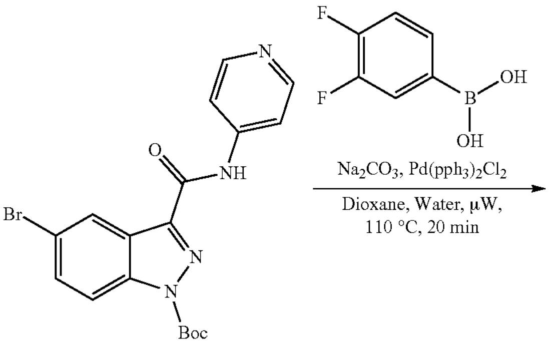

20-083

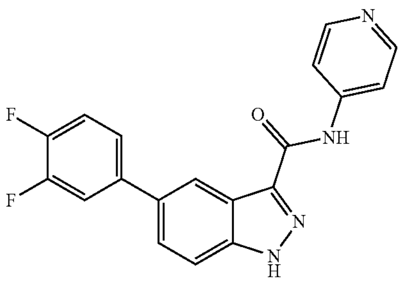

compound 25

A solution of $Na_2CO_3$ (15.3 mg, 0.144 mmol) in water was introduced into a suspension of 20-083 (20.0 mg, 0.0479 mmol), palladium catalyst (3.36 mg, 0.00479 mmol), (and (3,4-difluorophenyl)boronic acid (9.08 mg, 0.0575 mmol) in dioxane, followed by purging with nitrogen for 5 minutes. The reaction mixture was exposed to microwaves at 110° C. for 20 minutes. The crude reaction mixture was diluted with 10 mL of water, followed by extraction with 30 mL of ethyl acetate. The organic layers thus obtained were pooled, dried over $Na_2SO_4$, and concentrated in a vacuum to give a crude mixture. Purification by column chromatography using DCM/MeOH 5% as an eluent afforded Compound 25 as a white solid (10.3 mg, 0.0310 mmol, 65%).

$^1$H NMR (300 MHz, DMSO-$d_6$) δ 14.12 (s, 1H), 10.85 (s, 1H), 8.48 (d, J=5.7 Hz, 2H), 8.45-8.33 (m, 2H), 7.98-7.90 (m, 2H), 7.80 (s, 1H), 7.73-7.67 (m, 1H), 7.64-7.54 (m, 2H).

Compound 26. 5-(1H-pyrazol-4-yl)-N-(pyridin-4-yl)-1H-indazole-3-carboxamide

[Reaction Scheme 29]

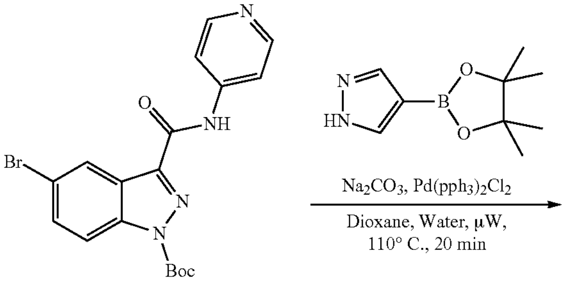

20-086

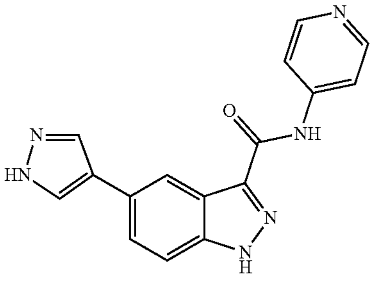

compound 29

A solution of $Na_2CO_3$ (22.9 mg, 0.216 mmol) in water was introduced into a suspension of 20-086 (30.0 mg, 0.0719 mmol), a palladium catalyst (5.04 mg, 0.00719 mmol), and 4-(4,4,5,5-tetramethyl-1,3,2-dioxaborolan-2-yl)-1H-pyrazole (15.4 mg, 0.0863 mmol) in dioxane, followed by purging with nitrogen for 5 minutes. The reaction mixture was exposed to microwaves at 110° C. for 20 minutes. The crude reaction mixture was diluted with 10 mL of water, followed by extraction with 30 mL of ethyl acetate. The organic layers thus obtained were pooled, dried over $Na_2SO_4$, and concentrated in a vacuum to give a crude mixture. Purification by column chromatography using DCM/MeOH 10% as an eluent afforded Compound 26 as a white solid (7.9 mg, 0.0260 mmol, 35%).

LC/MS 305.3[M+H]

$^1$H NMR (400 MHz, DMSO-$d_6$) δ 13.90 (s, 1H), 12.99 (s, 1H), 10.93-10.70 (m, 1H), 8.52-8.42 (m, 2H), 8.32-8.22 (m, 1H), 8.02-7.89 (m, 3H), 7.86-7.73 (m, 2H), 7.70-7.58 (m, 1H).

Compound 27. N-(pyridin-4-yl)-5-(1,3,5-trimethyl-1H-pyrazol-4-yl)-1H-indazole-3-carboxamide

[Reaction Scheme 27]

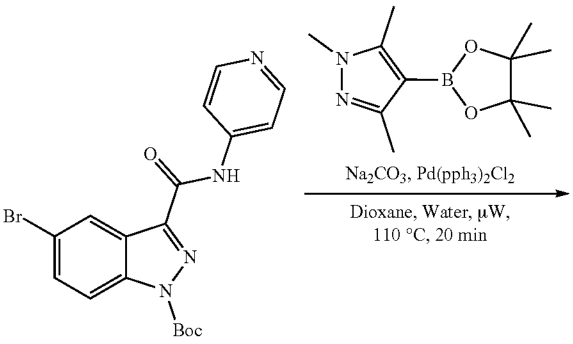

20-086

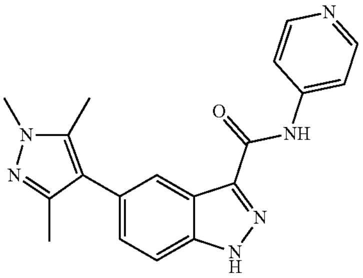

compound 27

A solution of $Na_2CO_3$ (22.9 mg, 0.216 mmol) in water was introduced into a suspension of 20-086 (30.0 mg, 0.0719 mmol), a palladium catalyst (5.04 mg, 0.00719 mmol), and 1,3,5-trimethyl-4-(4,4,5,5-tetra methyl-1,3,2-dioxaborolan-2-yl)-1H-pyrrazole (20.4 mg, 0.0863 mmol) in dioxane, followed by purging with nitrogen for 5 minutes. The reaction mixture was exposed to microwaves at 110° C. for 20 minutes. The resulting crude mixture was diluted in 10 ml of water before extraction with 30 mL of ethyl acetate. The organic layers thus obtained were pooled, dried over $Na_2SO_4$, and concentrated in a vacuum to give a crude mixture. Purification by column chromatography using DCM/MeOH 10%) as an eluent afforded Compound 27 (6.60 mg, 0.0191 mmol, 27%).

$^1$H NMR (300 MHz, DMSO-$d_6$) δ 13.95 (s, 1H), 10.78 (s, 1H), 8.47 (d, J=5.5 Hz, 2H), 8.05 (s, 1H), 7.94 (d, J=6.0 Hz, 2H), 7.73 (d, J=8.6 Hz, 1H), 7.39 (d, J=8.7 Hz, 1H), 3.74 (s, 3H), 2.25 (s, 3H), 2.16 (s, 3H).

Compound 28. 5-(1-isopropyl-1H-pyrazol-4-yl)-N-(pyridin-4-yl)-1H-indazole-3-carboxamide

[Reaction Scheme 28]

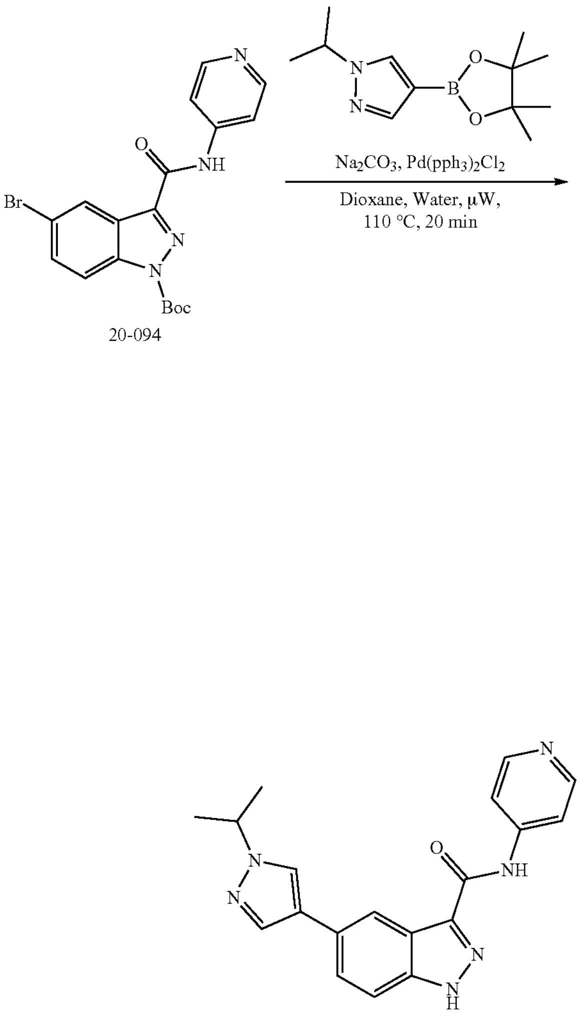

20-094 compound 28

A solution of $Na_2CO_3$ (19.0 mg, 0.180 mmol) in water was introduced into a suspension of 20-094 (30.0 mg, 0.0719 mmol), a palladium catalyst (5.05 mg, 0.00719 mmol), and 1-isopropyl-4-(4,4,5,5-tetramethyl-1,3,2-dioxaborolan-2-yl)-1H-pyrazole (20.4 mg, 0.0863 mmol) in dioxane, followed by purging with nitrogen for 5 minutes. The reaction mixture was exposed to microwaves at 110° C. for 20 minutes. The resulting crude mixture was diluted in 10 ml of water before extraction with 30 mL of ethyl acetate. The organic layers thus obtained were pooled, dried over $Na_2SO_4$, and concentrated in a vacuum to give a crude mixture. Purification by column chromatography using DCM/MeOH 5% as an eluent afforded Compound 28 as a white solid (6.70 mg, 0.0193 mmol, 27%).

$^1H$ NMR (300 MHz, DMSO-$d_6$) δ 13.89 (s, 1H), 10.76 (s, 1H), 8.48 (d, J=5.9 Hz, 2H), 8.35 (s, 1H), 8.31 (s, 1H), 7.97-7.92 (m, 2H), 7.90 (s, 1H), 7.73 (d, J=1.6 Hz, 1H), 7.67 (d, J=8.7 Hz, 1H), 4.59-4.51 (m, 1H), 1.48 (d, J=6.7 Hz, 6H).

Compound 29. 5-(1-Methyl-1H-pyrazol-4-yl)-N-(pyridin-4-yl)-1H-indazole-3-carboxamide

[Reaction Scheme 29]

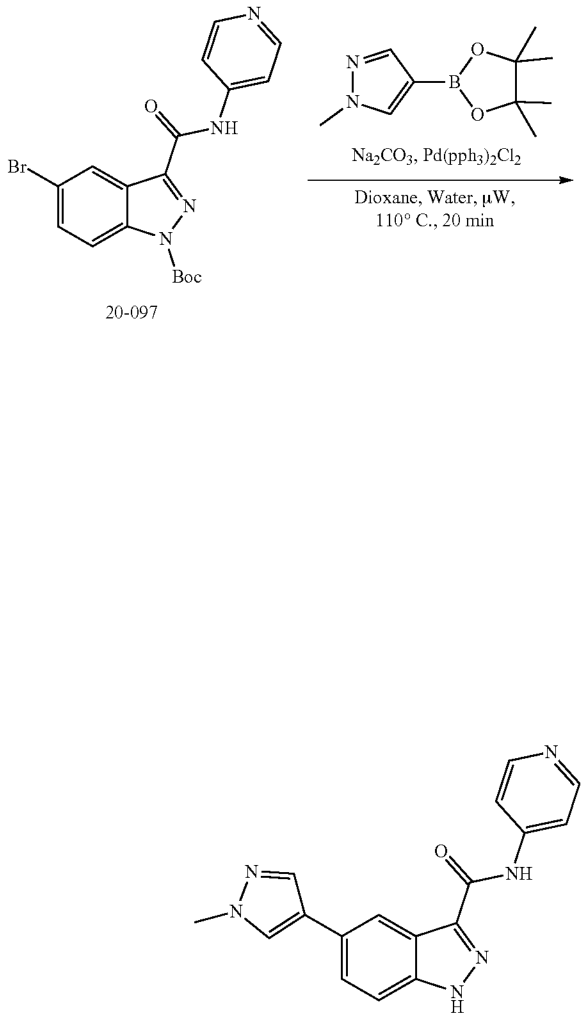

20-097 compound 29

A solution of $Na_2CO_3$ (22.9 mg, 0.216 mmol) in water was introduced into a suspension of 20-097 (30.0 mg, 0.0719 mmol), a palladium catalyst (5.04 mg, 0.00719 mmol), and 1-methyl-4-(4,4,5,5-tetramethyl-1,3,2-dioxaborolan-2-yl)-1H-pyrrazole (18.0 mg, 0.0863 mmol) in dioxane, followed by purging with nitrogen for 5 minutes. The reaction mixture was exposed to microwaves at 110° C. for 20 minutes. The resulting crude mixture was diluted in 10 ml of water before extraction with 30 mL of ethyl acetate. The organic layers thus obtained were pooled, dried over $Na_2SO_4$, and concentrated in a vacuum to give a crude mixture. Purification by column chromatography using DCM/MeOH 10% as an eluent afforded Compound 29 as a yellow solid (8.70 mg, 0.0273 mmol, 38%).

$^1H$ NMR (300 MHz, DMSO-$d_6$) δ 13.89 (s, 1H), 10.76 (s, 1H), 8.47 (d, J=6.1 Hz, 2H), 8.32 (s, 1H), 8.22 (s, 1H), 7.96-7.91 (m, 2H), 7.89 (d, J=0.9 Hz, 1H), 7.73-7.65 (m, 2H), 3.89 (s, 3H).

Compound 30. tert-butyl 5-(1-(1-(tert-butoxycarbonyl)piperidin-4-yl)-1H-pyrazol-4-yl)-3-(pyridin-4-ylcarbamoyl)-1H-indazole-1-carboxylate vacuum to give a crude mixture. Purification by column chromatography using MeOH/MC 5% as an eluent afforded 20-091 as a white solid (15 mg of mixture compound).

[Reaction Scheme 30]

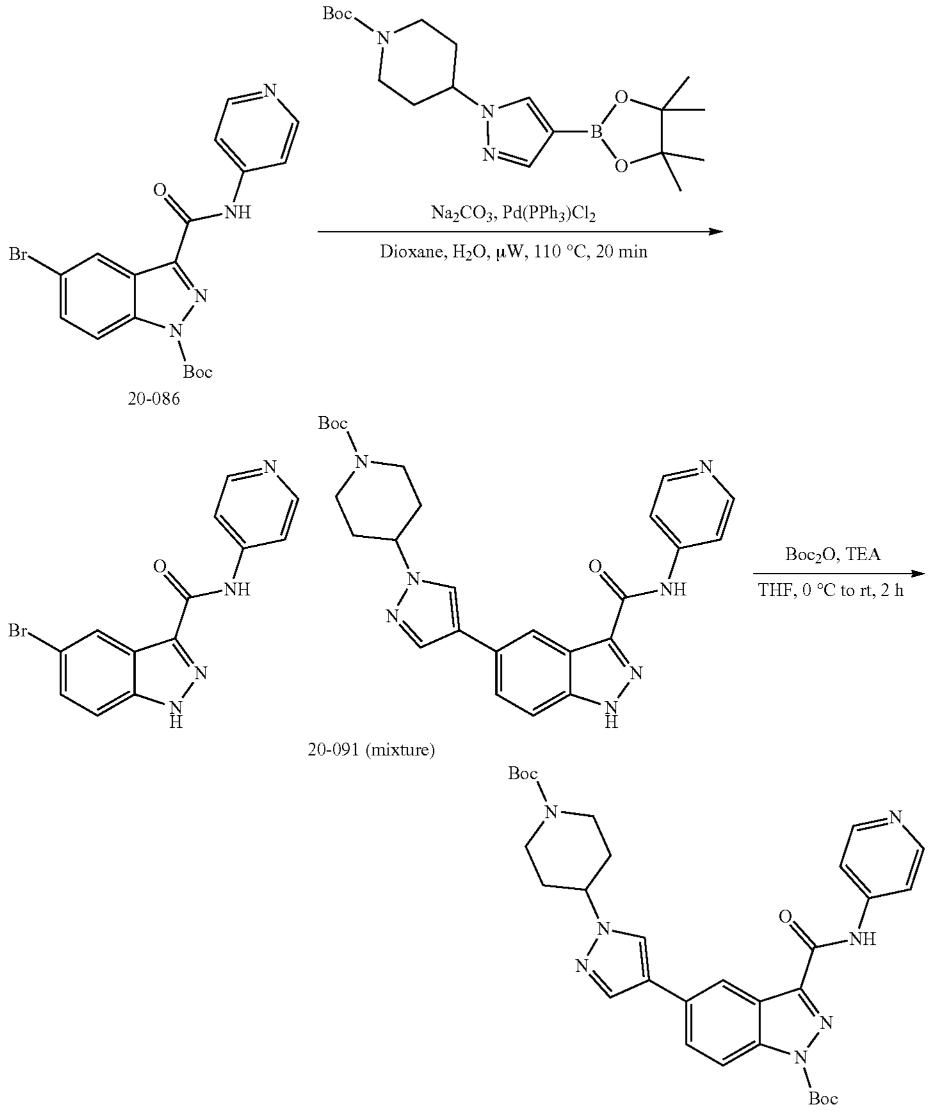

20-086

20-091 (mixture)

compound 30

1) Synthesis of tert-butyl 4-(4-(3-(pyridin-4-ylcarbamoyl)-1H-indazol-5-yl)-1H-pyrazol-1-yl)piperidine-1-carboxylate A solution of $Na_2CO_3$ (31.8 mg, 0.300 mmol) in water was introduced into a suspension of 20-086 (50.0 mg, 0.120 mmol), a palladium catalyst (8.42 mg, 0.0120 mmol), and tert-butyl 4-(4-(4,4,5,5-tetramethyl-1,3,2-dioxaborolan-2-yl)-1H-pyrazol-1-yl)piperidine-1-carboxylate (54.3 mg, 0.144 mmol) in dioxane, followed by purging with nitrogen for 15 minutes. The reaction mixture was exposed to microwaves at 110° C. for 20 minutes. The resulting crude mixture was diluted in 10 ml of water before extraction with 30 mL of ethyl acetate (2×15 mL). The organic layers thus obtained were pooled, dried over $Na_2SO_4$, and concentrated in a

*A mixture (desired product and deprotected starting material) was obtained.

$^1H$ NMR (400 MHz, DMSO-$d_6$) δ 14.01 (d, J=98.6 Hz, 1H), 10.80 (d, J=34.9 Hz, 1H), 8.47 (d, J=4.7 Hz, 2H), 8.39-8.34 (m, 1H), 7.99-7.89 (m, 3H), 7.86-7.58 (m, 4H), 4.46-4.32 (m, 1H), 4.19-3.97 (m, 2H), 3.10-2.82 (m, 2H), 2.16-2.00 (m, 2H), 1.92-1.75 (m, 2H).

2) Synthesis of tert-butyl 5-(1-(1-(tert-butoxycarbonyl)piperidin-4-yl)-1H-pyrazol-4-yl)-3-(pyridin-4-ylcarbamoyl)-1H-indazole-1-carboxylate To a solution of 20-091 (10.0 mg) in THF (1 mL) were added $Boc_2O$ (8.95 mg, 0.0410 mmol) and TEA (7.15 uL 0.0513 mmol) over 2 hours with the temperature elevated from 0° C. to room temperature. When the reaction was completed as monitored by TLC, the reaction mixture was concentrated by evaporation and added with EtOAc (20 mL). The organic layer was washed with water. The organic layers thus obtained were pooled and concentrated at a reduced pressure to give a crude mixture. Purification by column chromatography using MeOH/MC 7% as an eluent afforded Compound 30 as a white solid (5.1 mg, 0.0087 mmol, 84%).

*According to previous NMR data, the product yield was regarded to be in mixture of 1:1 with the starting material.

$^1$H NMR (400 MHz, DMSO-$d_6$) δ 11.04 (s, 1H), 8.53 (d, J=5.4 Hz, 2H), 8.45 (s, 1H), 8.36 (d, 1H), 8.11 (d, J=8.8, 0.8 Hz, 1H), 8.00-7.95 (m, 2H), 7.91 (d, 2H), 4.51-4.30 (m, 1H), 4.07 (d, J=12.5 Hz, 2H), 3.04-2.81 (m, 2H), 2.14-2.02 (m, 2H), 1.91-1.78 (m, 2H), 1.72 (s, 9H), 1.43 (s, 9H).

Compound 31. tert-butyl 5-(4-(4-(tert-butoxycarbonyl)piperazine-1-carbonyl)phenyl)-3-(pyridin-4-ylcarbamoyl)-1H-indazole-1-carboxylate

[Reaction Scheme 31]

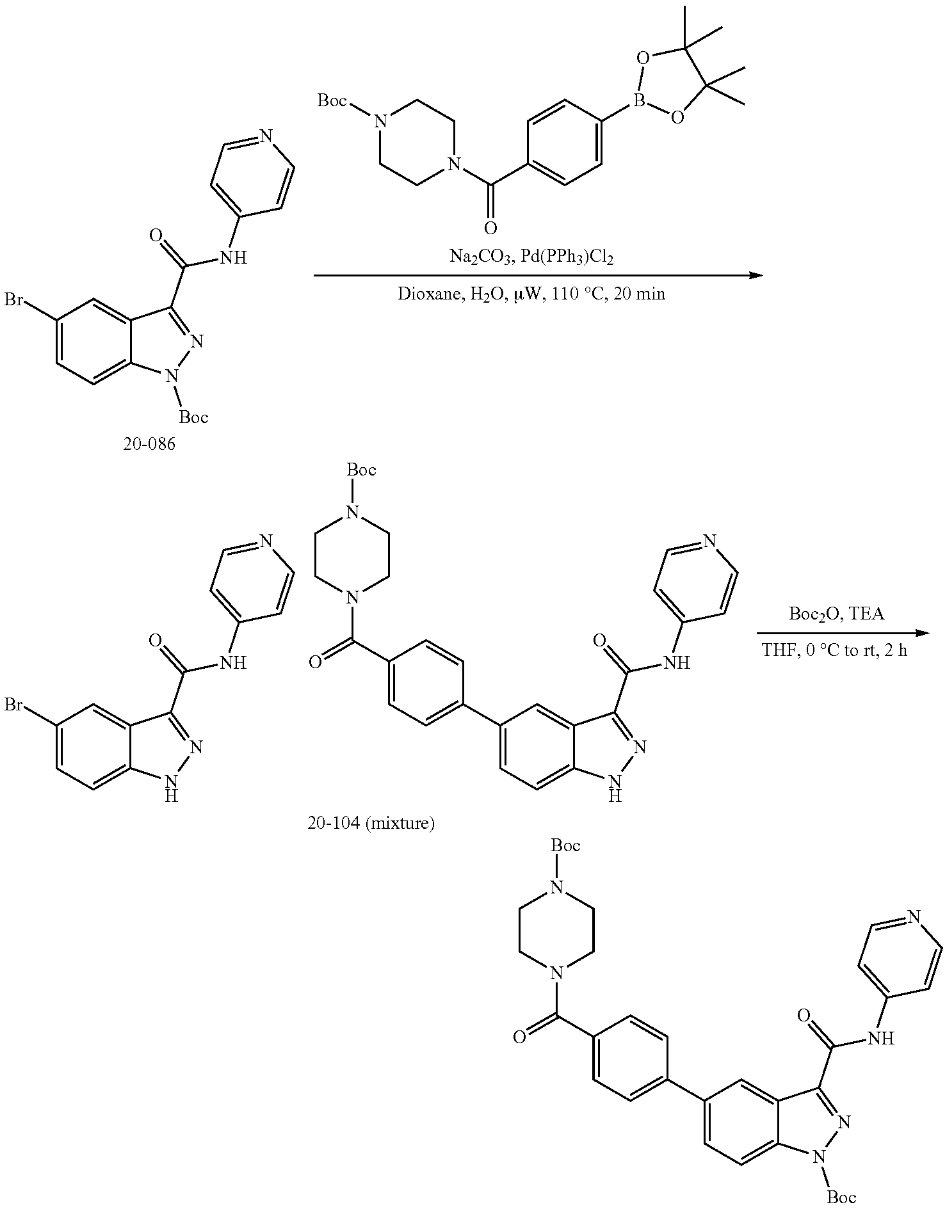

20-086

20-104 (mixture)

compound 31

1) Synthesis of tert-butyl 4-(4-(3-(pyridin-4-ylcarbamoyl)-1H-indazol-5-yl)benzoyl) piperazine-1-carboxylate A solution of $Na_2CO_3$ (31.8 mg, 0.300 mmol) in water was introduced into a suspension of 20-086 (50.0 mg, 0.120 mmol), a palladium catalyst (8.42 mg, 0.0120 mmol), and tert-butyl 4-(4-(4,4,5,5-tetramethyl-1,3,2-dioxaborolan-2-yl)benzoyl)piperazine-1-carboxylate (40.9 mg, 0.144 mmol)

in dioxane, followed by purging with nitrogen for 15 minutes. The reaction mixture was exposed to microwaves at 110° C. for 20 minutes. The resulting crude mixture was diluted in 10 ml of water before extraction with 30 mL of ethyl acetate (2×15 mL). The organic layers thus obtained were pooled, dried over $Na_2SO_4$, and concentrated in a vacuum to give a crude mixture. Purification by column chromatography using MeOH/MC 5% as an eluent afforded 20-104 as a yellow solid (10 mg, 0.0190 mmol, 16%).

According to LCMS data, a mixture of the Boc-deprotected starting material and the desired production was observed.

2) Synthesis of tert-butyl 5-(4-(4-(tert-butoxycarbonyl)piperazine-1-carbonyl) phenyl)-3-(pyridin-4-ylcarbamoyl)-1H-indazole-1-carboxylate To a solution of 20-104 mixture (10.0 mg) in THE (1 mL) were added $Boc_2O$ (16.6 mg, 0.0760 mmol) and TEA (13.3 uL 0.0950 mmol) over 2 hours with the temperature elevated from 0° C. to room temperature. When the reaction was completed as monitored by TLC, the reaction mixture was concentrated by evaporation and added with EtOAc (20 mL). The organic layer was washed with water. The organic layers thus obtained were pooled and concentrated at a reduced pressure to give a crude mixture. Purification by column chromatography using MeOH/MC 7% as an eluent afforded Compound 31 as a white solid (7.7 mg, 0.012 mmol, 65%).

*According to previous NMR data, the product yield was regarded to be in mixture of 1:1 with the starting material.

$^1$H NMR (400 MHz, DMSO-$d_6$) δ 11.09 (s, 1H), 8.53 (d, 2H), 8.51 (s, 1H), 8.24 (d, J=8.8, 0.8 Hz, 1H), 8.08 (dd, J=8.9, 1.8 Hz, 1H), 7.92 (d, 2H), 7.84 (d, 2H), 7.57 (d, J=8.3 Hz, 2H), 3.73-3.37 (m, 8H), 1.74 (s, 9H), 1.42 (s, 9H).

Compound 32. tert-butyl 5-(4-((4-(tert-butoxycarbonyl)piperazin-1-yl)methyl)phenyl)-3-(pyridin-4-ylcarbamoyl)-1H-indazole-1-carboxylate

[Reaction Scheme 32]

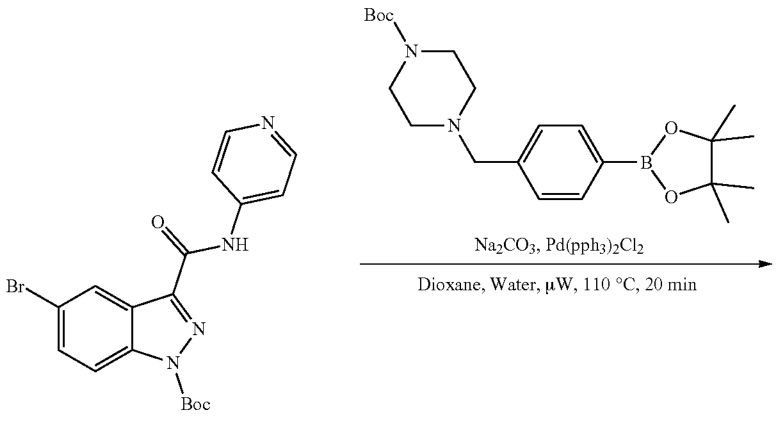

20-097

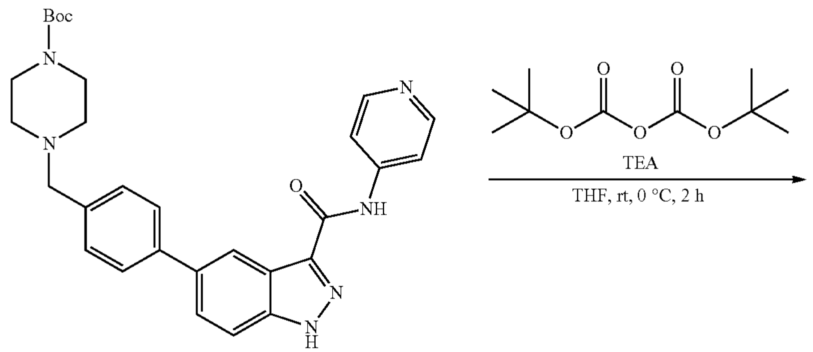

20-010

-continued

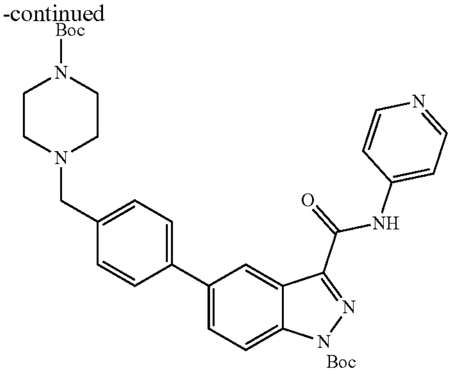

compound 32

1) Synthesis of tert-butyl 4-(4-(3-(pyridin-4-ylcarbamoyl)-1H-indazol-5-yl)benzyl) piperazine-1-carboxylate A solution of $Na_2CO_3$ (31.8 mg, 0.300 mmol) in water was introduced into a suspension of 20-097 (50.0 mg, 0.120 mmol), a palladium catalyst (8.42 mg, 0.0120 mmol), and tert-butyl 4-(4-(4,4,5,5-tetramethyl-1,3,2-dioxaborolan-2-yl)benzyl)piperazine-1-carboxylate (57.9 mg, 0.0863 mmol) in dioxane, followed by purging with nitrogen for 5 minutes. The reaction mixture was exposed to microwaves at 110° C. for 20 minutes. The resulting crude mixture was diluted in 10 ml of water before extraction with 30 mL of ethyl acetate. The organic layers thus obtained were pooled, dried over $Na_2SO_4$, and concentrated in a vacuum to give a crude mixture. Purification by recrystallization in $CHCl_3$ and HEX afforded 20-010 as a white solid (24.3 mg, 0.0474 mmol, 40%).

LC/MS 317.3, 513.6$[M+H]^+$, mixture with De-Boc $^1$H NMR (300 MHz, DMSO-$d_6$) δ 14.13 (s, 1H), 10.83 (d, J=9.9 Hz, 1H), 8.48 (d, J=6.2 Hz, 2H), 8.37 (d, J=1.7 Hz, 1H), 7.92 (d, J=6.5 Hz, 2H), 7.79 (s, 1H), 7.70 (d, J=8.9 Hz, 1H), 7.64-7.57 (m, 1H), 7.43 (d, J=7.9 Hz, 1H), 3.54 (s, 1H), 1.39 (s, 4H), 1.24 (s, 3H).

2) Synthesis of tert-butyl 5-(4-((4-(tert-butoxycarbonyl)piperazin-1-yl)methyl) phenyl)-3-(pyridin-4-ylcarbamoyl)-1H-indazole-1-carboxylate To 20-010 (20.0 mg, 0.0390 mmol) in 1 mL of THE were added di-tert-butyl Bicarbonate (17.0 mg, 0.0780 mmol) and TEA (9.87 mg, 0.0975 mmol) at 0° C. The resulting mixture was stirred at room temperature for 2 hours. The resulting crude mixture was diluted in 5 ml of water before extraction with 10 mL of ethyl acetate. The organic layers thus obtained were pooled and concentrated in a vacuum to give a crude mixture. Purification by column chromatography using DCM/MeOH 5% as an eluent afforded Compound 32 as a white solid (8.2 mg, 0.0134 mmol, 31%).

$^1$H NMR (400 MHz, DMSO-$d_6$) δ 11.06 (s, 1H), 8.55-8.49 (m, 2H), 8.45 (dd, J=1.9, 0.8 Hz, 1H), 8.22-8.18 (m, 1H), 8.03 (dd, J=8.9, 1.8 Hz, 1H), 7.93-7.89 (m, 2H), 7.74-7.69 (m, 2H), 7.48-7.42 (m, 2H), 3.55 (s, 2H), 3.33 (s, 4H), 2.35 (t, J=5.0 Hz, 4H), 1.73 (s, 9H), 1.39 (s, 9H).

Compound 33. 5-(1-Benzyl-1H-pyrazol-4-yl)-N-(pyridin-4-yl)-1H-indazole-3-carboxamide

[Reaction Scheme 33]

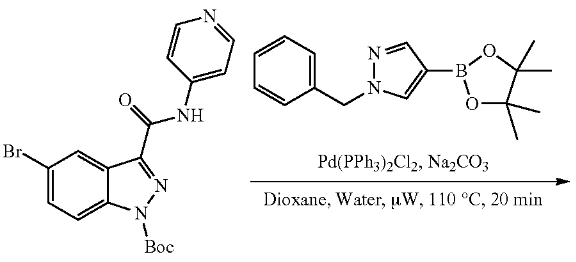

20-107

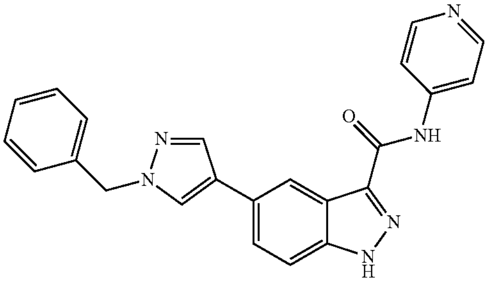

compound 33

A solution of $Na_2CO_3$ (22.9 mg, 0.216 mmol) in water was introduced into a suspension of 20-107 (30.0 mg, 0.0719 mmol), a palladium catalyst (5.04 mg, 0.00719 mmol), and 1-benzyl-4-(4,4,5,5-tetramethyl-1,3,2-dioxaborolan-2-yl)-1H-pyrazole (24.5 mg, 0.0863 mmol) in dioxane, followed by purging with nitrogen for 5 minutes. The reaction mixture was exposed to microwaves at 110° C. for 20 minutes. The resulting crude mixture was diluted in 10 ml of water before extraction with 30 mL of ethyl acetate. The organic layers thus obtained were pooled, dried over $Na_2SO_4$, and concentrated in a vacuum to give a crude mixture. Purification by column chromatography using DCM/MeOH 10% as an eluent afforded Compound 33 as a white solid (12.6 mg, 0.0319 mmol, 44%).

LC/MS 395.4$[M+H]+$

1H NMR (300 MHz, DMSO-d6) δ 13.90 (s, 1H), 10.77 (s, 1H), 8.48 (d, J=5.3 Hz, 2H), 8.40 (s, 1H), 8.35 (s, 1H), 8.00-7.90 (m, 3H), 7.77-7.62 (m, 2H), 7.42-7.25 (m, 5H), 5.38 (s, 2H).

Compound 34. 5-(Furan-3-yl)-N-(pyridin-4-yl)-1H-indazole-3-carboxamide

[Reaction Scheme 34]

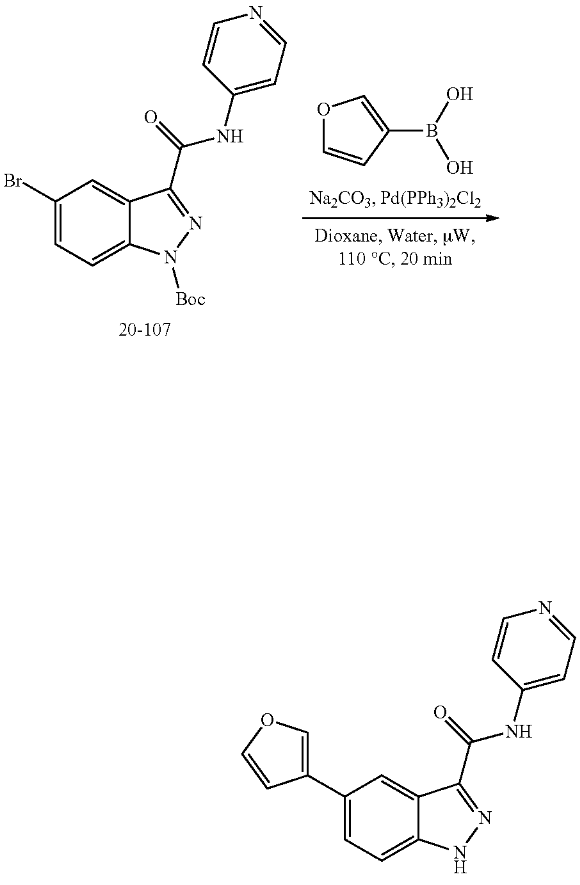

20-107 compound 34

A solution of $Na_2CO_3$ (19.0 mg, 0.180 mmol) in water was introduced into a suspension of 20-107 (30.0 mg, 0.0719 mmol), a palladium catalyst (5.05 mg, 0.00719 mmol), and furan-3-yl boronic acid (9.66 mg, 0.0863 mmol) in dioxane, followed by purging with nitrogen for 5 minutes. The reaction mixture was exposed to microwaves at 110° C. for 20 minutes. The resulting crude mixture was diluted in 10 ml of water before extraction with 30 mL of ethyl acetate. The organic layers thus obtained were pooled, dried over $Na_2SO_4$, and concentrated in a vacuum to give a crude mixture. Purification by recrystallization in $CHCl_3$ and HEX afforded Compound 34 as a brown solid (9.3 mg, 0.0306 mmol, 43%).

LC/MS 305.4[M+H]+.

1H NMR (400 MHz, DMSO-d6) δ 13.94 (s, 1H), 10.78 (s, 1H), 8.48 (d, J=5.5 Hz, 2H), 8.36 (s, 1H), 8.26 (d, J=1.3 Hz, 1H), 7.97-7.92 (m, 2H), 7.79 (t, J=1.7 Hz, 1H), 7.75 (d, J=1.6 Hz, 1H), 7.72 (s, 1H), 7.02 (d, J=1.7 Hz, 1H).

Compound 35. tert-butyl 5-(1-(tert-butoxycarbonyl)-1,2,3,6-tetrahydropyridin-4-yl)-3-(pyridin-4-ylcarbamoyl)-1H-indazole-1-carboxylate

[Reaction Scheme 35]

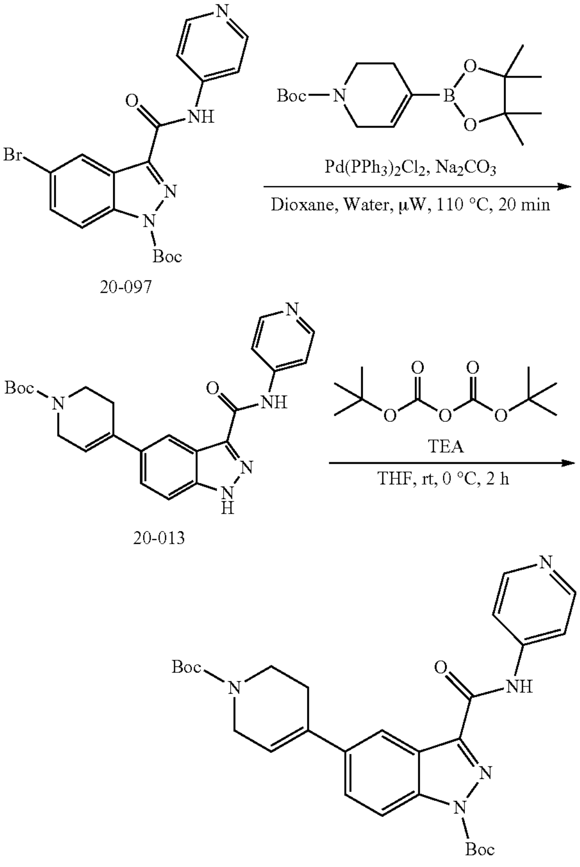

20-097

20-013 compound 35

1) Synthesis of tert-butyl 4-(3-(pyridin-4-ylcarbamoyl)-1H-indazol-5-yl)-3,6-dihydro pyridine-1(2H)-carboxylate A solution of $Na_2CO_3$ (12.7 mg, 0.120 mmol) in water was introduced into a suspension of 20-097 (20.0 mg, 0.0479 mmol), a palladium catalyst (3.36 mg, 0.00479 mmol), and tert-butyl 4-(4,4,5,5-tetramethyl-1,3,2-dioxaborolan-2-yl)-3,6-dihydropyridine-1(2H)-carboxylate (17.8 mg, 0.0575 mmol) in dioxane, followed by purging with nitrogen for 5 minutes. The reaction mixture was exposed to microwaves at 110° C. for 20 minutes. The resulting crude mixture was diluted in 10 ml of water before extraction with 30 mL of ethyl acetate. The organic layers thus obtained were pooled, dried over $Na_2SO_4$, and concentrated in a vacuum to give a crude mixture. Purification by column chromatography using DCM/MeOH 10% as an eluent afforded 20-013 as a white solid (9.5 mg, 0.0226 mmol, 47%).

LC/MS 319.2, 420.5[M+H]+, Mixture with De-Boc.

1H NMR (400 MHz, DMSO-d6) δ 13.91 (s, OH), 10.76 (s, OH), 8.50-8.44 (m, 1H), 7.93 (td, J=4.4, 1.6 Hz, 1H), 7.73-7.58 (m, 1H), 6.23 (s, OH), 4.05 (s, 1H), 3.60 (t, J=5.6 Hz, 1H), 2.57 (s, 1H), 1.45 (s, 4H).

2) Synthesis of tert-butyl 5-(1-(tert-butoxycarbonyl)-1,2,3,6-tetrahydropyridin-4-yl)-3-(pyridin-4-ylcarbamoyl)-1H-indazole-1-carboxylate Di-tert-butyl Bicarbonate (8.64 mg, 0.0396 mmol) and TEA (5.01 mg, 0.0495 mmol) were added to 20-013 (8.30 mg, 0.0198 mmol) in 1 mL of THF at 0° C. The resulting mixture was stirred at room temperature for 2 hours. The resulting crude mixture was diluted in 5 ml of water before extraction with 10 mL of ethyl acetate. The organic layers thus obtained were pooled and concentrated in a vacuum to give a crude mixture. Purification by column chromatography using DCM/MeOH 10% as an eluent afforded Compound 35 as a white solid (5.8 mg, 0.0112 mmol, 56%).

LC/MS 520.6[M+H]+

1H NMR (400 MHz, DMSO-d6) δ 11.02 (s, 1H), 8.55-8.49 (m, 2H), 8.20 (d, J=1.8 Hz, 1H), 8.09 (d, J=8.9 Hz, 1H), 7.92-7.88 (m, 2H), 7.87-7.83 (m, 1H), 6.29 (s, 1H), 4.05 (s, 2H), 3.59 (t, J=5.5 Hz, 2H), 2.56 (s, 2H), 1.71 (s, 9H), 1.44 (s, 9H).

Compound 36. 5-(1-propyl-1H-pyrazol-4-yl)-N-(pyridin-4-yl)-1H-indazole-3-carboxamide

[Reaction Scheme 36]

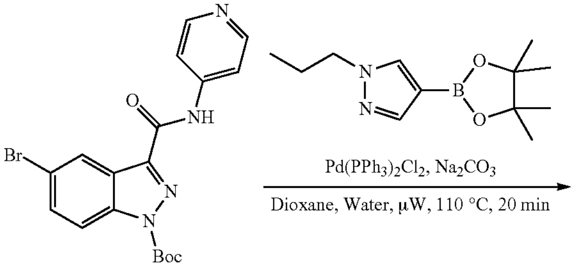

20-107

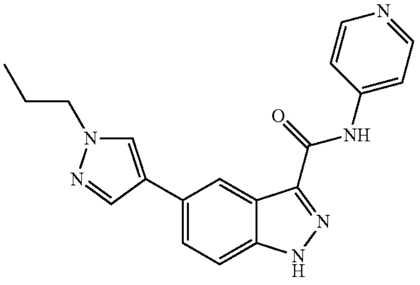

compound 36

A solution of $Na_2CO_3$ (17.2 mg, 0.162 mmol) in water was introduced into a suspension of 20-107 (27.0 mg, 0.0647 mmol), a palladium catalyst (5.04 mg, 0.00719 mmol) and 1-propyl-4-(4,4,5,5-tetra methyl-1,3,2-dioxaborolan-2-yl)-1H-pyrazole (24.5 mg, 0.0863 mmol) in dioxane, followed by purging with nitrogen for 5 minutes. The reaction mixture was exposed to microwaves at 110° C. for 20 minutes. The resulting crude mixture was diluted in 15 ml of water before extraction with ethyl acetate (3×15 ml). The organic layers thus obtained were pooled, dried over $Na_2SO_4$, and concentrated in a vacuum to give a crude mixture. Purification by column chromatography using DCM/MeOH 5% as an eluent afforded Compound 36 as a white solid (5.90 mg, 0.0170 mmol, 28%).

LC/MS 347.5[M+H]+

1H NMR (300 MHz, DMSO-d6) δ 13.90 (s, 1H), 10.77 (s, 1H), 8.48 (d, J=5.5 Hz, 1H), 8.33 (d, J=5.2 Hz, 1H), 8.27 (s, OH), 8.00-7.92 (m, 1H), 7.91 (s, OH), 7.76-7.65 (m, 1H), 4.11 (t, J=6.9 Hz, 1H), 1.85 (q, J=7.2 Hz, 1H), 0.87 (t, J=7.3 Hz, 2H).

Compound 37. 5-(2,3-Dihydrobenzo[b][1,4]dioxin-6-yl)-N-(pyridin-4-yl)-1-(tetrahydro-2H-pyran-2-yl)-1H-indazole-3-carboxamide

[Reaction Scheme 37]

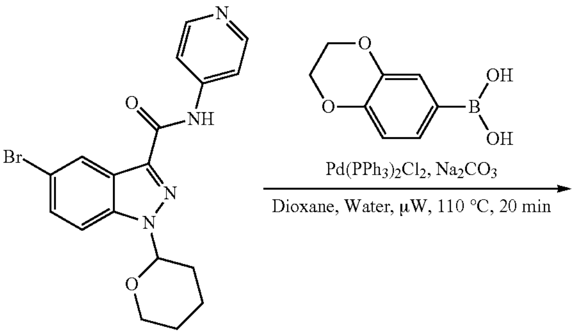

20-117

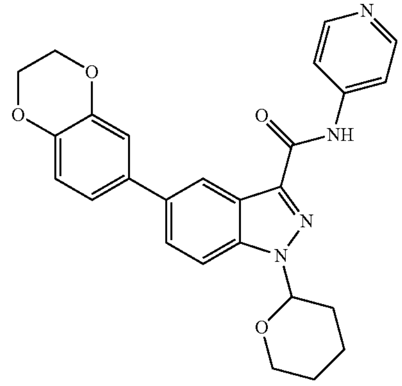

compound 37

5-(2,3-dihydrobenzo[b][1,4]dioxin-6-yl)-N-(pyridin-4-yl)-1-(tetrahydro-2H-pyran-2-yl)-1H-indazole-3-carboxamide A solution of $Na_2CO_3$ (19.8 mg, 0.187 mmol) in water was introduced into a suspension of 20-117 (30.0 mg, 0.0748 mmol), a palladium catalyst (5.25 mg, 0.00748 mmol) and (2,3-dihydrobenzo[b][1,4]dioxin-6-yl)boronic acid (16.1 mg, 0.0897 mmol) in dioxane, followed by purging with nitrogen for 5 minutes. The reaction mixture was exposed to microwaves at 110° C. for 20 minutes. The crude reaction mixture was filtered with dioxane and concentrated in a vacuum to give a crude mixture. Purification by column chromatography using DCM/MeOH 5% as an eluent afforded Compound 37 as a yellow solid (11.9 mg, 0.0261 mmol, 35%).

LC/MS 457.5[M+H]+

1H NMR (400 MHz, DMSO-d6) δ 10.64 (s, 1H), 8.54-8.47 (m, 2H), 8.34 (dd, J=1.8, 0.8 Hz, 1H), 7.98-7.90 (m, 3H), 7.79 (dd, J=8.9, 1.8 Hz, 1H), 7.22-7.17 (m, 2H), 7.01-6.97 (m, 1H), 6.04 (dd, J=10.1, 2.3 Hz, 1H), 4.31 (s,

4H), 4.00 (d, J=11.4 Hz, 1H), 3.84 (td, J=11.0, 10.5, 3.9 Hz, 1H), 2.60 (d, J=12.5 Hz, 1H), 2.08 (s, 2H), 1.65 (s, 2H), 1.24 (s, 1H).

Compound 38. tert-butyl 4-(4-(3-(pyridin-4-ylcarbamoyl)-1-(tetrahydro-2H-pyran-2-yl)-1H-indazol-5-yl)benzyl)piperazine-1-carboxylate

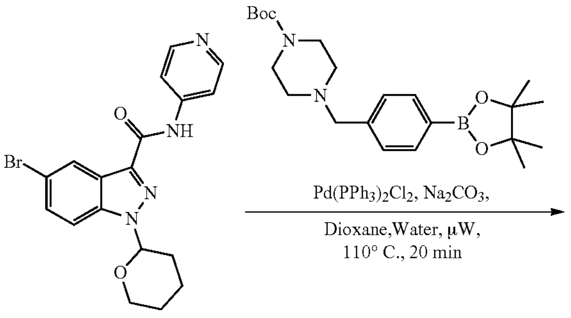

20-117

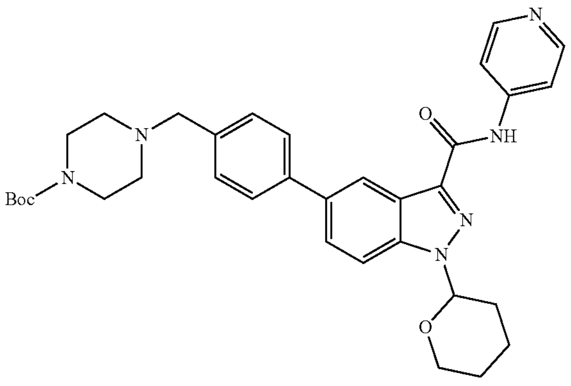

Compound 38

A solution of $Na_2CO_3$ (19.8 mg, 0.187 mmol) in water was introduced into a suspension of 20-117 (30.0 mg, 0.0748 mmol), a palladium catalyst (5.25 mg, 0.00748 mmol) and tert-butyl 4-(4-(4,4,5,5-tetramethyl-1,3,2-dioxaborolan-2-yl)benzyl)piperazine-1-carboxylate (36.1 mg, 0.0897 mmol) in dioxane, followed by purging with nitrogen for 5 minutes. The reaction mixture was exposed to microwaves at 110° C. for 20 minutes. The crude reaction mixture was filtered with dioxane and concentrated in a vacuum to give a crude mixture. Purification by column chromatography using DCM/MeOH 5% as an eluent afforded Compound 38 as a brown solid (23.1 mg, 0.0387 mmol, 52%).

LC/MS 597.7[M+H]+

1H NMR (400 MHz, DMSO-d6) δ 10.65 (s, 1H), 8.53-8.48 (m, 2H), 8.44 (d, J=1.5 Hz, 1H), 8.00 (d, J=8.8 Hz, 1H), 7.95-7.91 (m, 2H), 7.86 (dd, J=8.9, 1.8 Hz, 1H), 7.70 (d, J=8.0 Hz, 2H), 7.45 (d, J=8.0 Hz, 2H), 6.08-6.03 (m, 1H), δ 4.01 (d, J=11.8 Hz, 1H), 3.89-3.80 (m, 1H), 3.55 (s, 2H), 3.41-3.34 (m, 4H), 2.63-2.56 (m, 1H), 2.41-2.26 (m, 4H), 2.13-2.03 (m, 2H), 1.87-1.77 (m, 1H), 1.70-1.60 (m, 2H), 1.40 (s, 9H).

Compound 39. tert-butyl 4-(3-(pyridin-4-ylcarbamoyl)-1-(tetrahydro-2H-pyran-2-yl)-1H-indazol-5-yl)-3,6-dihydropyridine-1(2H)-carboxylate

[Reaction Scheme 39]

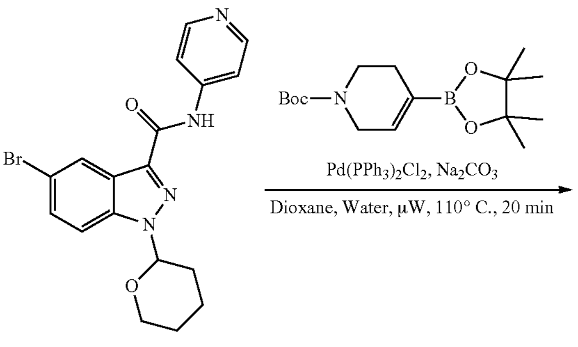

20-117

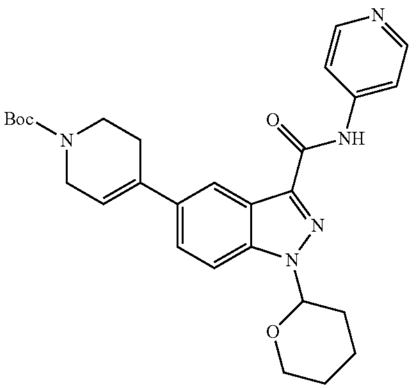

compound 39

A solution of $Na_2CO_3$ (19.8 mg, 0.187 mmol) in water was introduced into a suspension of 20-117 (30.0 mg, 0.0748 mmol), a palladium catalyst (5.25 mg, 0.00748 mmol) and tert-butyl 4-(4,4,5,5-tetramethyl-1,3,2-dioxaborolan-2-yl)-3,6-dihydropyridine-1(2H)-carboxylate (27.7 mg, 0.0897 mmol) in dioxane, followed by purging with nitrogen for 5 minutes. The reaction mixture was exposed to microwaves at 110° C. for 20 minutes. The crude reaction mixture was filtered with dioxane and concentrated in a vacuum to give a crude mixture. Purification by column chromatography using DCM/MeOH 5% as an eluent afforded Compound 39 as a yellow solid (26.6 mg, 0.0528 mmol, 71%).

LC/MS 504.4[M+H]+

1H NMR (300 MHz, DMSO-d6) δ 10.62 (s, 1H), 8.51 (d, J=6.1 Hz, 2H), 8.20 (s, 1H), 7.94 (d, J=6.3 Hz, 2H), 7.88 (d, J=9.0 Hz, 1H), 7.75-7.68 (m, 1H), 6.25 (s, 1H), 6.00 (s, OH), 4.03 (d, J=13.0 Hz, 2H), 3.92 (s, 1H), 3.83 (s, 1H), 3.60 (t, J=5.6 Hz, 2H), 2.57 (s, 5H), 2.04 (d, J=14.5 Hz, 3H), 1.65 (s, 2H), 1.45 (s, 9H).

Compound 40. tert-butyl 4-(4-(3-(pyridin-4-ylcarbamoyl)-1-(tetrahydro-2H-pyran-2-yl)-1H-indazol-5-yl)phenyl)piperazine-1-carboxylate

[Reaction Scheme 40]

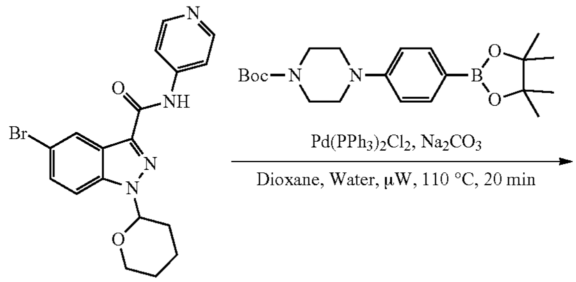

20-117

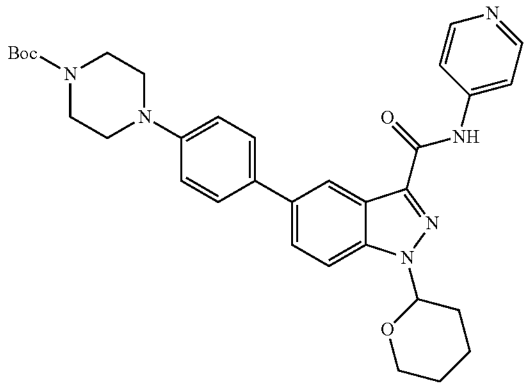

compound 40

A solution of $Na_2CO_3$ (19.8 mg, 0.187 mmol) in water was introduced into a suspension of 20-117 (30.0 mg, 0.0748 mmol), a palladium catalyst (5.25 mg, 0.00748 mmol) and tert-butyl 4-(4-(4,4,5,5-tetramethyl-1,3,2-dioxaborolan-2-yl)phenyl)piperazine-1-carboxylate (34.8 mg, 0.0897 mmol) in dioxane, followed by purging with nitrogen for 5 minutes. The reaction mixture was exposed to microwaves at 110° C. for 20 minutes. The crude reaction mixture was filtered with dioxane and concentrated in a vacuum to give a crude mixture. Purification by column chromatography using DCM/MeOH 5% as an eluent afforded Compound 40 as a yellow solid (20.5 mg, 0.0403 mmol, 54%).

LC/MS 583.7[M+H]+

1H NMR (400 MHz, DMSO-d6) δ 10.75 (s, 1H), 8.56-8.51 (m, 2H), 8.40 (dd, J=1.8, 0.8 Hz, 1H), 8.01-7.98 (m, 3H), 7.99-7.96 (m, 1H), 7.85 (dd, J=8.9, 1.8 Hz, 1H), 7.37 (t, J=7.9 Hz, 1H), 7.23 (t, J=2.1 Hz, 1H), 7.15 (dd, J=7.7, 1.5 Hz, 1H), 6.08 (d, J=2.5 Hz, 1H), 3.99 (d, 1H), 3.86 (d, J=8.4 Hz, 1H), 3.51 (t, J=5.1 Hz, 4H), 3.21 (t, J=5.2 Hz, 4H), 2.62 (d, J=12.3 Hz, 1H), 2.09 (m, 2H), 1.82 (q, J=4.9, 4.4 Hz, 1H), 1.66 (d, J=5.2 Hz, 2H), 1.44 (s, 9H).

Compound 41. 5-(5-Formylfuran-2-yl)-N-(pyridin-4-yl)-1-(tetrahydro-2H-pyran-2-yl)-1H-indazole-3-carboxamide

[Reaction Scheme 41]

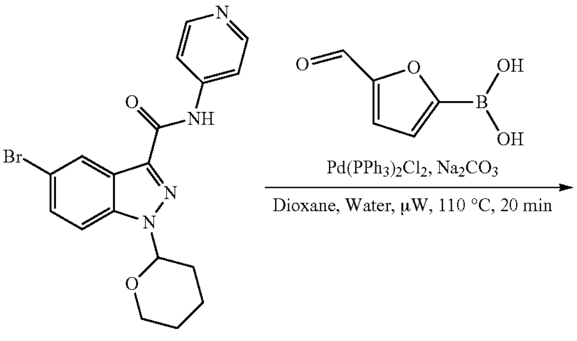

20-117

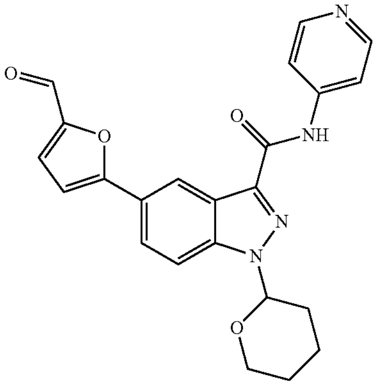

compound 41

A solution of $Na_2CO_3$ (19.8 mg, 0.187 mmol) in water was introduced into a suspension of 20-117 (30.0 mg, 0.0748 mmol), a palladium catalyst (5.25 mg, 0.00748 mmol) and (5-formylfuran-2-yl)boronic acid (27.7 mg, 0.0897 mmol) in dioxane, followed by purging with nitrogen for 5 minutes. The reaction mixture was exposed to microwaves at 110° C. for 20 minutes. The crude reaction mixture was filtered with dioxane and concentrated in a vacuum to give a crude mixture. Purification by column chromatography using DCM/MeOH 5% as an eluent afforded Compound 41 as a brown solid (15.8 mg, 0.0379 mmol, 51%).

LC/MS 417.5[M+H]+

1H NMR (300 MHz, DMSO-d6) δ 10.72 (s, 1H), 9.65 (s, 1H), 8.71 (t, J=1.2 Hz, 1H), 8.52 (s, 2H), 8.07 (d, J=1.5 Hz, 1H), 7.96 (d, J=5.3 Hz, 2H), 7.71 (d, J=3.8 Hz, 1H), 7.42 (d, J=3.7 Hz, 1H), 6.08 (d, J=9.6 Hz, 1H), 4.03 m, 1H), 3.87 (m, J=12.2 Hz, 1H), 2.61 (d, J=13.2 Hz, 1H), 2.09 (m, 2H), 1.82 (m, 1H), 1.66 (m, 2H).

Compound 42. N-(Pyridin-4-yl)-5-(1,2,3,6-tetrahydropyridin-4-yl)-1H-indazole-3-carboxamide

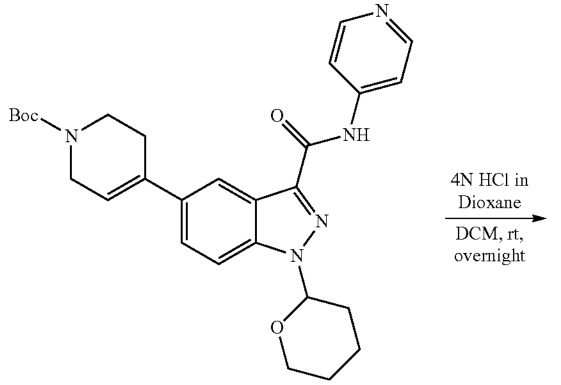

20-023

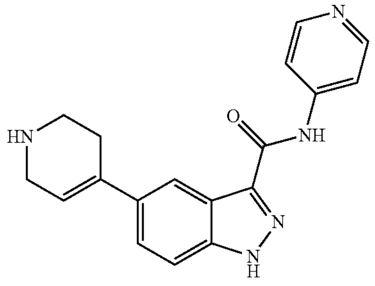

Compound 42

To a solution of 20-023 (22.0 mg, 0.0511 mmol) in DCM (0.5 ml) was added 4N HCl in dioxane (0.25 ml), and the reaction mixture was stirred overnight at room temperature. The crude reaction mixture was diluted with 10 mL of water, followed by extraction with 10 mL of ethyl acetate. The organic layers thus obtained were pooled, added with $NaHCO_3$, and washed with water to afford Compound 42 as a brown solid (3.6 mg, 0.0113 mmol, 40%).

LC/MS 320.4[M+H]+

1H NMR (300 MHz, DMSO-d6) δ 10.76 (s, 1H), 8.57-8.39 (m, 3H), 8.18 (s, 1H), 7.99-7.84 (m, 3H), 7.64 (s, 2H), 6.28 (s, 1H), 3.47-3.41 (m, 2H), 3.04-2.94 (m, 2H), 2.47-2.41 (m, 2H).

Compound 43. 5-(Benzo[b]thiophen-2-yl)-N-(pyridin-4-yl)-1-(tetrahydro-2H-pyran-2-yl)-1H-indazole-3-carboxamide

[Reaction Scheme 43]

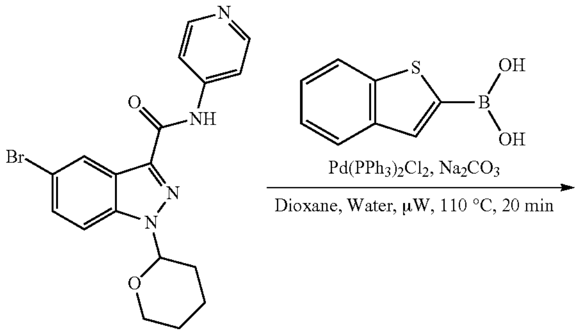

20-117

-continued

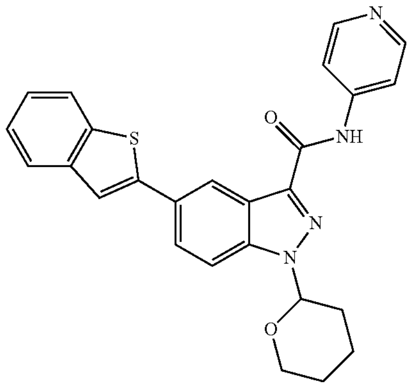

compound 43

A solution of $Na_2CO_3$ (33.1 mg, 0.312 mmol) in water was introduced into a suspension of 20-117 (50.0 mg, 0.125 mmol), a palladium catalyst (8.77 mg, 0.0125 mmol) and benzo[b]thiophen-2-ylboronic acid (23.4 mg, 0.131 mmol) in dioxane, followed by purging with nitrogen for 5 minutes. The reaction mixture was exposed to microwaves at 110° C. for 20 minutes. The crude reaction mixture was filtered with dioxane and concentrated in a vacuum to give a crude mixture. Purification by column chromatography using DCM/MeOH 5% as an eluent afforded Compound 43 as a yellow solid (38.8 mg, 0.0854 mmol, 68%).

LC/MS 455.5[M+H]+

1H NMR (400 MHz, DMSO-d6) δ 10.93 (s, 1H), 8.62-8.56 (m, 2H), 8.55-8.53 (m, 1H), 8.12-8.08 (m, 2H), 8.07-8.05 (m, 2H), 8.03-7.99 (m, 1H), 7.98 (s, 1H), 7.92-7.87 (m, 1H), 7.45-7.34 (m, 2H), 6.08 (dd, J=10.1, 2.4 Hz, 1H), 4.08-3.95 (m, 1H), 3.90-3.71 (m, 1H), 2.70-2.53 (m, 1H), 2.20-2.01 (m, 2H), 1.88-1.77 (m, 1H), 1.72-1.61 (m, 2H).

Compound 44. 5-(2-(dimethylamino)pyrimidin-5-yl)-N-(pyridin-4-yl)-1-(tetrahydro-2H-pyran-2-yl)-1H-indazole-3-carboxamide

[Reaction Scheme 44]

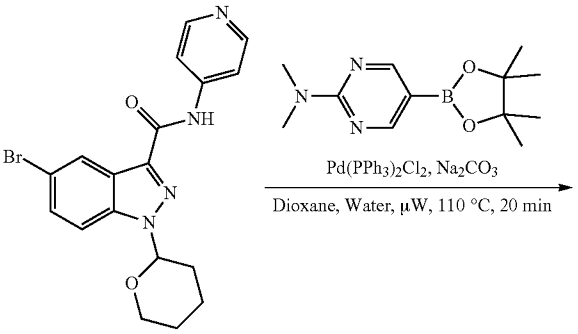

20-117

-continued

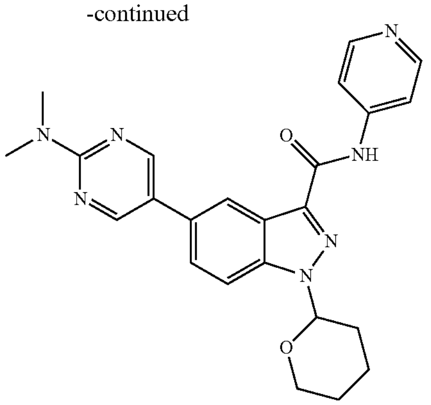

compound 44

A solution of $Na_2CO_3$ (33.1 mg, 0.312 mmol) in water was introduced into a suspension of 20-117 (50.0 mg, 0.125 mmol), a palladium catalyst (8.77 mg, 0.0125 mmol) and N,N-dimethyl-5-(4,4,5,5-tetramethyl-1,3,2-dioxaborolan-2-yl)pyrimidin-2-amine (37.4 mg, 0.150 mmol) in dioxane, followed by purging with nitrogen for 5 minutes. The reaction mixture was exposed to microwaves at 110° C. for 20 minutes. The crude reaction mixture was filtered with dioxane and concentrated in a vacuum to give a crude mixture. Purification by column chromatography using DCM/MeOH 5% as an eluent afforded Compound 44 as a yellow solid (32.5 mg, 0.0733 mmol, 59%).

LC/MS 444.5[M+H]+

1H NMR (300 MHz, DMSO-d6) δ 10.65 (s, 1H), 8.73 (s, 2H), 8.54-8.46 (m, 2H), 8.33 (dd, J=1.8, 0.8 Hz, 1H), 7.98 (dd, J=8.8, 0.9 Hz, 1H), 7.95-7.90 (m, 2H), 7.81 (d, J=1.8 Hz, 1H), 6.04 (dd, J=10.0, 2.3 Hz, 1H), 3.97 (m, 1H), 3.83 (m, J=12.5 Hz, 1H), 3.19 (s, 6H), 2.58 (m, J=10.8 Hz, 1H), 2.08 (m, J=3.4 Hz, 2H), 1.82 (m, 1H), 1.64 (m, 2H).

Compound 45. 5-(6-Formylbenzo[d][1,3]dioxol-5-yl)-N-(pyridin-4-yl)-1-(tetrahydro-2H-pyran-2-yl)-1H-indazole-3-carboxamide

[Reaction Scheme 45]

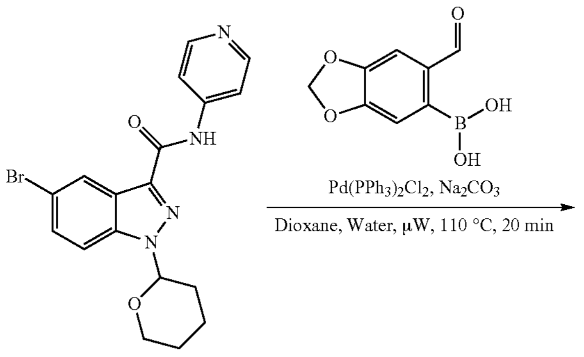

20-117

-continued

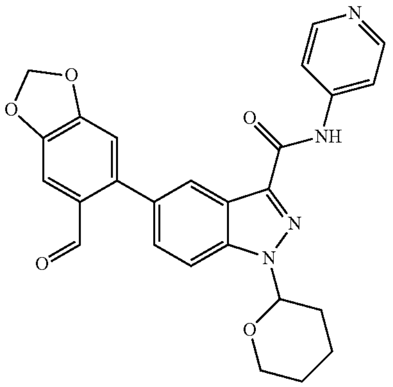

compound 45

A solution of $Na_2CO_3$ (33.1 mg, 0.312 mmol) in water was introduced into a suspension of 20-117 (50.0 mg, 0.125 mmol), a palladium catalyst (8.77 mg, 0.0125 mmol) and (6-formylbenzo[d][1,3]dioxol-5-yl)boronic acid (29.1 mg, 0.150 mmol) in dioxane, followed by purging with nitrogen for 5 minutes. The reaction mixture was exposed to microwaves at 110° C. for 20 minutes. The crude reaction mixture was filtered with dioxane and concentrated in a vacuum to give a crude mixture. Purification by column chromatography using DCM/MeOH 10% as an eluent afforded Compound 45 as a brown solid (48.1 mg, 0.102 mmol, 82%).

LC/MS 471.5[M+H]+

1H NMR (400 MHz, DMSO-d6) δ 10.69 (s, 1H), 9.67 (s, 1H), 8.53-8.46 (m, 2H), 8.17 (dd, J=1.8, 0.8 Hz, 1H), 8.02 (dd, J=8.8, 0.8 Hz, 1H), 7.94-7.90 (m, 2H), 7.64-7.60 (m, 1H), 7.39 (s, 1H), 7.16 (s, 1H), 6.24 (s, 2H), 6.09 (dd, J=10.1, 2.3 Hz, 1H), 4.05-3.97 (m, 1H), 3.90-3.81 (m, 1H), 2.65-2.57 (m, 1H), 2.15-2.04 (m, 2H), 1.88-1.77 (m, 1H), 1.71-1.60 (m, 2H).

Compound 46. 5-(4-(Piperazin-1-yl)phenyl)-N-(pyridin-4-yl)-1H-indazole-3-carboxamide hydrochloride

[Reaction Scheme 46]

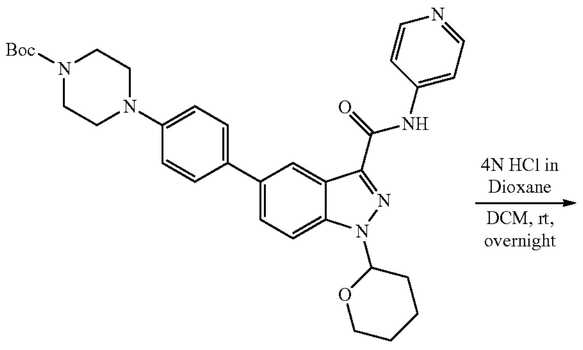

20-025

-continued

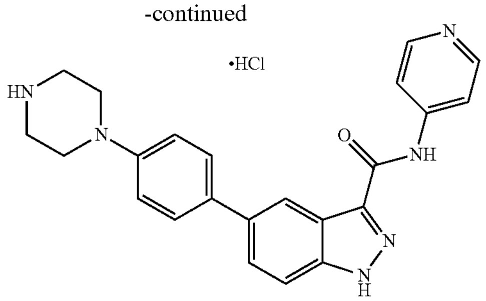

compound 46

To a solution of 20-025 (13.1 mg, 0.0225 mmol) in DCM (0.5 ml) was added 4N HCl in dioxane (0.25 ml), and the reaction mixture was stirred overnight at room temperature. The reaction mixture was concentrated in a vacuum to afford Compound 46 as a beige solid (10.3 mg, 0.0219 mmol, 97%).

LC/MS 399.5[M+H]+

1H NMR (400 MHz, DMSO-d6) δ14.39 (s, 1H), 11.86 (s, 1H), 9.18 (s, 2H), 8.79 (d, J=7.3 Hz, 2H), 8.59-8.48 (m, 2H), 8.41 (d, J=1.3 Hz, 1H), 7.83 (d, J=1.2 Hz, 2H), 7.43-7.36 (m, 1H), 7.28 (s, 1H), 7.21 (d, 1H), 7.05 (dd, J=8.1, 2.5 Hz, 1H), 3.56-3.42 (m, 4H), 3.26 (s, 4H).

Compound 47. 5-(5-Formylfuran-2-yl)-N-(pyridin-4-yl)-1H-indazole-3-carboxamide

[Reaction Scheme 47]

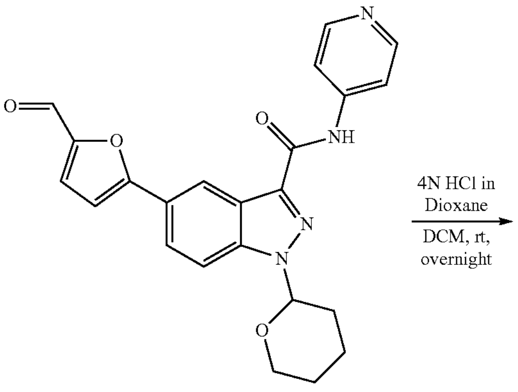

20-026

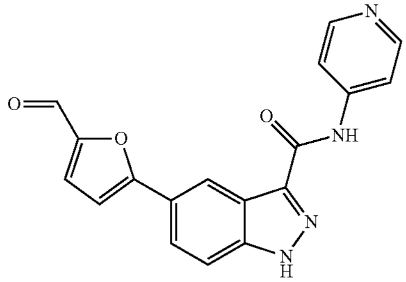

compound 47

To a solution of 20-026 (10.9 mg, 0.0262 mmol) in DCM (0.5 ml) was added 4N HCl in dioxane (0.25 ml), and the reaction mixture was stirred overnight at room temperature. The reaction mixture was concentrated in a vacuum to afford Compound 47 as a blue solid (8.20 mg, 0.0247 mmol, 94%).

1H NMR (400 MHz, DMSO-d6) δ14.50 (s, 1H), 11.86 (s, 1H), 9.65 (s, 1H), 8.78 (d, J=7.0 Hz, 2H), 8.71 (d, J=1.6 Hz, 1H), 8.49 (d, 2H), 8.06 (dd, J=8.8, 1.7 Hz, 1H), 7.88 (d, J=8.8 Hz, 1H), 7.71 (d, J=3.7 Hz, 1H), 7.40 (d, J=3.7 Hz, 1H).

Compound 48. 5-(Benzo[b]thiophen-2-yl)-N-(pyridin-4-yl)-1H-indazole-3-carboxamide

[Reaction Scheme 48]

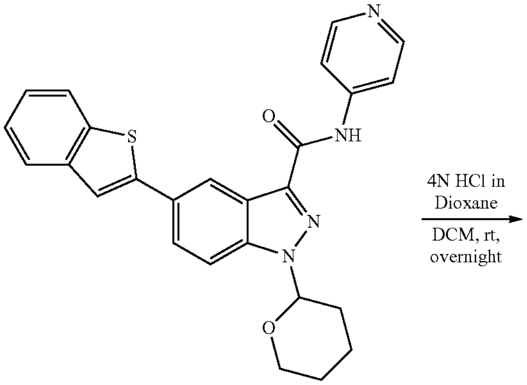

20-032

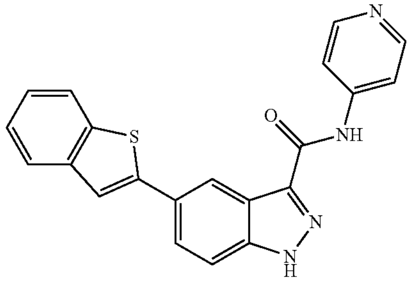

compound 48

To a solution of 20-032 (24.3 mg, 0.0535 mmol) in DCM (0.5 ml) was added 4N HCl in dioxane (0.25 ml), and the reaction mixture was stirred overnight at room temperature. The reaction mixture was concentrated in a vacuum to afford Compound 48 as a yellow solid (16.7 mg, 0.0451 mmol, 84%).

LC/MS 371.4[M+H]+

1H NMR (400 MHz, DMSO-d6) δ 14.47 (s, 1H), 11.87 (s, 1H), 8.79 (d, J=7.1 Hz, 2H), 8.55 (d, J=1.7 Hz, 1H), 8.53-8.48 (m, 2H), 8.02 (ddd, J=9.6, 8.4, 1.6 Hz, 2H), 7.97 (s, 1H), 7.91-7.85 (m, 2H), 7.46-7.36 (m, 2H).

Compound 49. 5-(2-Fluoropyridin-3-yl)-N-(pyridin-4-ylmethyl)-1-(tetrahydro-2H-pyran-2-yl)-1H-indazole-3-carboxamide

[Reaction Scheme 49]

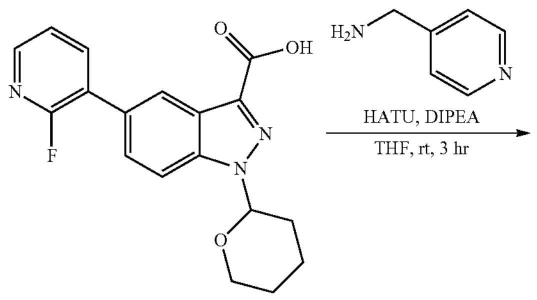

20-028

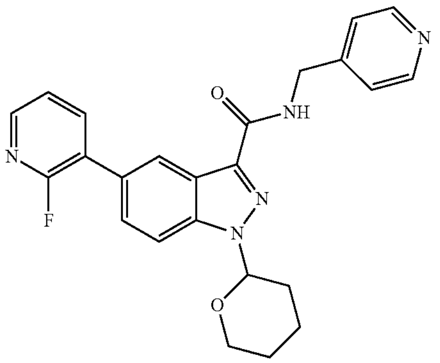

compound 49

To a suspension of 20-028 (50.0 mg, 0.146 mmol) in THF (1 mL) were added DIPEA (56.7 mg, 0.438 mmol) and then HATU (66.5 mg, 0.175 mmol) at room temperature, and the reaction mixture was stirred for 15 minutes. After addition of pyridin-4-yl methanamine (17.4 mg, 0.161 mmol) thereto, the reaction mixture was stirred overnight at room temperature. The residual solvent was evaporated in a vacuum. The resulting crude mixture was diluted in 10 ml of water before extraction with ethyl acetate (3×15 ml). The organic layers thus obtained were pooled, dried over $MgSO_4$, and concentrated in a vacuum to give a crude mixture. Purification by column chromatography using MeOH/DCM 8% as an eluent afforded Compound 49 as a beige solid (31.2 mg, 0.0723 mmol, 50%).

LC/MS 432.6[M+H]+

1H NMR (400 MHz, DMSO-d6) δ 9.16 (t, J=6.3 Hz, 1H), 8.53-8.49 (m, 2H), 8.40-8.38 (m, 1H), 8.26 (dt, J=4.8, 1.5 Hz, 1H), 8.21-8.15 (m, 1H), 7.99 (dd, J=8.9, 0.9 Hz, 1H), 7.74 (dt, J=8.8, 1.7 Hz, 1H), 7.50 (ddd, J=7.0, 4.8, 1.9 Hz, 1H), 7.37-7.33 (m, 2H), 6.04 (dd, J=9.7, 2.4 Hz, 1H), 4.54 (d, J=6.3 Hz, 2H), 3.98-3.91 (m, 1H), 3.86-3.76 (m, 1H), 2.58-2.52 (m, 1H), 2.13-2.02 (m, 2H), 1.85-1.75 (m, 1H), 1.67-1.58 (m, 2H).

Compound 50. 5-(2-(Dimethylamino)pyrimidin-5-yl)-N-(pyridin-4-yl)-1H-indazole-3-carboxamide

[Reaction Scheme 50]

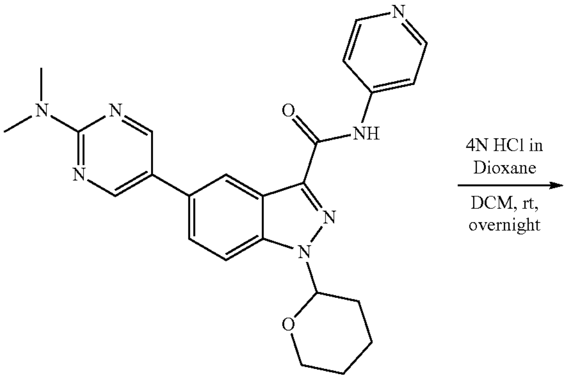

20-033

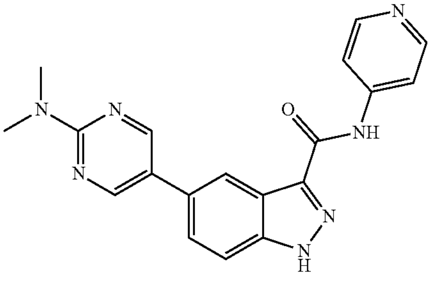

compound 50

To a solution of 20-033 (17.9 mg, 0.0511 mmol) in DCM (0.5 ml) was added 4N HCl in dioxane (0.25 ml), and the reaction mixture was stirred overnight at room temperature. The reaction mixture was concentrated in a vacuum to afford Compound 50 as a yellow solid (16.7 mg, 0.0465 mmol, 84%).

LC/MS 360.5[M+H]+

1H NMR (400 MHz, DMSO-d6) δ 14.39 (s, 1H), 11.85 (s, 1H), 8.78 (d, J=6.8 Hz, 2H), 8.75 (s, 2H), 8.50 (d, J=6.8 Hz, 2H), 8.34 (d, J=1.5 Hz, 1H), 7.86-7.76 (m, 2H), 3.21 (s, 6H).

Compound 51. 5-(2-Fluoropyridin-3-yl)-N-(pyridin-4-ylmethyl)-1H-indazole-3-carboxamide

[Reaction Scheme 51]

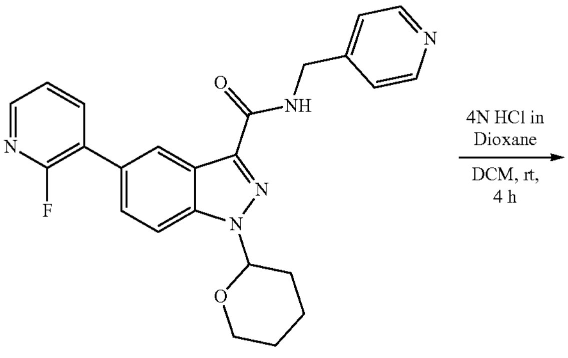

20-040

-continued

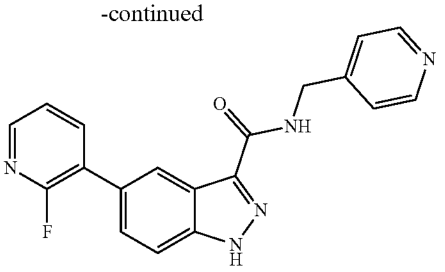

compound 51

To a solution of 20-040 (23.9 mg, 0.0688 mmol) in DCM (0.5 ml) were added 4N HCl in dioxane (0.25 ml), and the reaction mixture was stirred overnight at room temperature. The reaction mixture was concentrated in a vacuum to afford Compound 51 as a white solid (18.6 mg, 0.0535 mmol, 78%).

LC/MS 348.4[M+H]+

1H NMR (400 MHz, DMSO-d6) δ 13.98 (s, 1H), 9.39 (t, J=6.1 Hz, 1H), 8.83 (d, 2H), 8.36 (s, 1H), 8.26 (dt, J=4.8, 1.6 Hz, 1H), 8.16 (ddd, J=10.4, 7.5, 1.9 Hz, 1H), 7.96 (d, 2H), 7.80 (dd, J=8.8, 0.9 Hz, 1H), 7.68 (dt, J=8.8, 1.7 Hz, 1H), 7.49 (ddd, J=7.0, 4.8, 1.9 Hz, 1H), 4.76 (d, J=6.1 Hz, 2H).

Compound 52. 5-(6-Formylbenzo[d][1,3]dioxol-5-yl)-N-(pyridin-4-yl)-1H-indazole-3-carboxamide

[Reaction Scheme 52]

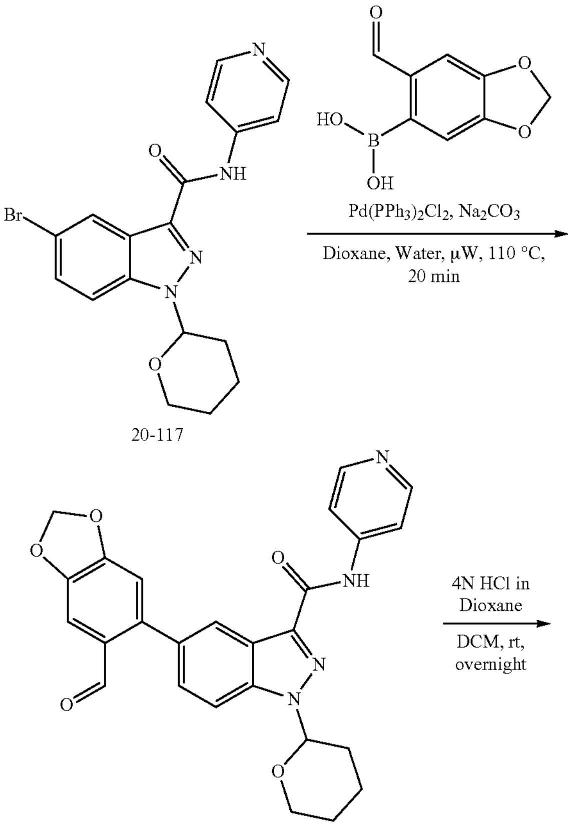

20-035

-continued

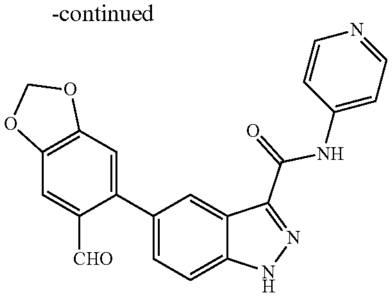

compound 52

1) Synthesis of 5-(6-formylbenzo[d][1,3]dioxol-5-yl)-N-(pyridin-4-yl)-1-(tetrahydro-2H-pyran-2-yl)-1H-indazole-3-carboxamide A solution of $Na_2CO_3$ (33.1 mg, 0.312 mmol) in water was introduced into a suspension of 20-117 (50.0 mg, 0.125 mmol), a palladium catalyst (8.77 mg, 0.0125 mmol) and (6-formylbenzo[d][1,3]dioxol-5-yl)boronic acid (29.1 mg, 0.150 mmol) in dioxane, followed by purging with nitrogen for 5 minutes. The reaction mixture was exposed to microwaves at 110° C. for 20 minutes. The crude reaction mixture was filtered with dioxane and concentrated in a vacuum to give a crude mixture. Purification by column chromatography using DCM/MeOH 10% as an eluent afforded 20-035 as a brown solid (48.1 mg, 0.102 mmol, 82%).

LC/MS 471.5[M+H]+

1H NMR (400 MHz, DMSO-d6) δ 10.69 (s, 1H), 9.67 (s, 1H), 8.53-8.46 (m, 2H), 8.17 (dd, J=1.8, 0.8 Hz, 1H), 8.02 (dd, J=8.8, 0.8 Hz, 1H), 7.94-7.90 (m, 2H), 7.64-7.60 (m, 1H), 7.39 (s, 1H), 7.16 (s, 1H), 6.24 (s, 2H), 6.09 (dd, J=10.1, 2.3 Hz, 1H), 4.05-3.97 (m, 1H), 3.90-3.81 (m, 1H), 2.65-2.57 (m, 1H), 2.15-2.04 (m, 2H), 1.88-1.77 (m, 1H), 1.71-1.60 (m, 2H).

2) Synthesis of 5-(6-formylbenzo[d][1,3]dioxol-5-yl)-N-(pyridin-4-yl)-1H-indazole-3-carboxamide To a solution of 20-035 (36.8 mg, 0.0782 mmol) in DCM (0.5 ml) was added 4N HCl in dioxane (0.25 ml), and the reaction mixture was stirred overnight at room temperature. The reaction mixture was concentrated in a vacuum to afford Compound 52 as a green solid (11.8 mg, 0.0305 mmol, 39%).

LC/MS 401.5[M+H]+

1H NMR (400 MHz, DMSO-d6) δ 14.47 (s, 1H), 11.93 (s, 1H), 8.79 (d, J=6.6 Hz, 2H), 8.46 (d, J=6.7 Hz, 2H), 7.97 (d, J=8.7 Hz, 1H), 7.84 (d, J=8.6 Hz, 1H), 7.57 (s, 1H), 7.29 (s, 1H), 6.42 (s, 1H), 6.12 (s, 2H).

Compound 53. 5-(2-Fluoropyridin-3-yl)-1-(tetrahydro-2H-pyran-2-yl)-N-(2-(2,2,2-trifluoroacetyl)-1,2,3,4-tetrahydroisoquinolin-7-yl)-1H-indazole-3-carboxamide

[Reaction Scheme 53]

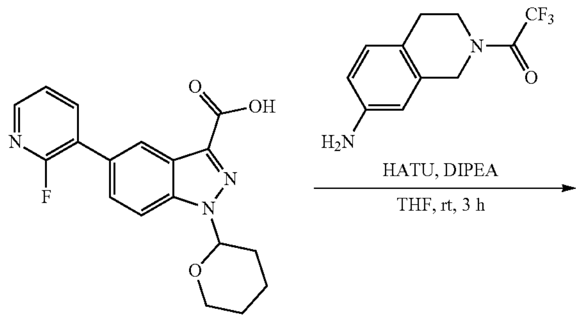

20-028

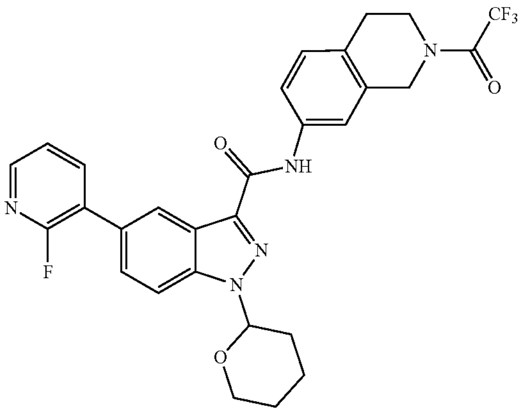

compound 53

To a suspension of 20-028 (40.0 mg, 0.117 mmol) in THF (1 mL) were added DIPEA (45.5 mg, 0.351 mmol) and then HATU (53.2 mg, 0.140 mmol) at room temperature, and the reaction mixture was stirred for 15 minutes. After addition of 1-(7-amino-3,4-dihydroisoquinolin-2(1H)-yl)-2,2,2-trifluoroethan-1-one (31.5 mg, 0.129 mmol), the reaction mixture was stirred overnight at room temperature. The residual solvent was evaporated in a vacuum. The resulting crude mixture was diluted in 15 ml of water before extraction with ethyl acetate (3x15 ml). The organic layers thus obtained were pooled, dried over $MgSO_4$, and concentrated in a vacuum to give a crude mixture. Double purification by column chromatography using MeOH/DCM 8% as an eluent afforded Compound 53 as a brown solid (33.0 mg, 0.0581 mmol, 50%).

Impurities observed (δ 7.68-7.90)

1H NMR (400 MHz, DMSO-d6) δ 13.94 (s, 1H), 10.78 (s, 1H), 8.48 (d, J=5.5 Hz, 2H), 8.36 (s, 1H), 8.26 (d, J=1.3 Hz, 1H), 7.97-7.92 (m, 2H), 7.79 (t, J=1.7 Hz, 1H), 7.75 (d, J=1.6 Hz, 1H), 7.72 (s, 1H), 7.02 (d, J=1.7 Hz, 1H).

Compound 54. 5-(2-Fluoropyridin-3-yl)-1-(tetrahydro-2H-pyran-2-yl)-N-(1,2,3,4-tetrahydroisoquinolin-7-yl)-1H-indazole-3-carboxamide

[Reaction Scheme 54]

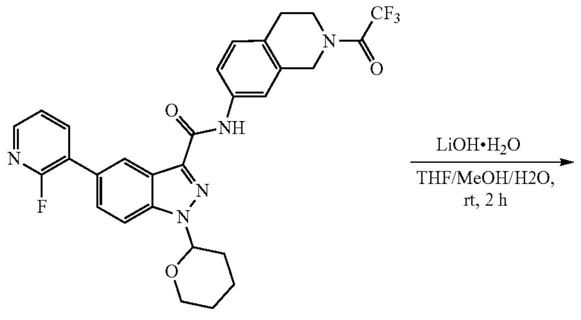

20-041

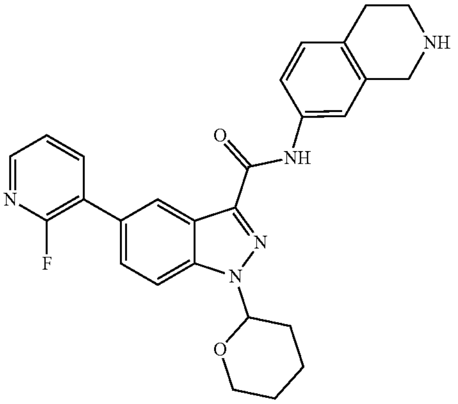

compound 54

To a solution of 20-041 (26.8 mg, 0.0529 mmol) in THF (4 mL), MeOH (2 mL), and $H_2O$ (1 mL) was added lithium hydroxide monohydrate (3.96 mg, 0.106 mmol) at room temperature, and the reaction mixture was stirred at room temperature for 2 hours. The crude reaction mixture was concentrated in a vacuum to give a crude mixture. Purification by column chromatography using DCM/MeOH 10% as an eluent afforded Compound 54 as a white solid (17.5 mg, 0.0371 mmol, 70%).

LC/MS 472.5[M+H]+

1H NMR (400 MHz, DMSO-d6) δ 10.26 (s, 1H), 8.44 (d, J=1.9 Hz, 1H), 8.28 (dt, J=4.8, 1.5 Hz, 1H), 8.20 (ddd, J=10.4, 7.4, 1.9 Hz, 1H), 8.04-8.00 (m, 1H), 7.77 (dt, J=8.7, 1.7 Hz, 2H), 7.65 (dd, J=8.3, 2.3 Hz, 1H), 7.52 (ddd, J=7.0, 4.8, 1.8 Hz, 1H), 7.16 (d, J=8.4 Hz, 1H), 6.05 (dd, J=9.9, 2.4 Hz, 1H), 4.13 (s, 2H), 4.01-3.95_(m, 1H), 3.87-3.80 (m, 1H), 3.23 (t, J=6.1 Hz, 2H), 2.85 (t, J=6.1 Hz, 2H), 2.68-2.56 (m, 1H), 2.13-2.03 (m, 2H), 1.86-1.76 (m, 1H), 1.69-1.60 (m, 2H).

Compound 55. 5-(2-Fluoropyridin-3-yl)-N-(1,2,3,4-tetrahydroisoquinolin-7-yl)-1H-indazole-3-carboxamide hydrochloride

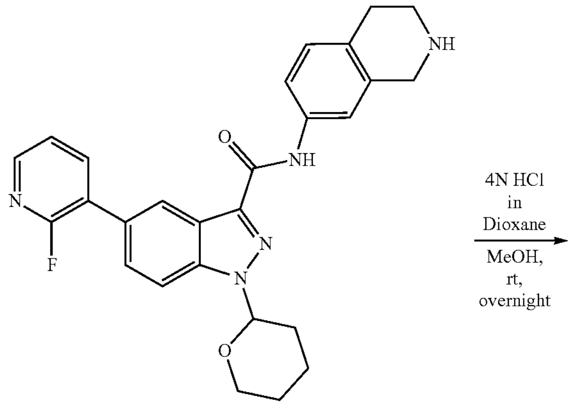

20-049

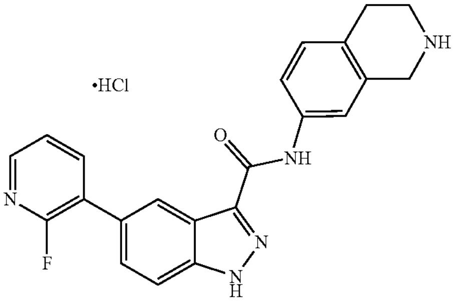

Compound 55

To a solution of 20-049 (7.50 mg, 0.0159 mmol) in MeOH (0.5 ml) was added 4N HCl in dioxane (0.3 ml), and the reaction mixture was stirred overnight at room temperature. The reaction mixture was concentrated in a vacuum to afford Compound 55 as a white solid (4.80 mg, 0.0113 mmol, 71%).

LC/MS 388.4[M+H]+

1H NMR (400 MHz, DMSO-d6) δ 14.06-13.88 (m, 1H), 10.49-10.40 (m, 1H), 9.16 (s, 2H), 8.49-8.33 (m, 1H), 8.28 (dt, J=4.8, 1.5 Hz, 1H), 8.23-8.16 (m, 1H), 7.92-7.86 (m, 1H), 7.85-7.77 (m, 1H), 7.75-7.62 (m, 2H), 7.52 (ddd, J=7.0, 4.8, 1.8 Hz, 1H), 7.22 (d, J=8.3 Hz, 1H), 4.33-4.21 (m, 2H), 3.95-3.85 (m, 2H), 3.02-2.93 (m, 2H).

Compound 56. 5-(6-(Piperidin-1-ylmethyl)benzo[d][1,3]dioxol-5-yl)-N-(pyridin-4-yl)-1H-indazole-3-carboxamide

[Reaction Scheme 56]

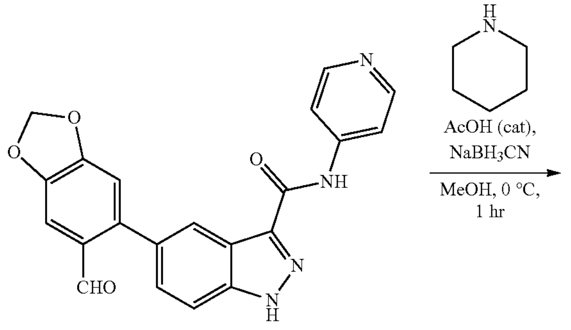

20-043

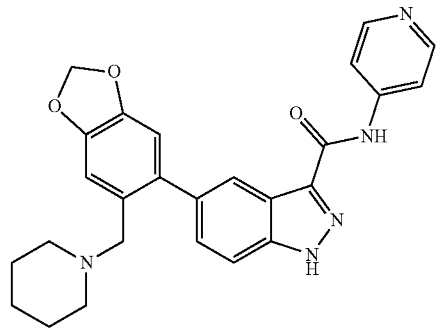

compound 56

To a solution of 20-043 (10.6 mg, 0.0274 mmol) in MeOH (1 mL) was added piperidine (2.57 mg, 0.0302 mmol) at 0° C. In the presence of the catalyst AcOH (0.1 ml), the reaction was conducted at room temperature for 1 hour while stirring. Sodium cyanoborohydride (8.9 mg, 0.14 mmol) was added, followed by stirring at room temperature until completion of the reaction. After completion of the reaction, the reaction mixture was quenched with 2 ml of water and MeOH was evaporated. Extraction from the aqueous layer was conducted with ethyl acetate (2×15 ml). The crude reaction mixture was concentrated in a vacuum to give a crude mixture. Purification by column chromatography using DCM/MeOH 5% as an eluent afforded Compound 56 as a yellow solid (10.1 mg, 0.0222 mmol, 81%).

LC/MS 456.6[M+H]+

1H NMR (400 MHz, DMSO-d6) δ 14.00 (d, J=29.6 Hz, 1H), 10.95 (s, 1H), 8.52 (d, 2H), 7.95 (dd, 2H), 7.87 (d, J=8.6 Hz, 1H), 7.73-7.68 (m, 1H), 7.49 (d, J=5.0 Hz, 1H), 7.28 (d, J=4.0 Hz, 1H), 6.07 (d, J=8.8 Hz, 2H), 5.84 (s, 1H), 3.04-2.97 (m, 4H), 1.69-1.67 (m, 4H), 1.60-1.52 (m, 2H).

Compound 57. tert-butyl 4-((5-(3-(pyridin-4-ylcarbamoyl)-1-(tetrahydro-2H-pyran-2-yl)-1H-indazol-5-yl))methyl)piperazine-1-carboxylate

[Reaction Scheme 57]

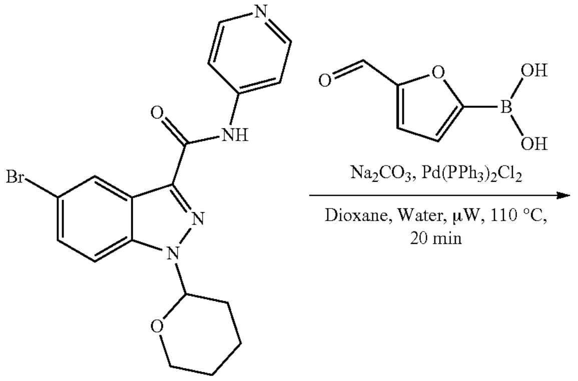

20-117

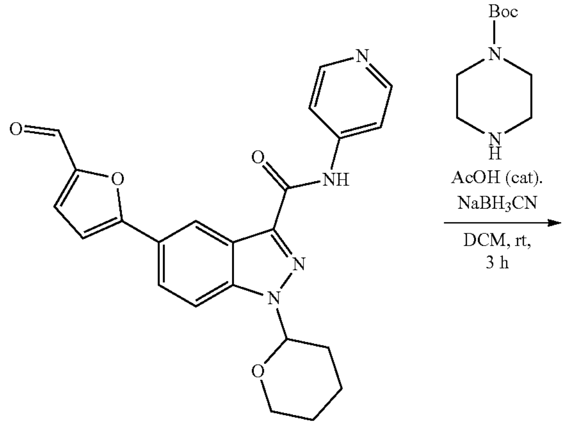

20-092

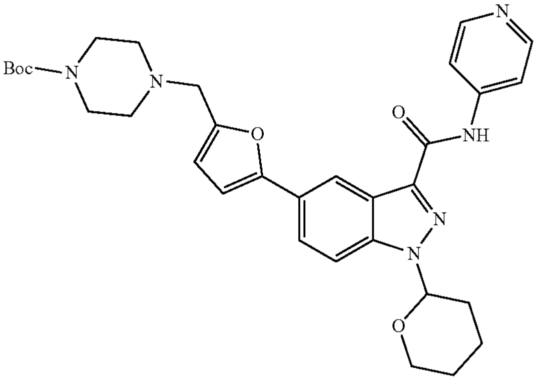

compound 57

1) Synthesis of 5-(5-formylfuran-2-yl)-N-(pyridin-4-yl)-1-(tetrahydro-2H-pyran-2-yl)-1H-indazole-3-carboxamide A solution of $Na_2CO_3$ (198 mg, 1.87 mmol) in water was introduced into a suspension of 20-117 (300 mg, 0.748 mmol), a palladium catalyst (52.5 mg, 0.0748 mmol) and (5-formylfuran-2-yl)boronic acid (125 mg, 0.897 mmol) in dioxane, followed by purging with nitrogen for 5 minutes. The reaction mixture was exposed to microwaves at 110° C. for 20 minutes. The crude reaction mixture was filtered with dioxane and concentrated in a vacuum to give a crude mixture. Purification by column chromatography using DCM/MeOH 7% as an eluent afforded 20-092 as an orange color solid (136 mg, 0.326 mmol, 44%).

1H NMR (300 MHz, DMSO-d6) δ 10.72 (s, 1H), 9.65 (s, 1H), 8.71 (t, J=1.2 Hz, 1H), 8.52 (d, J=5.5 Hz, 2H), 8.11-8.02 (m, 2H), 7.99-7.93 (m, 2H), 7.70 (d, J=3.8 Hz, 1H), 7.40 (d, J=3.8 Hz, 1H), 6.07 (dd, J=10.1, 2.3 Hz, 1H), 4.06-3.95 (m, 1H), 3.91-3.79 (m, 1H), 2.67-2.55 (m, 1H), 2.16-1.98 (m, 2H), 1.90-1.76 (m, 1H), 1.70-1.58 (m, 2H).

2) Synthesis of tert-butyl 4-((5-(3-(pyridin-4-ylcarbamoyl)-1-(tetrahydro-2H-pyran-2-yl)-1H-indazol-5-yl)furan-2-yl)methyl)piperazine-1-carboxylate To a solution of 20-092 (30.0 mg, 0.0720 mmol) in DMF (1 mL) was added tert-butyl piperazine-1-carboxylate (14.8 mg, 0.0792 mmol). In the presence of the catalyst AcOH (0.1 ml), the reaction was conducted at room temperature for 1 hour while stirring. Sodium cyanoborohydride (6.79 mg, 0.108 mmol) was added, followed by stirring at room temperature until completion of the reaction. After completion of the reaction, the reaction mixture was quenched with 2 ml of water. Then, extraction was conducted with ethyl acetate (2×15 ml). The organic layer was washed with water and brine and dried over sodium sulfate. The solvent was evaporated in a vacuum. Purification by column chromatography using DCM/MeOH 7% as an eluent afforded Compound 57 as a white solid (19.3 mg, 0.0329 mmol, 46%).

LC/MS 587.5[M+H]+

1H NMR (300 MHz, Chloroform-d) δ 9.51 (s, 1H), 8.59 (dd, J=1.6, 0.8 Hz, 1H), 8.49-8.40 (m, 2H), 8.06-7.98 (m, 2H), 7.84 (dd, J=8.9, 1.6 Hz, 1H), 7.72-7.66 (m, 1H), 6.72 (d, J=3.3 Hz, 1H), 6.35 (d, J=3.3 Hz, 1H), 5.82 (dd, J=9.7, 2.5 Hz, 1H), 4.19-4.08 (m, 1H), 3.89-3.80 (m, 1H), 3.48 (q, J=8.4, 6.7 Hz, 4H), 2.53 (t, J=5.1 Hz, 4H), 2.21-2.11 (m, 3H), 1.88-1.74 (m, 3H), 1.46 (s, 9H).

Compound 58. N-(1,1-Dimethyl-2-(2,2,2-trifluoroacetyl)-1,2,3,4-tetrahydroisoquinolin-7-yl)-5-(2-fluoropyridin-3-yl)-1H-indazole-3-carboxamide

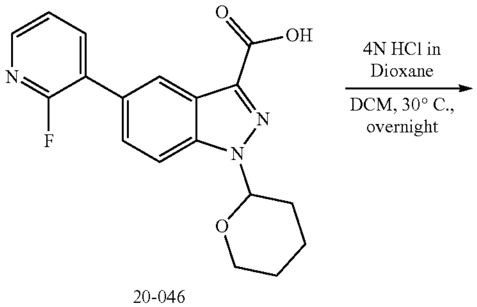

20-046

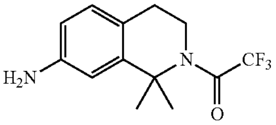

18-036

HATU, DIPEA

DMF, rt, overnight

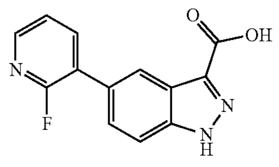

20-228

-continued

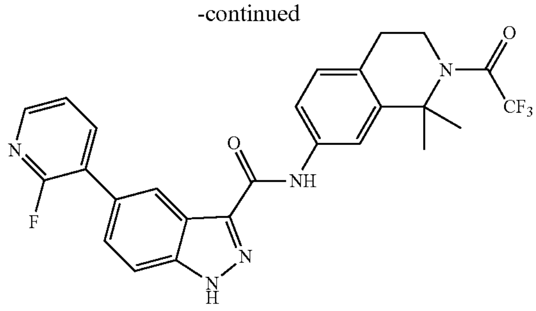

Compound 58

1) Synthesis of 5-(2-fluoropyridin-3-yl)-1H-indazole-3-carboxylic acid

To a solution of 20-046 (100 mg, 0.293 mmol) in DCM (2.0 mL) was added 4N HCl in dioxane (0.70 ml, excess). At 30° C., the reaction was conducted for 4 hours while stirring. When the starting material was not observed as monitored by TLC, the solvent was evaporated in a vacuum. The reaction mixture was washed with MC, followed by filtration to afford Compound 20-228 as a gray solid (64 mg, 0.249 mmol, 85%).

*TLC indicated the formation of a blue fluorescent spot.

1H NMR (400 MHz, DMSO-d6) δ 14.02 (s, 1H), 13.05 (s, 1H), 8.33-8.24 (m, 2H), 8.18 (ddd, J=9.6, 7.4, 1.9 Hz, 1H), 7.79 (d, J=8.7 Hz, 1H), 7.67 (dt, J=8.7, 1.8 Hz, 1H), 7.50 (ddd, J=7.1, 4.8, 1.9 Hz, 1H).

2) Synthesis of N-(1,1-dimethyl-2-(2,2,2-trifluoroacetyl)-1,2,3,4-tetrahydro isoquinolin-7-yl)-5-(2-fluoropyridin-3-yl)-1H-indazole-3-carboxamide To a suspension of 18-036 (23.3 mg, 0.0855 mmol) in DMF (1 mL) were added DIPEA (30.2 mg, 0.0934 mmol) and then HATU (35.5 mg, 0.0934 mmol). After addition of 20-228 (20.0 mg, 0.0778 mmol), the reaction mixture was stirred overnight at room temperature. When the starting material was completely consumed as monitored by TLC, the reaction mixture was concentrated by evaporation and added with EtOAc (20 mL). The organic layer was washed with water, dried over sodium sulfate, and concentrated in a vacuum. The organic layer was washed with water, dried over sodium sulfate, and concentrated in a vacuum. Recrystallization of the reaction mixture in EA/Hex afforded Compound 58 as a gray solid (15 mg 0.0293 mmol, 38%).

LCMS: [M+H] 512.2

1H NMR (400 MHz, DMSO-d6) δ 13.97 (s, 1H), 10.38 (s, 1H), 8.46 (d, J=1.6 Hz, 1H), 8.28 (dt, J=4.7, 1.6 Hz, 1H), 8.21 (ddd, J=10.4, 7.5, 1.9 Hz, 1H), 7.98 (d, J=2.1 Hz, 1H), 7.84-7.77 (m, 2H), 7.71 (dt, J=8.8, 1.8 Hz, 1H), 7.52 (ddd, J=7.1, 4.8, 1.9 Hz, 1H), 7.16 (d, J=8.4 Hz, 1H), 3.64 (m, 2H), 2.89-2.84 (m, 2H), 1.80 (s, 6H).

Compound 59. N-(1,1-dimethyl-1,2,3,4-tetrahydroisoquinolin-7-yl)-5-(2-fluoropyridin-3-yl)-1H-indazole-3-carboxamide

[Reaction Scheme 59]

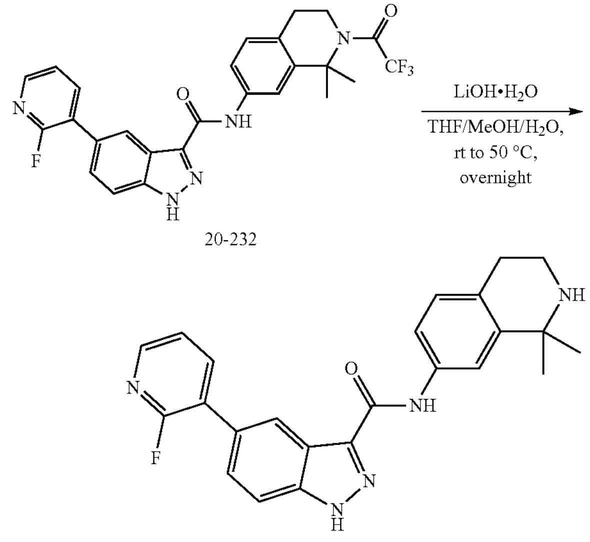

20-232 compound 59

To a solution of 20-232 (10.0 mg, 0.0196 mmol) in THE (1 ml), MeOH (0.5 ml), and $H_2O$ (0.25 ml) was added lithium hydroxide monohydrate (1.64 mg, 0.0391 mmol) at room temperature, and the reaction mixture was stirred overnight with the temperature elevated from room temperature to 50° C. When the starting material was completely consumed as monitored by TLC, the reaction mixture was concentrated by evaporation in a vacuum. After addition of $H_2O$, the solid thus formed was filtered to afford Compound 59 as a gray solid (1.8 mg, 0.00433 mmol, 22%).

LCMS: [M+H] 416.2

1H NMR (400 MHz, DMSO-d6) δ 13.90 (s, 1H), 10.20 (s, 1H), 8.45 (s, 1H), 8.27 (d, J=4.6 Hz, 1H), 8.21 (ddd, J=9.9, 7.4, 2.0 Hz, 1H), 7.83-7.78 (m, 2H), 7.70 (dt, J=8.8, 1.8 Hz, 1H), 7.65 (dd, J=8.3, 2.2 Hz, 1H), 7.51 (ddd, J=7.0, 4.8, 1.8 Hz, 1H), 7.00 (d, J=8.3 Hz, 1H), 2.96 (t, J=5.8 Hz, 2H), 2.65 (t, J=5.7 Hz, 2H), 1.37 (s, 6H).

Compound 60. 5-(2-Fluoropyridin-3-yl)-N-(1-methyl-1H-pyrazolo[3,4-b]pyridin-4-yl)-1-(tetrahydro-2H-pyran-2-yl)-1H-indazole-3-carboxamide

[Reaction Scheme 60]

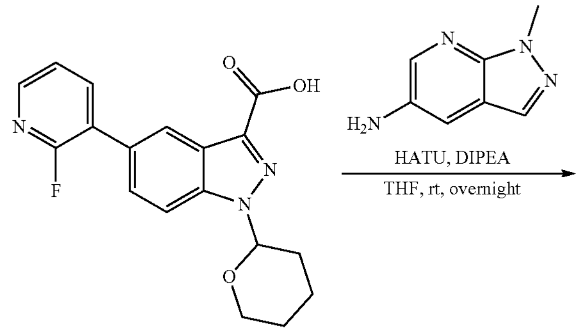

20-081

-continued

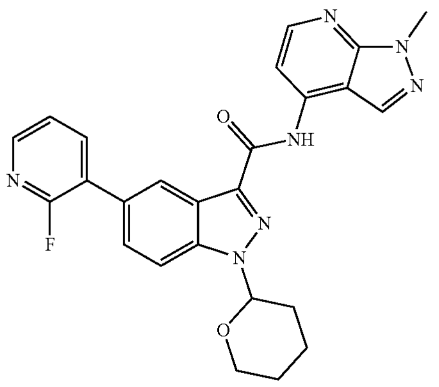

Compound 60

To a suspension of 1-methyl-1H-pyrazolo[3,4-b]pyridin-5-amine (9.50 mg, 0.0645 mmol) in DMF (1 mL) were added DIPEA (22.8 mg, 0.176 mmol) and then HATU (26.7 mg, 0.0703 mmol). After addition of 20-081 (20.0 mg, 0.0778 mmol), the reaction mixture was stirred overnight at room temperature. When the starting material was completely consumed as monitored by TLC, the reaction mixture was concentrated by evaporation. EtOAc (20 mL) was added, and the organic layer was washed with water, dried over sodium sulfate, and concentrated in a vacuum. Recrystallization of the reaction mixture in EA/Hex afforded Compound 60 as a brown solid (46.1 mg, 0.0978 mmol, 67%).

LCMS: [M+H] 472.2

1H NMR (300 MHz, DMSO-d6) δ 10.66 (s, 1H), 8.93 (d, J=2.3 Hz, 1H), 8.73 (d, J=2.3 Hz, 1H), 8.47 (s, 1H), 8.28 (dt, J=4.8, 1.5 Hz, 1H), 8.21 (ddd, J=10.3, 7.5, 1.9 Hz, 1H), 8.16 (s, 1H), 8.04 (dd, J=8.9, 0.8 Hz, 1H), 7.78 (dt, J=8.8, 1.7 Hz, 1H), 7.54-7.47 (m, 1H), 6.08 (dd, J=10.0, 2.3 Hz, 1H), 4.08 (s, 3H), 4.03-3.96 (m, 1H), 3.90-3.78 (m, 1H), 2.64 (d, J=11.6 Hz, 1H), 2.23-1.77 (m, 3H), 1.71-1.56 (m, 2H).

Compound 61. tert-butyl 4-(4-(3-(pyridin-4-ylcarbamoyl)-1-(tetrahydro-2H-pyran-2-yl)-1H-indazol-5-yl)benzoyl)piperazine-1-carboxylate

[Reaction Scheme 61]

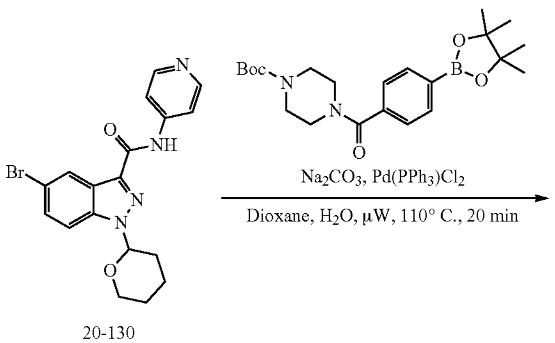

20-130

-continued

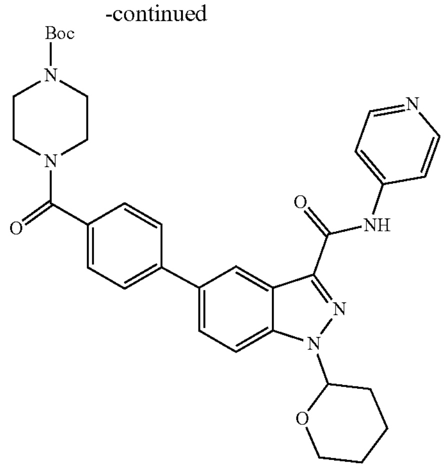

compound 61

A solution of $Na_2CO_3$ (33.2 mg, 0.313 mmol) in water was introduced into a suspension of 20-130 (50 mg, 0.125 mmol), a palladium catalyst (8.80 mg, 0.0125 mmol) and tert-butyl 4-(4-(4,4,5,5-tetramethyl-1,3,2-dioxaborolan-2-yl)benzoyl)piperazine-1-carboxylate (62.3 mg, 0.150 mmol) in dioxane, followed by purging with nitrogen for 15 minutes. The reaction mixture was exposed to microwaves at 110° C. for 20 minutes. The resulting crude mixture was diluted in 10 ml of water before extraction with 30 mL of ethyl acetate. The organic layers thus obtained were pooled, dried over $Na_2SO_4$, and concentrated in a vacuum to give a crude mixture. Purification by column chromatography using MeOH/MC 10% as an eluent afforded Compound 61 as a gray solid (47.3 mg, 0.0774 mmol, 62%).

LCMS: [M+H] 611.3.

1H NMR (400 MHz, DMSO-d6) δ 10.68 (s, 1H), 8.55-8.44 (m, 3H), 8.03 (dd, J=9.0, 0.8 Hz, 1H), 7.96-7.93 (m, 2H), 7.91 (dd, J=8.9, 1.8 Hz, 1H), 7.84-7.80 (m, 2H), 7.58-7.53 (m, 2H), 6.07 (dd, J=10.0, 2.4 Hz, 1H), 4.06-3.96 (m, 1H), 3.92-3.81 (m, 1H), 3.66-3.37 (m, 8H), 2.68-2.57 (m, 1H), 2.08 (d, J=12.5 Hz, 2H), 1.83 (s, 1H), 1.72-1.60 (m, 2H), 1.42 (s, 9H).

Compound 62. tert-butyl 4-(4-(3-(pyridin-4-ylcarbamoyl)-1-(tetrahydro-2H-pyran-2-yl)-1H-indazol-5-yl)benzyl)piperazine-1-carboxylate

[Reaction Scheme 62]

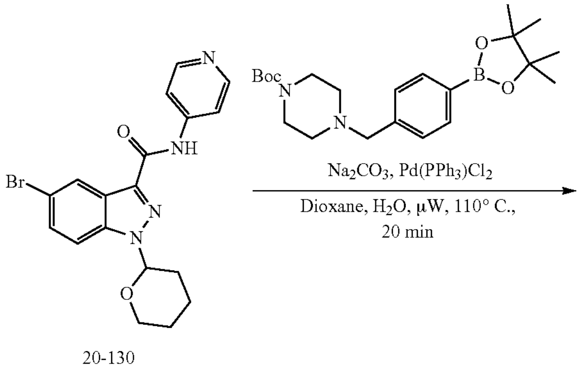

20-130

-continued

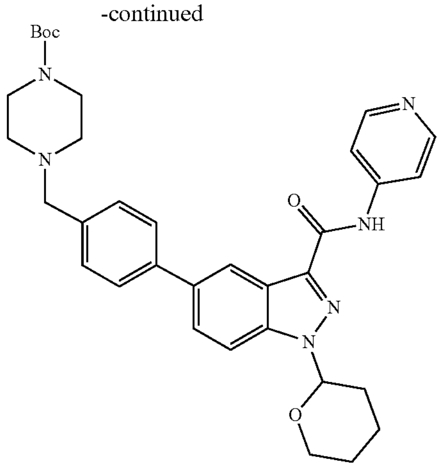

compound 62

A solution of $Na_2CO_3$ (33.2 mg, 0.313 mmol) in water was introduced into a suspension of 20-130 (50 mg, 0.125 mmol), a palladium catalyst (8.80 mg, 0.0125 mmol) and tert-butyl 4-(4-(4,4,5,5-tetramethyl-1,3,2-dioxaborolan-2-yl)benzoyl)piperazine-1-carboxylate (60.4 mg, 0.150 mmol) in dioxane, followed by purging with nitrogen for 15 minutes. The reaction mixture was exposed to microwaves at 110° C. for 20 minutes. The crude reaction mixture was filtered with dioxane and concentrated in a vacuum to give a crude mixture. Purification by column chromatography using MeOH/MC 10% as an eluent afforded Compound 62 as a gray solid (35.6 mg, 0.0596 mmol, 51%).

LCMS: [M+H] 597.3

1H NMR (400 MHz, DMSO-d6) δ 10.65 (s, 1H), 8.55-8.48 (m, 2H), 8.44 (dd, J=1.8, 0.8 Hz, 1H), 8.03-7.96 (m, 1H), 7.95-7.92 (m, 2H), 7.86 (dd, J=8.9, 1.7 Hz, 1H), 7.73-7.63 (m, 2H), 7.45 (d, J=8.0 Hz, 2H), 6.06 (dd, J=10.1, 2.3 Hz, 1H), 4.05-3.96 (m, 1H), 3.89-3.80 (m, 1H), 3.55 (s, 2H), 3.36-3.34 (m, 4H), 2.74-2.57 (m, 1H), 2.41-2.32 (m, 4H), 2.15-2.02 (m, 2H), 1.91-1.73 (m, 1H), 1.71-1.59 (m, 2H), 1.39 (s, 9H).

Compound 63. 5-(2-Fluoropyridin-3-yl)-N-(1-methyl-1,2,3,4-tetrahydroisoquinolin-7-yl)-1H-indazole-3-carboxamide

[Reaction Scheme 63]

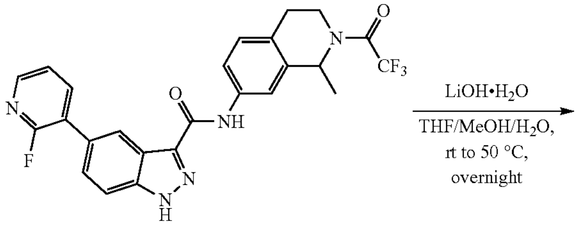

20-244

-continued

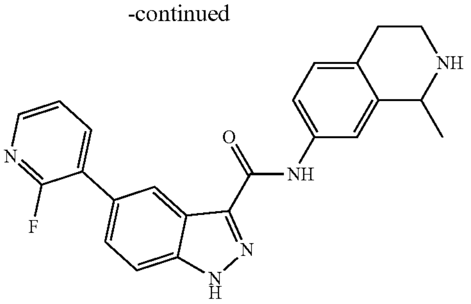

compound 63

To a solution of 20-244 (10.0 mg, 0.0201 mmol) in THE (1 ml), MeOH (0.5 ml), and $H_2O$ (0.25 ml) was added lithium hydroxide monohydrate (3.40 mg, 0.0804 mmol) at room temperature, and the reaction mixture was stirred overnight, with the temperature elevated from room temperature to 50° C. When the starting material was completely consumed as monitored by TLC, the reaction mixture was concentrated by evaporation in a vacuum. After addition of $H_2O$, the solid thus formed was filtered to afford Compound 63 as a yellow solid (2.4 mg, 0.00598 mmol, 30%).

LCMS: [M+H] 402.2

1H NMR (400 MHz, DMSO-d6) δ 10.22 (s, 1H), 8.45 (s, 1H), 8.27 (dt, J=4.9, 1.5 Hz, 1H), 8.20 (ddd, J=9.8, 7.4, 1.9 Hz, 1H), 7.80 (d, J=8.7 Hz, 1H), 7.75 (d, J=2.2 Hz, 1H), 7.69 (dt, J=8.7, 1.8 Hz, 1H), 7.63 (dd, J=8.2, 2.2 Hz, 1H), 7.51 (ddd, J=7.1, 4.8, 1.9 Hz, 1H), 7.02 (d, J=8.3 Hz, 1H), 3.99-3.87 (m, 1H), 3.13-3.04 (m, 1H), 2.87-2.77 (m, 1H), 2.75-2.67 (m, 1H), 2.65-2.56 (m, 1H), 1.36 (d, J=6.6 Hz, 3H), 1.26 (dd, J=14.3, 7.7 Hz, 1H).

Compound 64. 5-(2-Fluoropyridin-3-yl)-N-(1,2,3,4-tetrahydroisoquinolin-6-yl)-1H-indazole-3-carboxamide

[Reaction Scheme 64]

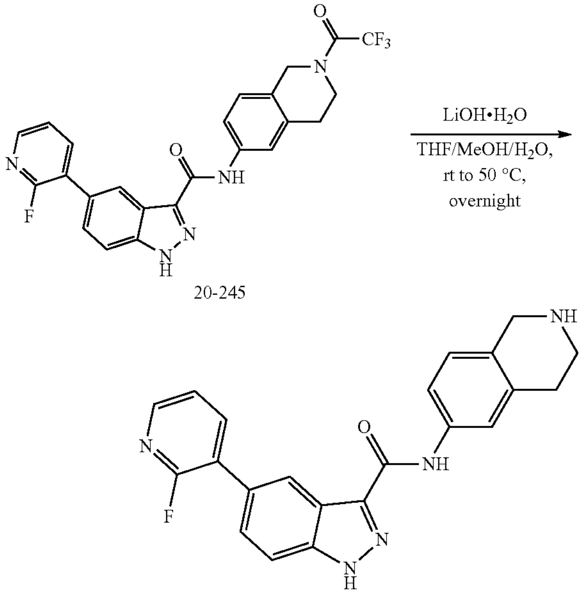

20-245 compound 64

To a solution of 20-245 (10.0 mg, 0.0207 mmol) in THE (1 ml), MeOH (0.5 ml), and $H_2O$ (0.25 ml) was added lithium hydroxide monohydrate (3.50 mg, 0.0827 mmol) at room temperature, and the reaction mixture was stirred overnight, with the temperature elevated from room temperature to 50° C. When the starting material was completely consumed as monitored by TLC, the reaction mixture was concentrated by evaporation in a vacuum. After addition of $H_2O$, the solid thus formed was filtered to afford Compound 64 as a yellow solid (4.9 mg, 0.0126 mmol, 61%).

LCMS: [M+H] 388.2

1H NMR (400 MHz, DMSO-d6) δ 10.22 (s, 1H), 8.45 (s, 1H), 8.27 (dt, J=4.8, 1.5 Hz, 1H), 8.20 (ddd, J=10.5, 7.4, 1.9 Hz, 1H), 7.80 (dd, J=8.7, 0.9 Hz, 1H), 7.75-7.65 (m, 2H), 7.57 (dd, J=8.3, 2.2 Hz, 1H), 7.51 (ddd, J=7.1, 4.8, 1.9 Hz, 1H), 6.98 (d, J=8.3 Hz, 1H), 3.81 (s, 2H), 2.95 (t, J=5.9 Hz, 2H), 2.69 (t, J=7.6, 4.6 Hz, 2H), 1.24 (s, 1H).

Compound 65. 5-(2-Fluoropyridin-3-yl)-N-(1-methyl-1H-pyrazolo[3,4-b]pyridin-4-yl)-1H-indazole-3-carboxamide

[Reaction Scheme 65]

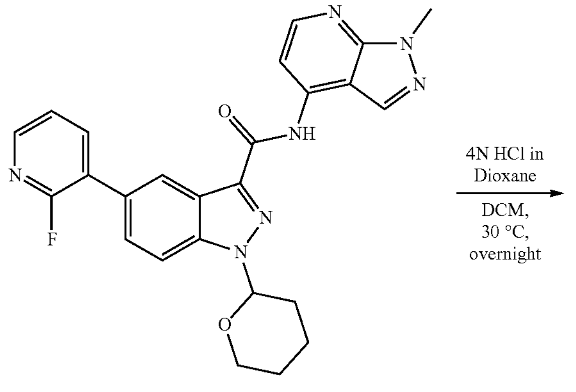

20-239

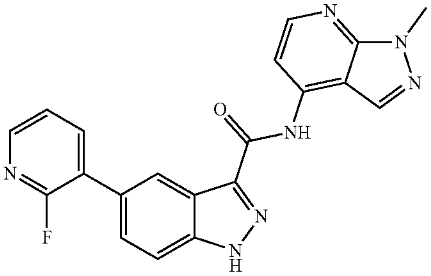

compound 65

To a solution of 20-239 (10.0 mg, 0.0212 mmol) in DCM (1.0 mL) was added 4N HCl (0.50 ml, excess) in dioxane. At 30° C., the reaction was conducted overnight while stirring. When no starting materials were observed as monitored by TCL, the solvent was evaporated in a vacuum. The residue was added MC and filtered to afford Compound 65 as a yellow solid (1.7 mg 0.00439 mmol, 21%).

LCMS: [M+H] 388.2

1H NMR (400 MHz, DMSO-d6) δ 14.05 (s, 1H), 10.78 (s, 1H), 9.00-8.90 (m, 1H), 8.76-8.70 (m, 1H), 8.47 (s, 1H), 8.30-8.26 (m, 1H), 8.21 (ddd, J=9.8, 7.3, 2.0 Hz, 1H), 8.15 (d, J=4.1 Hz, 1H), 7.83 (d, J=8.7 Hz, 1H), 7.72 (dt, J=8.7, 1.8 Hz, 1H), 7.52 (ddt, J=7.0, 4.8, 2.1 Hz, 1H), 4.08 (s, 3H).

Compound 66. 5-(2-Fluoropyridin-3-yl)-N-(pyridin-4-yl)-1-(tetrahydro-2H-pyran-2-yl)-1H-indazole-3-carboxamide

[Reaction Scheme 66]

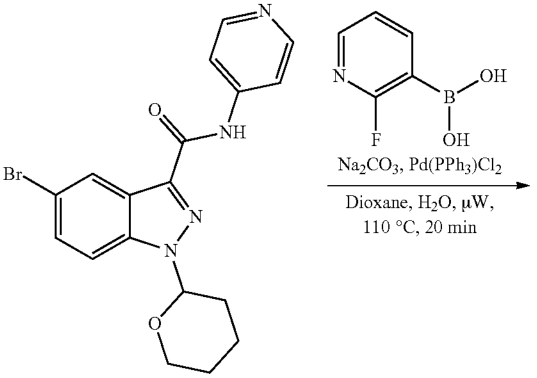

20-130

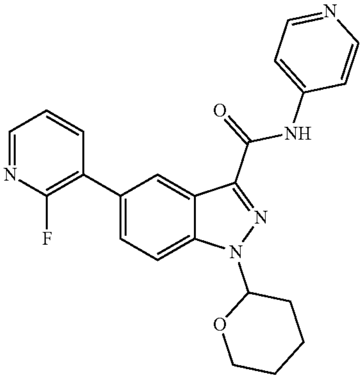

compound 66

A solution of $Na_2CO_3$ (198 mg, 1.87 mmol) in water was introduced into a suspension of 20-130 (300 mg, 0.748 mmol), a palladium catalyst (52.5 mg, 0.0748 mmol) and (2-fluoropyridin-3-yl)boronic acid (127 mg, 0.897 mmol) in dioxane, followed by purging with nitrogen for 15 minutes. The reaction mixture was exposed to microwaves at 110° C. for 20 minutes. The crude reaction mixture was filtered with dioxane and concentrated in a vacuum to give a crude mixture. Purification by column chromatography using MeOH/MC 10% as an eluent afforded Compound 66 as a brown solid (260 mg, 0.623 mmol, 83%).

*Sigma boronic acid was used.

1H NMR (400 MHz, Methanol-d4) δ 8.52 (s, 1H), 8.46 (d, 2H), 8.23 (ddd, J=5.0, 1.9, 1.1 Hz, 1H), 8.15 (ddd, J=9.6, 7.5, 1.9 Hz, 1H), 7.97-7.87 (m, 3H), 7.74 (dt, J=8.9, 1.9 Hz, 1H), 7.46 (ddd, J=7.5, 4.9, 1.7 Hz, 1H), 6.01 (dd, J=9.8, 2.5 Hz, 1H), 4.16-4.05 (m, 1H), 3.90 (ddd, J=11.5, 10.5, 3.1 Hz, 1H), 2.75-2.57 (m, 1H), 2.29-2.08 (m, 2H), 2.02-1.66 (m, 3H).

Compound 67. 5-(4-(Piperazine-1-carbonyl)phenyl)-N-(pyridin-4-yl)-1H-indazole-3-carboxamide

[Reaction Scheme 67]

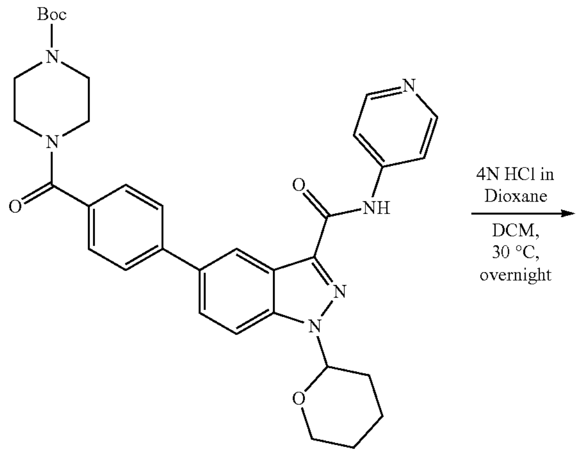

20-246

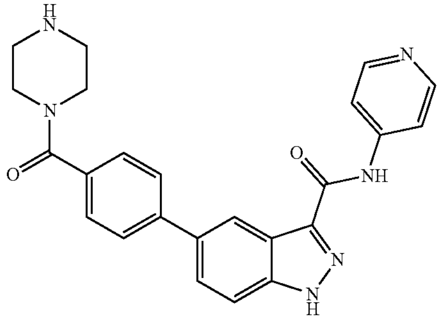

compound 67

To a solution of 20-246 (20.0 mg, 0.0327 mmol) in DCM (1.0 mL) were added 4N HCl (0.50 ml, excess) in dioxane. At 30° C., the reaction was conducted overnight while stirring. When no starting materials were observed as monitored by TCL, the solvent was evaporated in a vacuum. The residue was added MC and filtered to afford Compound 67 as a yellow solid (9.0 mg, 0.0211 mmol, 65%).

LCMS: [M+H] 427.2

1H NMR (300 MHz, DMSO-d6) δ 14.46 (s, 1H), 11.85 (s, 1H), 9.42 (s, 2H), 8.85-8.69 (m, 2H), 8.55-8.40 (m, 3H), 7.93-7.78 (m, 3H), 7.62 (d, 2H), 3.89-3.62 (m, 4H), 3.25-3.10 (m, 4H).

Compound 68. 5-(4-(Piperazin-1-ylmethyl)phenyl)-N-(pyridin-4-yl)-1H-indazole-3-carboxamide

[Reaction Scheme 68]

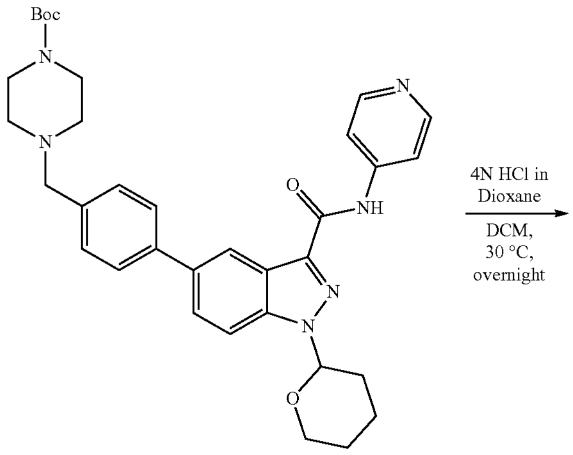

20-247

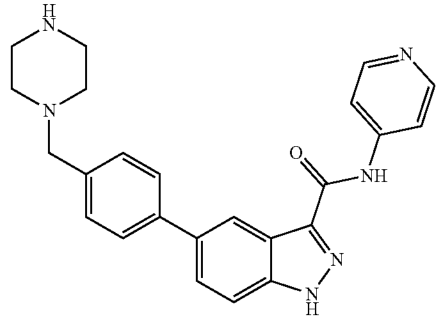

compound 68

To a solution of 20-247 (20.0 mg, 0.0335 mmol) in DCM (1.0 mL) were added 4N HCl (0.50 ml, excess) in dioxane. At 30° C., the reaction was conducted overnight while stirring. When no starting materials were observed as monitored by TCL, the solvent was evaporated in a vacuum. The residue was added MC and filtered to afford Compound 68 as a gray solid (10.7 mg, 0.0259 mmol, 77%).

LCMS: [M+H] 413.2.

1H NMR (300 MHz, DMSO-d6) δ 14.44 (s, 1H), 11.85 (s, 1H), 9.54 (s, 2H), 8.87-8.67 (m, 2H), 8.56-8.41 (m, 3H), 7.91-7.79 (m, 3H), 7.78-7.67 (m, 2H), 4.45-4.22 (m, 2H), 3.63-3.53 (m, 2H), 3.34-3.22 (m, 4H), 3.17 (s, 2H).

Compound 69. 5-(5-(Piperazin-1-ylmethyl)furan-2-yl)-N-(pyridin-4-yl)-1H-indazole-3-carboxamide

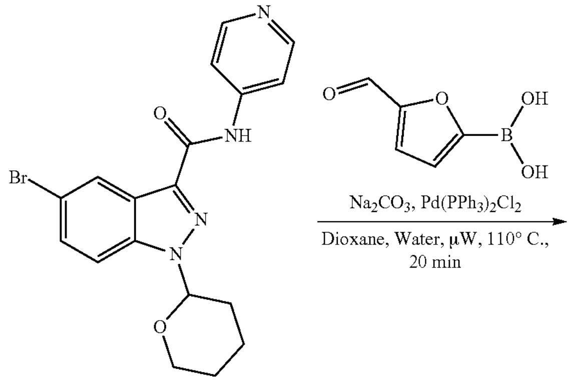

20-117

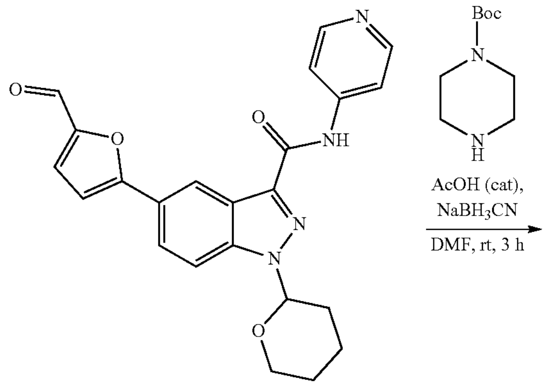

20-092

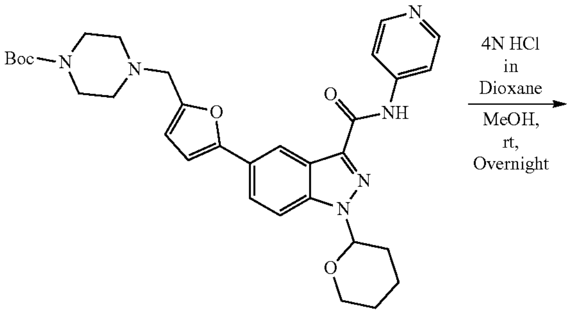

20-097

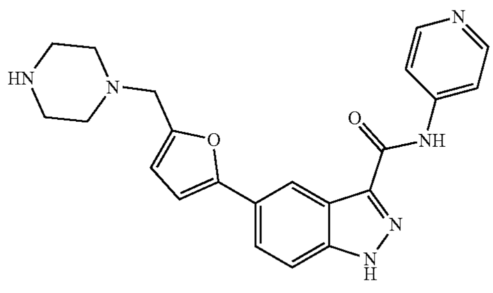

Compound 69

1) Synthesis of 5-(5-formylfuran-2-yl)-N-(pyridin-4-yl)-1-(tetrahydro-2H-pyran-2-yl)-1H-indazole-3-carboxamide A solution of $Na_2CO_3$ (198 mg, 1.87 mmol) in water was introduced into a suspension of 20-117 (300 mg, 0.748 mmol), a palladium catalyst (52.5 mg, 0.0748 mmol) and (5-formylfuran-2-yl)boronic acid (125 mg, 0.897 mmol) in dioxane, followed by purging with nitrogen for 5 minutes. The reaction mixture was exposed to microwaves at 110° C. for 20 minutes. The crude reaction mixture was filtered with dioxane and concentrated in a vacuum to give a crude mixture. Purification by column chromatography using DCM/MeOH 7% as an eluent afforded 20-092 as an orange color solid (136 mg, 0.326 mmol, 44%).

1H NMR (300 MHz, DMSO-d6) δ 10.72 (s, 1H), 9.65 (s, 1H), 8.71 (t, J=1.2 Hz, 1H), 8.52 (d, J=5.5 Hz, 2H), 8.11-8.02 (m, 2H), 7.99-7.93 (m, 2H), 7.70 (d, J=3.8 Hz, 1H), 7.40 (d, J=3.8 Hz, 1H), 6.07 (dd, J=10.1, 2.3 Hz, 1H), 4.06-3.95 (m, 1H), 3.91-3.79 (m, 1H), 2.67-2.55 (m, 1H), 2.16-1.98 (m, 2H), 1.90-1.76 (m, 1H), 1.70-1.58 (m, 2H).

2) Synthesis of tert-butyl 4-((5-(3-(pyridin-4-ylcarbamoyl)-1-(tetrahydro-2H-pyran-2-yl)-1H-indazol-5-yl)furan-2-yl)methyl)piperazine-1-carboxylate To a solution of 20-092 (30.0 mg, 0.0720 mmol) in DMF (1 mL) was added tert-butyl piperazine-1-carboxylate (14.8 mg, 0.0792 mmol). In the presence of the catalyst AcOH (0.1 ml), the reaction was conducted at room temperature for 1 hour while stirring. Sodium cyanoborohydride (6.79 mg, 0.108 mmol) was added, followed by stirring at room temperature until completion of the reaction. After completion of the reaction, the reaction mixture was quenched with 2 ml of water. Then, extraction was conducted with ethyl acetate (2×15 ml). The organic layer was washed with water and brine, dried over sodium sulfate, and concentrated by evaporating the solvent in a vacuum. Purification by column chromatography using DCM/MeOH 7% as an eluent afforded 20-097 as a white solid (19.3 mg, 0.0329 mmol, 46%).

LC/MS 587.5[M+H]+

1H NMR (300 MHz, Chloroform-d) δ 9.51 (s, 1H), 8.59 (dd, J=1.6, 0.8 Hz, 1H), 8.49-8.40 (m, 2H), 8.06-7.98 (m, 2H), 7.84 (dd, J=8.9, 1.6 Hz, 1H), 7.72-7.66 (m, 1H), 6.72 (d, J=3.3 Hz, 1H), 6.35 (d, J=3.3 Hz, 1H), 5.82 (dd, J=9.7, 2.5 Hz, 1H), 4.19-4.08 (m, 1H), 3.89-3.80 (m, 1H), 3.48 (q, J=8.4, 6.7 Hz, 4H), 2.53 (t, J=5.1 Hz, 4H), 2.21-2.11 (m, 3H), 1.88-1.74 (m, 3H), 1.46 (s, 9H).

3) Synthesis of 5-(5-(piperazin-1-ylmethyl)furan-2-yl)-N-(pyridin-4-yl)-1H-indazole-3-carboxamide To a solution of 20-097 (14.0 mg, 0.0239 mmol) in DCM (1 ml) were added 4N HCl (0.50 ml) in dioxane. The reaction mixture was stirred overnight at room temperature and concentrated in a vacuum to afford Compound 69 as a white solid (4.6 mg, 0.0114 mmol, 48%).

LC/MS 403.5[M+H]+

1H NMR (400-MHz, Methanol-d4) δ 8.62 (t, J=1.2 Hz, 1H), 8.48 (d, 2H); 7.95 (d, 2H); 7.84 (dt, J=8.5, 1.5 Hz, 1H), 7.70-7.64 (m, 1H), 6.80 (d, 1H), 6.48 (d, J=3.3 Hz, 1H), 3.78 (d, J=5.4 Hz, 2H), 3.20-3.13 (m, 4H), 2.79 (q, J=5.3, 4.2 Hz, 4H).

Compound 70. 5-(5-(Piperidin-1-ylmethyl)furan-2-yl)-N-(pyridin-4-yl)-1-(tetrahydro-2H-pyran-2-yl)-1H-indazole-3-carboxamide

[Reaction Scheme 70]

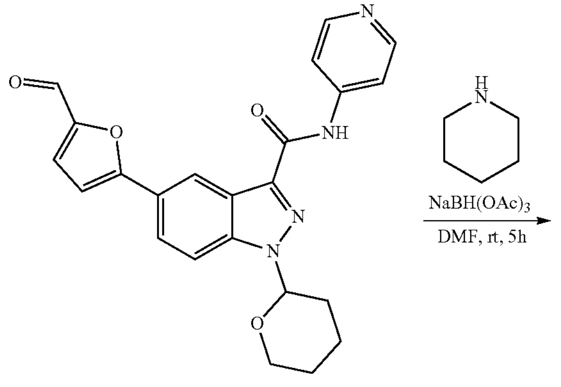

20-092

-continued

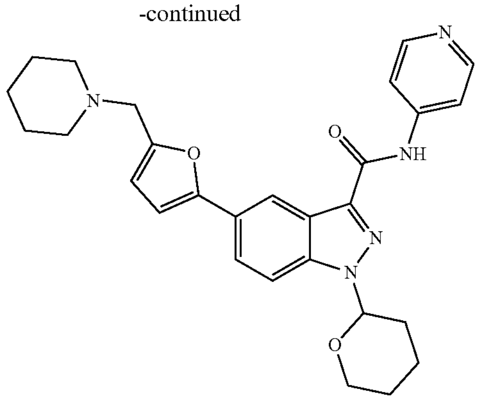

compound 70

To a solution of 20-092 (30.0 mg, 0.0720 mmol) in DMF (1 mL) were added piperidine (6.74 mg, 0.0792 mmol) and sodium triacetoxyborohydride (22.9 mg, 0.108 mmol). At room temperature, the reaction was conducted for 5 hours while stirring. The reaction mixture was quenched with 2 ml of water, followed by extraction with EA (5 ml×2). The organic layer was washed with water and brine, dried over sodium sulfate, and concentrated by evaporating the solvent in a vacuum to give a crude mixture. Purification by column chromatography using DCM/MeOH 7% as an eluent afforded Compound 70 as a beige solid (3.9 mg, 0.00803 mmol, 11%).

LC/MS 486.7[M+H]+

1H NMR (400 MHz, Chloroform-d) δ 8.98 (s, 1H), 8.71-8.65 (m, 1H), 8.64-8.53 (m, 2H), 7.89-7.81 (m, 1H), 7.77-7.71 (m, 2H), 7.69 (d, J=0.9 Hz, 1H), 6.73 (t, J=3.1 Hz, 1H), 6.42 (dd, J=29.5, 3.3 Hz, 1H), 5.81 (dd, J=9.5, 2.6 Hz, 1H), 4.18-4.09 (m, 1H), 3.89-3.84 (m, 1H), 3.82 (s, 2H), 2.69 (s, 3H), 2.60 (t, J=12.1 Hz, 1H), 2.26-2.11 (m, 2H), 1.87-1.83 (m, 1H), 1.78-1.70 (m, 3H), 1.50 (s, 1H).

Compound 71. N-(3,3-dimethyl-1,2,3,4-tetrahydroisoquinolin-7-yl)-5-(2-fluoropyridin-3-yl)-1H-indazole-3-carboxamide

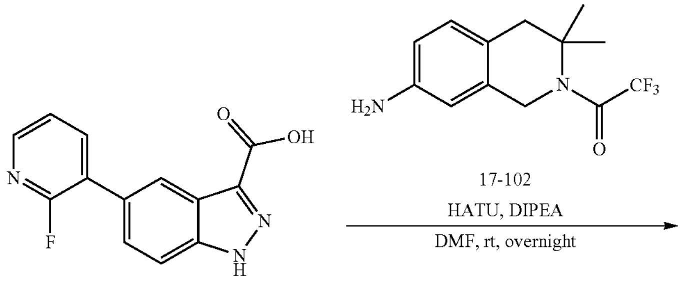

20-240

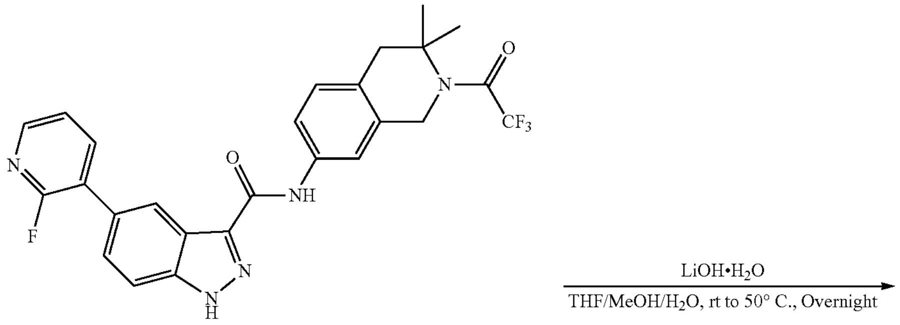

20-256

-continued

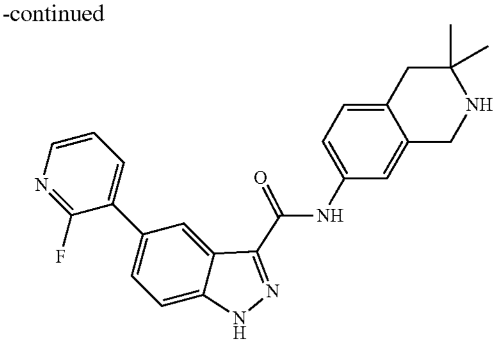

Compound 71

1) Synthesis of N-(3,3-dimethyl-2-(2,2,2-trifluoroacetyl)-1,2,3,4-tetrahydroisoquinolin-7-yl)-5-(2-fluoropyridin-3-yl)-1H-indazole-3-carboxamide To a suspension of 17-102 (23.2 mg, 0.0855 mmol) in THE (1 mL) were added DIPEA (30.2 mg, 0.0934 mmol) and then HATU (35.5 mg, 0.0934 mmol). After addition of 20-240 (20.0 mg, 0.0778 mmol), the reaction mixture was stirred overnight at room temperature. When the starting material was completely consumed as monitored by TLC, the reaction mixture was concentrated by evaporation. EtOAc (20 mL) was added, and the organic layer was washed with water, dried over sodium sulfate, and concentrated in a vacuum. Recrystallization of the reaction mixture in EA/Hex afforded 20-256 as a gray solid (25.1 mg 0.0491 mmol, 63%).

*According to NMR data, the product was formed, but impurities were also observed.

*After reduction it may be removed by washing.

2) Synthesis of N-(3,3-dimethyl-1,2,3,4-tetrahydroisoquinolin-7-yl)-5-(2-fluoropyridin-3-yl)-1H-indazole-3-carboxamide To a solution of 20-256 (10.0 mg, 0.0196 mmol) in THE (1 ml), MeOH (0.5 ml), and $H_2O$ (0.25 ml) was added lithium hydroxide monohydrate (3.30 mg, 0.0782 mmol) at room temperature, and the reaction mixture was stirred overnight, with the temperature elevated from room temperature to 50° C. When the starting material was completely consumed as monitored by TLC, the reaction mixture was concentrated by evaporation in a vacuum. After addition of $H_2O$, the solid thus formed was filtered to afford Compound 71 as a yellow solid (2.1 mg, 0.00505 mmol, 26%).

LCMS [M+H] 416.54

1H NMR (300 MHz, DMSO-d6) δ 10.24 (s, 1H), 8.45 (s, 1H), 8.34-8.13 (m, 2H), 7.84-7.44 (m, 5H), 7.10-6.94 (m, 1H), 3.88 (s, 2H), 2.65 (s, 2H), 1.24 (s, 1H), 1.07 (s, 6H).

Compound 72. 5-(5-(Piperidin-1-ylmethyl)furan-2-yl)-N-(pyridin-4-yl)-1H-indazole-3-carboxamide hydrochloride

[Reaction Scheme 72]

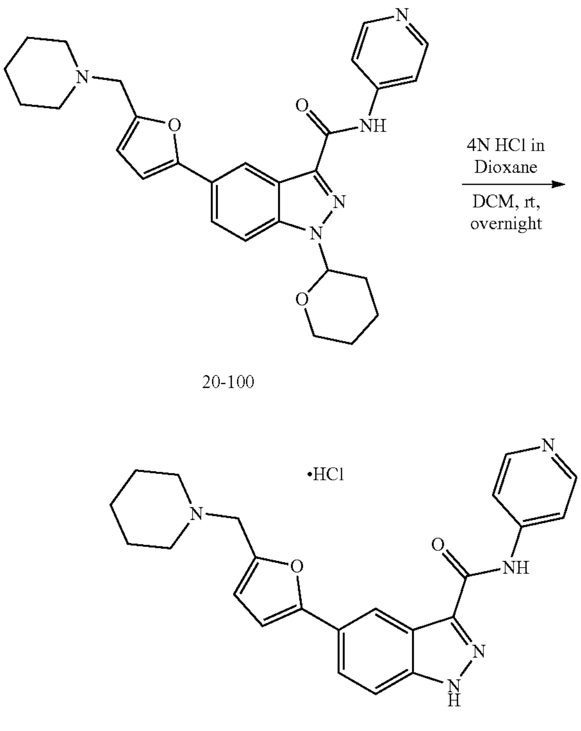

20-100 compound 72

To a solution of 20-100 (20.4 mg, 0.0420 mmol) in DCM (1 ml) was added 4N HCl in dioxane (0.5 ml). The reaction mixture was stirred overnight at room temperature. The reaction mixture was concentrated in a vacuum to afford Compound 72 as a brown solid (15.9 mg, 0.0363, 86%).

LC/MS 402.3[M+H]+

1H NMR (400 MHz, DMSO-d6) δ 14.57 (s, 1H), 11.82 (s, 1H), 10.75 (s, 1H), 8.78 (d, 2H), 8.57 (d, J=1.6 Hz, 1H), 8.47 (d, 2H), 7.99-7.78 (m, 2H), 7.12 (d, J=3.4 Hz, 1H), 6.90 (d, J=3.3 Hz, 1H), 4.46 (s, 2H), 3.11-2.81 (m, 3H), 1.96-1.54 (m, 5H), 1.51-1.27 (m, 1H).

Compound 73. 5-(1-(Piperidin-4-yl)-1H-pyrazol-4-yl)-N-(pyridin-4-yl)-1H-indazole-3-carboxamide hydrochloride

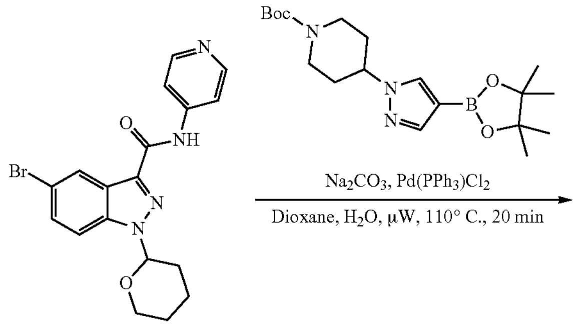

20-321

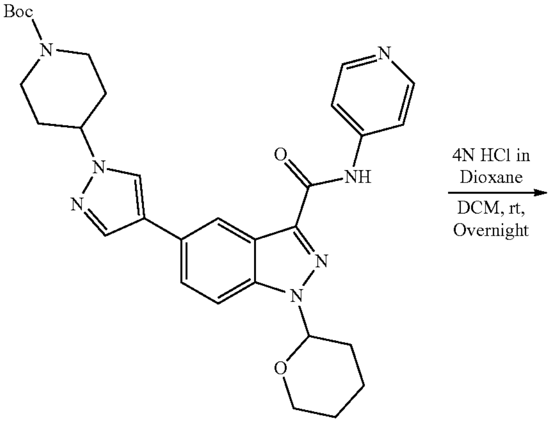

20-324

HCl

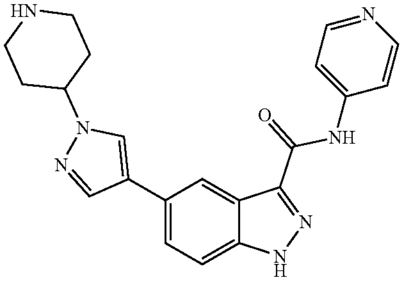

Compound 73

1) Synthesis of tert-butyl 4-(4-(3-(pyridin-4-ylcarbamoyl)-1-(tetrahydro-2H-pyran-2-yl)-1H-indazol-5-yl)-1H-pyrazol-1-yl)piperidine-1-carboxylate A solution of $Na_2CO_3$ (31.8 mg, 0.300 mmol) in water was introduced into a suspension of 20-321 (40.0 mg, 0.0997 mmol), a palladium catalyst (7.00 mg, 0.00997 mmol) and tert-butyl 4-(4-(4,4,5,5-tetramethyl-1,3,2-dioxaborolan-2-yl)-1H-pyrazol-1-yl)piperidine-1-carboxylate (45.1 mg, 0.144 mmol) in dioxane, followed by purging with nitrogen for 15 minutes. The reaction mixture was exposed to microwaves at 110° C. for 20 minutes. The crude reaction mixture was filtered with dioxane and concentrated in a vacuum to give a crude mixture. Purification by column chromatography using MeOH/MC 5% as an eluent afforded 20-324 as a white solid (18 mg, 0.031 mmol, 32%).

1H NMR (300 MHz, DMSO-d6) S 10.60 (s, 1H), 8.50 (d, J=6.3 Hz, 2H), 8.37 (d, J=15.0 Hz, 2H), 8.00-7.87 (m, 4H), 7.80 (dd, J=8.8, 1.6 Hz, 1H), 6.01 (d, J=9.9 Hz, 1H), 4.54-4.29 (m, 1H), 4.19-3.94 (m, 3H), 3.89-3.72 (m, 1H), 3.07-2.82 (m, 2H), 2.65-2.55 (m, 1H), 2.20-1.97 (m, 4H), 1.93-1.74 (m, 3H), 1.72-1.57 (m, 2H), 1.44 (s, 9H).

2) Synthesis of 5-(1-(piperidin-4-yl)-1H-pyrazol-4-yl)-N-(pyridin-4-yl)-1H-indazole-3-carboxamide hydrochloride To a solution of 20-324 (15 mg, 0.0262 mmol) in DCM (1.0 mL) was added 4 N HCl/dioxane (0.5 ml). At room temperature, the reaction was conducted overnight while stirring. When no starting materials were observed as monitored by TCL, the solvent was evaporated in a vacuum to afford Compound 73 as a brown solid (9.2 mg 0.0217 mmol, 83%).

LCMS: M+H 388.32

1H NMR (400 MHz, DMSO-d6) δ 14.36 (s, 1H), 11.82 (s, 1H), 9.21 (s, 1H), 9.01 (d, J=10.1 Hz, 1H), 8.79 (d, J=10.6, 6.5 Hz, 2H), 8.50 (d, J=6.6 Hz, 2H), 8.35 (d, 2H), 8.00 (s, 1H), 7.80 (dd, J=8.7, 1.6 Hz, 1H), 7.75 (d, J=8.7 Hz, 1H), 4.65-4.48 (m, 1H), 3.20-3.01 (m, 3H), 2.36-2.12 (m, 5H).

Example 2. Assay for Inhibitory Activity Against TRIB2 or YAP

Compounds 1 to 73 of the present disclosure, synthesized in Example, were assayed for inhibitory activity against TRIB2 kinase and growth of cancer cells. The results are summarized in Table 1, below. Inhibitory activity against YAP is depicted in FIG. 1.

TRIB2 kinase activity assay was conducted in Eurofins. In brief, human TRIB2 enzyme was first mixed with 8 mM MOPS pH 7.0, 0.2 mM EDTA, and 250 μM substrate (RRRFRPASPLRGPPK) and then treated 10 mM magnesium acetate, 15 μM gamma-33P-ATP, and predetermined concentrations of the test compounds before reaction at room temperature for 120 minutes. Afterward, the reaction was terminated with 0.5% phosphoric acid. Ten μL of the reaction mixture was spotted onto a P30 filter which was then washed four times for 4 minutes with 0.425% phosphoric acid, and dried by treatment with methanol prior to scintillation counting.

Assay for anticancer activity was conducted as follows. Corresponding cancer cells were seeded at a density of 4,000 cells/well into 96-well plates and stabilized for 24 hours. Thereafter, the cells in each well were treated with 10 μM of the each of the compounds for 3 days. Then, cell viability was assayed using Cell Counting Kit-8 from Dojindo.

TABLE 1

| | TRIB2 Kinase activity assay | Cell viability (% of Con. 10 μM) | | | |
|---|---|---|---|---|---|
| compound no. | $IC_{50}$ | U937 | K562 | A549 | HepG2 |
| compound 1 | + + | 34 | 49 | NT | NT |
| compound 2 | + + | 12 | 16 | | |
| compound 4 | + + | 50 | 41 | | |
| compound 10 | + + | NT | NT | | |
| compound 11 | + | | | | |
| compound 12 | + + | | | | |
| compound 13 | + + | | | | |
| compound 14 | + | | | | |
| compound 16 | + | | | | |
| compound 17 | + + + | | | 17 | 15 |

TABLE 1-continued

| compound no. | TRIB2 Kinase activity assay IC$_{50}$ | Cell viability (% of Con. 10 μM) U937 | K562 | A549 | HepG2 |
|---|---|---|---|---|---|
| compound 18 | + | | | NT | NT |
| compound 19 | + | | | | |
| compound 20 | + + | | | | |
| compound 21 | + | | | | |
| compound 22 | + | | | | |
| compound 24 | + + + | | | 9 | 10 |
| compound 26 | + + | | | 30 | 24 |
| compound 28 | + + | | | 17 | 16 |
| compound 29 | + + | | | 31 | 18 |
| compound 33 | + + + | | | 20 | 13 |
| compound 34 | + + | | | 51 | 49 |
| compound 36 | + + + | | | 26 | 15 |
| compound 46 | + + | | | 58 | 46 |
| compound 47 | + + | | | 55 | 32 |
| compound 51 | + + | | | 44 | 37 |
| compound 52 | + + | | | 39 | 32 |
| compound 53 | + + + | | | 13 | 10 |
| compound 55 | + + + | | | 10 | 12 |
| compound 59 | + + + | | | 2 | 6 |
| compound 63 | + + + | | | 4 | 7 |
| compound 64 | + + + | | | 8 | 7 |
| compound 65 | + + | | | 24 | 28 |
| compound 68 | + + | | | 55 | 11 |
| compound 71 | + + + | | | 10 | 9 |
| compound 73 | + + | | | 49 | 36 |

IC$_{50}$(Inhibitory concentration 50%): + + +(0.001~0.01 μM), + +(0.01~0.1 μM), +(0.1~1 μM)
NT: not tested As shown in FIG. 1, the compounds of the present disclosure inhibited the phosphorylation of TRIB2 and YAP in the liver cancer cell strain (HepG2) in a dose-dependent manner and Compound 17 was also confirmed to reduce the level of p-YAP in the ovarian cancer cell line A2780.

The assay for inhibitory activity against TRIB2 kinase and cancer cell growth indicated that the indazole derivatives of the present disclosure exhibited excellent inhibitory activity, with IC$_{50}$ values measured in the range of 0.001-1 μM. In addition to being highly inhibitory of the growth of liver cancer cell line HepG2, Compound 17 was found to have inhibitory activity against YAP and promote YAP protein degradation. Particularly, remarkable inhibitory activity against TRIB2 kinase and cancer cell growth was measured from the compound having a tetrhydroisoquinoline substituent introduced thereinto according to Chemical Formula 2 of the present disclosure.

Taken together, the data obtained above indicate that the indazole derivatives of the present disclosure can be advantageously applied to the prevention or treatment of cancers, narcolepsy, and fasciitis, which are diseases associated with TRIB2.

Formulation Example 1. Preparation of Powder

Compound 17 of the present disclosure (5-(2-fluoropyridin-3-yl)-N-(pyridin-4-yl)-1H-indazole-3-carboxamide) 2 g, and lactose 1 g were mixed and loaded into an airtight sac to give a powder.

Formulation Example 2. Preparation of Tablet

Compound 17 of the present disclosure (5-(2-fluoropyridin-3-yl)-N-(pyridin-4-yl)-1H-indazole-3-carboxamide) 100 mg, microcrystalline cellulose 100 mg, lactose hydrate 60 mg, low-substituted hydroxypropyl cellulose 20 mg, and magnesium stearate 2 mg were mixed and compressed into a tablet according to a typical tableting method.

Formulation Example 3. Preparation of Capsule

Compound 17 of the present disclosure (5-(2-fluoropyridin-3-yl)-N-(pyridin-4-yl)-1H-indazole-3-carboxamide) 100 mg, microcrystalline cellulose 100 mg, lactose hydrate 60 mg, low-substituted hydroxypropyl cellulose 20 mg, and magnesium stearate 2 mg were mixed and loaded into a gelatin capsule according to a typical method to give a capsule.

Formulation Example 4. Preparation of Pill

Compound 17 of the present disclosure (5-(2-fluoropyridin-3-yl)-N-(pyridin-4-yl)-1H-indazole-3-carboxamide) 90 mg, glutinous rice starch 5 mg and purified water 5 mg were mixed together with a small amount of anti-hygroscopic additives including dextrin, maltodextrin, corn starch, and microcrystalline cellulose (MCC) and the mixture was prepared into a pill 100 mg according to a typical method.

Formulation Example 5. Preparation of Injection

Compound 17 of the present disclosure (5-(2-fluoropyridin-3-yl)-N-(pyridin-4-yl)-1H-indazole-3-carboxamide) 10 mg was mixed together a suitable amount of sterile distilled water for injection, and a suitable amount of a pH adjuster and the mixture was put into an ample (2 ml) according to a conventional method.

The invention claimed is:

1. A compound represented by Chemical Formula 1 below, an optical isomer thereof, or a acceptable salt thereof:

[Chemical Formula 1]

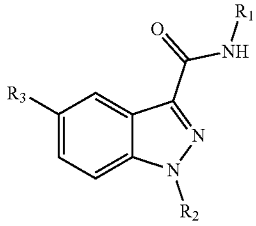

wherein, $R_1$ is a substituted or unsubstituted tetrahydroisoquinoline, wherein the substituted tetrahydroisoquinoline has as a substituent at least one selected from the group consisting of a hydrogen atom, a $C_1$-$C_4$ alkyl, halogen, —$NH_2$, —OH, Boc(tert-butoxycarbonyl), C(=O)$NH_2$, C(=O)$CF_3$,

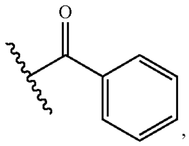, and 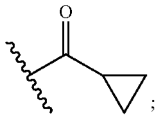;

$R_2$ is a substituent selected from the group consisting of a hydrogen atom, a $C_1$-$C_6$ alkyl, acetyl, trifluoroacetyl, Boc(tert-butoxycarbonyl),

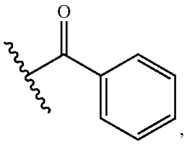
,
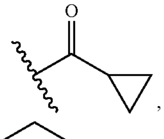
, and
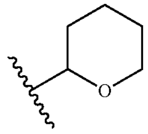
;

and $R_3$ is a substituted or unsubstituted $C_4$-$C_{12}$ aryl, a substituted or unsubstituted $C_4$-$C_{12}$ heteroaryl, a substituted or unsubstituted $C_4$-$C_{12}$ heterocycloalkyl, or a substituted or unsubstituted pyridine, wherein the substituted $C_4$-$C_{12}$ aryl, $C_4$-$C_{12}$ heteroaryl, $C_4$-$C_{12}$ heterocycloalkyl, or pyridine has as a substituent at least one selected from the group consisting of a hydrogen atom, halogen, a $C_1$-$C_6$ alkyl, a $C_4$-$C_6$ heterocycloalkyl, a $C_1$-$C_4$ alkyl $C_4$-$C_6$ heterocycloalkyl, a $C_1$-$C_4$ alkyl $C_4$-$C_6$ aryl, and

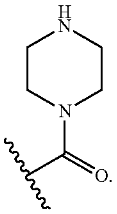 [SMILES: *C(=O)N1CCNCC1]
.

2. The compound, optical isomer, or pharmaceutical acceptable salt of claim 1, wherein the halogen is fluorine, chlorine, bromine or iodine;

the $C_1$-$C_4$ alkyl is methyl, ethyl, propyl, n-butyl, iso-butyl, tert-butyl, or 1-methylpropyl;

the heterocycloalkyl is aziridinyl, pyrrolidinyl, piperidinyl, piperazinyl, morpholinyl, tetrahydrofuranyl, tetrahydropyranyl, tetrahydroisoquinoline; and the heteroaryl is pyridinyl, pyrrolyl, furanyl, pyrimidinyl or pyranyl.

3. A compound represented by Chemical Formula 2 below, an optical isomer thereof, or a pharmaceutically acceptable salt thereof:

[Chemical Formula 2]

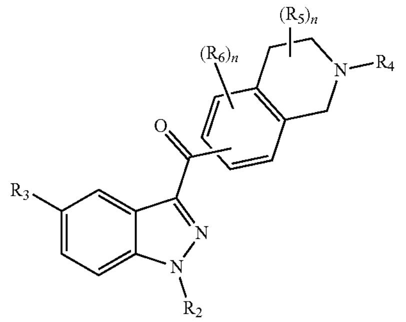

wherein, $R_2$ is a substituent selected from the group consisting of a hydrogen atom, a $C_1$-$C_6$ alkyl, acetyl, trifluoroacetyl, Boc(tert-butoxycarbonyl), and

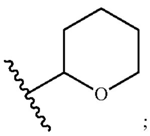 [SMILES: *C1CCCCO1]
;

$R_3$ is a substituted or unsubstituted $C_4$-$C_{12}$ aryl, a substituted or unsubstituted $C_4$-$C_{12}$ heteroaryl, a substituted or unsubstituted $C_4$-$C_{12}$ heterocycloalkyl, or a substituted or unsubstituted pyridine, wherein the substituted $C_4$-$C_{12}$ aryl, $C_4$-$C_{12}$ heteroaryl, $C_4$-$C_{12}$ heterocycloalkyl, or pyridine has as a substituent at least one selected from the group consisting of a hydrogen atom, halogen, a $C_1$-$C_6$ alkyl, a $C_4$-$C_6$ heterocycloalkyl, a $C_1$-$C_4$ alkyl $C_4$-$C_6$ heterocycloalkyl, a $C_1$-$C_4$ alkyl $C_4$-$C_6$ aryl, or

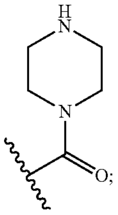 [SMILES: *C(=O)N1CCNCC1]
;

$R_4$ is a substituent selected from the group consisting of a hydrogen atom, a $C_1$-$C_6$ alkyl, acetyl, and trihaloacetyl;

$R_5$ are each independently a substituent selected from the group consisting of a hydrogen atom, hydroxy, halogen, and a $C_1$-$C_6$ alkyl;

$R_6$ are each independently a substituent selected from the group consisting of a hydrogen atom, hydroxy, nitro, amino, halogen, a $C_1$-$C_4$ alkyl, and a $C_1$-$C_4$ alkoxy; and n is an integer of 0, 1, or 2.

4. The compound, optical isomer, and pharmaceutically acceptable salt of claim 1, wherein the compound is selected from the group consisting of:

(3,4-dihydroisoquinolin-2-(1H)-yl)(5-(2-fluoropyridin-3-yl)-1H-indazol-3-yl)methanone (Compound 21);

5-(2-fluoropyridin-3-yl)-N-(2-(2,2,2-trifluoroacetyl)-1,2,3,4-tetrahydroisoquinolin-7-yl)-1H-indazole-3-carboxamide (Compound 24);

5-(2-fluoropyridin-3-yl)-1-(tetrahydro-2H-pyran-2-yl)-N-(2-(2,2,2-trifluoroacetyl)-1,2,3,4-tetrahydroisoquinolin-7-yl)-1H-indazole-3-carboxamide (Compound 53);

5-(2-fluoropyridin-3-yl)-1-(tetrahydro-2H-pyran-2-yl)-N-(1,2,3,4-tetrahydroisoquinolin-7-yl)-1H-indazole-3-carboxamide (Compound 54);

5-(2-fluoropyridin-3-yl)-N-(1,2,3,4-tetrahydroisoquinolin-7-yl)-1H-indazole-3-carboxamide hydrochloride (Compound 55);

N-(1,1-dimethyl-2-(2,2,2-trifluoroacetyl)-1,2,3,4-tetrahydroisoquinolin-7-yl)-5-(2-fluoropyridin-3-yl)-1H-indazole-3-carboxamide (Compound 58);

N-(1,1-dimethyl-1,2,3,4-tetrahydroisoquinolin-7-yl)-5-(2-fluoropyridin-3-yl)-1H-indazole-3-carboxamide (Compound 59);

5-(2-fluoropyridin-3-yl)-N-(1-methyl-1,2,3,4-tetrahydroisoquinolin-7-yl)-1H-indazole-3-carboxamide (Compound 63);

5-(2-fluoropyridin-3-yl)-N-(1,2,3,4-tetrahydroisoquinolin-6-yl)-1H-indazole-3-carboxamide (Compound 64);

N-(3,3-dimethyl-1,2,3,4-tetrahydroisoquinolin-7-yl)-5-(2-fluoropyridin-3-yl)-1H-indazole-3-carboxamide (Compound 71).

5. A pharmaceutical composition comprising the compound represented by Chemical Formula 1, the optical isomer thereof, or the pharmaceutically acceptable salt thereof in claim 1, as an active ingredient for treatment of cancer, narcolepsy, or fasciitis.

6. The pharmaceutical composition of claim 5, wherein the cancer is selected from the group consisting of: lung cancer, liver cancer, stomach cancer, colorectal cancer, bladder cancer, prostate cancer, breast cancer, ovarian cancer, cervical cancer, thyroid cancer, melanoma, blood cancer, colon cancer, non-small cell lung cancer, pancreatic cancer, skin cancer, head and neck cancer, small bowel cancer, rectal cancer, endometrial cancer, vaginal cancer, testis cancer, esophageal cancer, bile duct cancer, lymph gland cancer, gall bladder cancer, endocrine gland cancer, adrenal cancer, lymphoma, multiple myeloma, thymoma, mesothelioma, kidney cancer, brain cancer, tumors of central nervous system, brainstem glioma, and pituitary adenoma.

7. A pharmaceutical composition comprising the compound represented by Chemical Formula 2, the optical isomer thereof, or the pharmaceutically acceptable salt thereof in claim 3, as an active ingredient for treatment of cancer, narcolepsy, or fasciitis.

8. The pharmaceutical composition of claim 7, wherein the cancer is selected from the group consisting of: lung cancer, liver cancer, stomach cancer, colorectal cancer, bladder cancer, prostate cancer, breast cancer, ovarian cancer, cervical cancer, thyroid cancer, melanoma, blood cancer, colon cancer, non-small cell lung cancer, pancreatic cancer, skin cancer, head and neck cancer, small bowel cancer, rectal cancer, endometrial cancer, vaginal cancer, testis cancer, esophageal cancer, bile duct cancer, lymph gland cancer, gall bladder cancer, endocrine gland cancer, adrenal cancer, lymphoma, multiple myeloma, thymoma, mesothelioma, kidney cancer, brain cancer, tumors of central nervous system, brainstem glioma, and pituitary adenoma.

9. A method for treatment of a disease or condition, comprising administering to a subject in need thereof an effective amount of the pharmaceutical composition of claim 5, wherein the disease or condition is cancer, narcolepsy, or fasciitis.

10. The method of claim 9, wherein the cancer is selected from the group consisting of: lung cancer, liver cancer, stomach cancer, colorectal cancer, bladder cancer, prostate cancer, breast cancer, ovarian cancer, cervical cancer, thyroid cancer, melanoma, blood cancer, colon cancer, non-small cell lung cancer, pancreatic cancer, skin cancer, head and neck cancer, small bowel cancer, rectal cancer, endometrial cancer, vaginal cancer, testis cancer, esophageal cancer, bile duct cancer, lymph gland cancer, gall bladder cancer, endocrine gland cancer, adrenal cancer, lymphoma, multiple myeloma, thymoma, mesothelioma, kidney cancer, brain cancer, tumors of central nervous system, brainstem glioma, and pituitary adenoma.

11. A method for treatment of a disease or condition, comprising administering to a subject in need thereof an effective amount of the pharmaceutical composition of claim 7, wherein the disease or condition is cancer, narcolepsy, or fasciitis.

12. The method of claim 11, wherein the cancer is selected from the group consisting of: lung cancer, liver cancer, stomach cancer, colorectal cancer, bladder cancer, prostate cancer, breast cancer, ovarian cancer, cervical cancer, thyroid cancer, melanoma, blood cancer, colon cancer, non-small cell lung cancer, pancreatic cancer, skin cancer, head and neck cancer, small bowel cancer, rectal cancer, endometrial cancer, vaginal cancer, testis cancer, esophageal cancer, bile duct cancer, lymph gland cancer, gall bladder cancer, endocrine gland cancer, adrenal cancer, lymphoma, multiple myeloma, thymoma, mesothelioma, kidney cancer, brain cancer, tumors of central nervous system, brainstem glioma, and pituitary adenoma.

* * * * *